United States Patent
Greenberg et al.

(10) Patent No.: US 9,778,250 B2
(45) Date of Patent: Oct. 3, 2017

(54) DETECTING INCLUSION BODY MYOSITIS

(75) Inventors: Steven A. Greenberg, Newton, MA (US); Mohammad K. Salajegheh, Boston, MA (US)

(73) Assignees: The Brigham and Women's Hospital, Inc., Boston, MA (US); Children's Medical Center Corporation, Boston, MA (US)

( * ) Notice: Subject to any disclaimer, the term of this patent is extended or adjusted under 35 U.S.C. 154(b) by 227 days.

(21) Appl. No.: 14/116,540

(22) PCT Filed: May 10, 2012

(86) PCT No.: PCT/US2012/037275
§ 371 (c)(1),
(2), (4) Date: Apr. 18, 2014

(87) PCT Pub. No.: WO2012/154933
PCT Pub. Date: Nov. 15, 2012

(65) Prior Publication Data
US 2014/0370526 A1    Dec. 18, 2014

Related U.S. Application Data

(60) Provisional application No. 61/484,279, filed on May 10, 2011.

(51) Int. Cl.
*G01N 33/543* (2006.01)
*G01N 33/564* (2006.01)
*C12N 9/16* (2006.01)

(52) U.S. Cl.
CPC .......... *G01N 33/54306* (2013.01); *C12N 9/16* (2013.01); *G01N 33/564* (2013.01); *C07K 2319/00* (2013.01); *C07K 2319/21* (2013.01); *C07K 2319/23* (2013.01); *C07K 2319/43* (2013.01); *G01N 2333/46* (2013.01); *G01N 2800/10* (2013.01); *G01N 2800/52* (2013.01)

(58) Field of Classification Search
CPC .......... G01N 33/54306; G01N 33/564; G01N 2333/46; G01N 2800/10; G01N 2800/52; C12N 9/16; C07K 2319/00; C07K 2319/21; C07K 2319/23; C07K 2319/43
See application file for complete search history.

(56) References Cited

U.S. PATENT DOCUMENTS

2008/0221019 A1    9/2008  Olbe et al.

FOREIGN PATENT DOCUMENTS

| WO | 02/04613 | 1/2002 |
|----|----------|--------|
| WO | WO 2013006059 A1 | 1/2013 |

OTHER PUBLICATIONS

Lilley et al. "Two-dimensional gel electrophoresis: recent advances in sample preparation, detection and quantitation" (Curr Opin Chem Biol (2002) 6:46-50.*
McCormick et al., Trypanosoma cruzi: Recongition of a 43-kDa Muscle Glycoprotein by autoantibodies Present during Murine Infection, Experimental Parasitology, 77, 1993, pp. 273-281.*
Dalakas et al., Ann Neurol., 41(1):100-104 (1997). "Inclusion body myositis and paraproteinemia: incidence and immunopathologic correlations."
DRG User's Manual, Myositis Screen Blot DOT-5121 / DOT-5122, pp. 1-15, Version 1.0 (2010).
Orgentec Diagnostika GmbH, Instruction for Use, ORG 760-08/ORG 760-16 Myositis plus, pp. 1-5 (Jan. 2011).
Amato et al., J Neurol Neurosurg Psychiatry, 80:1186-1193 (2009). "Inclusion body myositis: old and new concepts."
Hunsucker et al., Journal of Biological Chemistry, 276(13):10498-1054 (2001). "Human cytosolic 5'nucleotidase I characterization and role in nucleoside analog resistance."
Meyer et al., Scientific presentation at the 8th Dresden Symposium on Autoantibodies (Dresden, Germany), Sep. 2007. "EUROLINE Myositis Profile: A new developed line immunoassay for the detection of myositis specific autoantibodies."
Salajegheh et al., Muscle Nerve, 40:19-31 (2009). "Sarcoplasmic redistribution of nuclear TDP-43 in inclusion body myositis."
Sordet et al., Joint Bone Spine, 73:646-654 (2006). "Contribution of autoantibodies to the diagnosis and nosology of inflammatory muscle disease."
Weihl et al., J Neurol Neurosurg Psychiatry, 79(10):1186-1189 (2008). "TDP-43 accumulation in IBM muscle suggests a common pathogenic mechanism with frontotemporal dementia."
Zampieri et al., Basic Appl Myol, 12(1):27-31 (2002). "Autoantibodies in idiopathic inflammatory myopathies."

* cited by examiner

*Primary Examiner* — Gary W Counts
(74) *Attorney, Agent, or Firm* — Nixon Peabody LLP; David S. Resnick; Tari W. Mills

(57) ABSTRACT

Methods, devices, kits and systems for diagnosing inclusion body myositis (IBM) are provided. Methods, devices, kits and systems involves detecting the presence and/or level of autoantibodies that are reactive against at least a ~43 kilodalton (kDa) protein or ~43 kDa protein band from a muscle lysate or a mammalian cell lysate, or autoantibodies that are reactive against a cytosolic 5'-nucleotidase 1A protein (NT5C1A), or a cytosolic 5'-nucleotidase 1B protein (NT5C1B), or a NT5C1B isoform thereof, or a peptide fragment thereof, an isolated peptide thereof or a fusion protein comprising an isolated peptide of NT5C1A or NT5C1B. Such autoantibodies are only found in IBM patients and not in patients with other myopathies.

4 Claims, 9 Drawing Sheets

Figure 2

```
SP|Q96P26|5NT1B_HUMAN      MSQTSLKQKKNEPGMRSSKESLEAEKRKESDKTGVRLSNQMRRAVNPNHSLRCCPFQGHS  60
SP|Q96P26-2|5NT1B_HUMAN    MSQTSLKQKKNEPGMRSSKESLEAEKRKESDKTGVRLSNQ---------------------  40
SP|Q96P26-3|5NT1B_HUMAN    ------------------------EAEKRKESDKTGVRLSNQMRRAVNPNHSLRCCPFQGHS  63
SP|Q96P26-4|5NT1B_HUMAN    MSQTSLKQKKNEPGMRSSKES-EAEKRKESDKTGVRLSNQMRRAVNPNHSLRCCPFQGHS  60

SP|Q96P26|5NT1B_HUMAN      SCRRCICAAEG-ALGPCHTIRIYIHMCLIWEQGQQITMMRGSQESSLRKTDSRGYIVRSQ 120
SP|Q96P26-2|5NT1B_HUMAN    ------------------------------------GSQESSLRKTDSRGYIVRSQ  60
SP|Q96P26-3|5NT1B_HUMAN    -----------------------------------------------------------
SP|Q96P26-4|5NT1B_HUMAN    SCRRC-CAAEGTALGPCHTIRIYIHMCLIWEQGQQITMMRGSQESSLRKTDSRGYIVRSQ 120

SP|Q96P26|5NT1B_HUMAN      WSRISRSPSTKAPSIDEPRSRNTSAKLPSSSTSSRTPSTSPSLHDSSPPP-SGQPS-QPP 180
SP|Q96P26-2|5NT1B_HUMAN    WSRISRSPSTKAPS-DEPRSRNTSAKLPSSSTSSRTPSTSPSLHDSSPPPLSGQPSLQPP 120
SP|Q96P26-3|5NT1B_HUMAN    -----------------------------------------------------------
SP|Q96P26-4|5NT1B_HUMAN    WSRISRSPSTKAPSIDEPRSRNTSAKLPSSSTSSRTPSTSPSLHDSSPPPLSGQPSLQPP 180

SP|Q96P26|5NT1B_HUMAN      ASPQLPRSLDSRPPTPEPDPGSRRSTKMQENPEAWAQGIVREIRQTRDSQPLEYSRTSP 240
SP|Q96P26-2|5NT1B_HUMAN    ASPQLPRSLDSRPPTPEPDPGSRRSTKMQENPEAWAQGIVREIRQTRDSQPLEYSRTSP 180
SP|Q96P26-3|5NT1B_HUMAN    -MQENPEAWAQGIVREIRQTRDSQPLEYSRTSP  32
SP|Q96P26-4|5NT1B_HUMAN    ASPQLPRSLDSRPPTPEPDPGSRRSTKMQENPEAWAQGIVRE-RQ-RDSQPLEYSRTSP 240
                                                          *  ***************

SP|Q96P26|5NT1B_HUMAN      TEWKSSSQRRGIYPASTQ-DRNS-SEQQQQQREDEDDYEAAYWASMRSFYEKNPSCSRPW 300
SP|Q96P26-2|5NT1B_HUMAN    TEWKSSSQRRGIYPASTQLDRNSLSEQQQQQREDEDDYEAAYWASMRSFYEKNPSCSRPW 240
SP|Q96P26-3|5NT1B_HUMAN    TEWKSSSQRRG-YPASTQLDRNSLSEQQQQQREDEDDYEAAYWASMRSFYEKNPSCSRPW  92
SP|Q96P26-4|5NT1B_HUMAN    TEWKSSSQRRGIYPASTQLDRNSLSEQQQQQREDEDD-EAAYWASMRSFYEKNPSCSRPW 300
                           ***********

SP|Q96P26|5NT1B_HUMAN      PPKPKNAITIA-SSCALFNMVDGRKIYEQEGLEKYMEYQLTNENVILTPGPAFRFVKALQ 360
SP|Q96P26-2|5NT1B_HUMAN    PPKPKNAITIALSSCALFNMVDGRKIYEQEG-EKYMEYQLTNENVILTPGPAFRFVKALQ 300
SP|Q96P26-3|5NT1B_HUMAN    PPKPKNAITIALSSCALFNMVDGRKIYEQEGLEKYMEYQLTNENVI-TPGPAFRFVKALQ 152
SP|Q96P26-4|5NT1B_HUMAN    PPKPKNAITIALSSCALFNMVDGRKIYEQEGLEKYMEYQLTNENVILTPGPAFRFVKALQ 360
                           *************
```

Figure 2 (continued)

```
SP|Q96P26|5NT1B_HUMAN    YVNARLRDLYPDEQDLFDIVLMTNNHAQVGVRLINSVNHYGLLIDRFCLTGGKDPIGYLK  420
SP|Q96P26-2|5NT1B_HUMAN  YVNARLRDLYPDEQDLFDIVLMTNNHAQVGVRLINSVNHYGLLIDRFCLTGGKDPIGYLK  360
SP|Q96P26-3|5NT1B_HUMAN  YVNARLRDLYPDEQDLFDIVLMTNNHAQVGVRLINSVNHYGLLIDRFCLTGGKDPIGYLK  212
SP|Q96P26-4|5NT1B_HUMAN  YVNARLRDLYPDEQDLFDIVLMTNNHAQVGVRLINSVNHYGLLIDRFCLTGGKDPIGYLK  420
                         ************************************************************

SP|Q96P26|5NT1B_HUMAN    AYLTNLYIAADSEKVQEAIQEGIASATMFDGAKDMAYCDTQLRVAFDGDAVLFSDESEHF  480
SP|Q96P26-2|5NT1B_HUMAN  AYLTNLYIAADSEKVQEAIQEGIASATMFDGAKDMAYCDTQLRVAFDGDAVLFSDESEHF  420
SP|Q96P26-3|5NT1B_HUMAN  AYLTNLYIAADSEKVQEAIQEGIASATMFDGAKDMAYCDTQLRVAFDGDAVLFSDESEHF  272
SP|Q96P26-4|5NT1B_HUMAN  AYLTNLYIAADSEKVQEAIQEGIASATMFDGAKDMAYCDTQLRVAFDGDAVLFSDESEHF  480
                         ************************************************************

SP|Q96P26|5NT1B_HUMAN    TKEHGLDKFFQYDTLCESKPLAQGPLKGFLEDLGRLQKKFYAKNERLLCPIRTYLVTARS  540
SP|Q96P26-2|5NT1B_HUMAN  TKEHGLDKFFQYDTLCESKPLAQGPLKGFLEDLGRLQKKFYAKNERLLCPIRTYLVTARS  480
SP|Q96P26-3|5NT1B_HUMAN  TKEHGLDKFFQYDTLCESKPLAQGPLKGFLEDLGRLQKKFYAKNERLLCPIRTYLVTARS  332
SP|Q96P26-4|5NT1B_HUMAN  TKEHGLDKFFQYDTLCESKPLAQGPLKGFLEDLGRLQKKFYAKNERLLCPIRTYLVTARS  540
                         ************************************************************

SP|Q96P26|5NT1B_HUMAN    AASSGARVLKTLRRWGLEIDEALFLAGAPKSPILVKIRPHIFFDDHMFHIEGAQRLGSIA  600
SP|Q96P26-2|5NT1B_HUMAN  AASSGARVLKTLRRWGLEIDEALFLAGAPKSPILVKIRPHIFFDDHMFHIEGAQRLGSIA  540
SP|Q96P26-3|5NT1B_HUMAN  AASSGARVLKTLRRWGLEIDEALFLAGAPKSPILVKIRPHIFFDDHMFHIEGAQRLGSIA  392
SP|Q96P26-4|5NT1B_HUMAN  AASSGARVLKTLRRWGLEIDEALFLAGAPKSPILVKIRPHIFFDDHMFHIEGAQRKSLG-  599
                         ***********************************************************

SP|Q96P26|5NT1B_HUMAN    AYGFNKKFSS  610
SP|Q96P26-2|5NT1B_HUMAN  AYGFNKKFSS  550
SP|Q96P26-3|5NT1B_HUMAN  AYGFNKKFSS  402
SP|Q96P26-4|5NT1B_HUMAN  ---WMS----  602
                         ..:
```

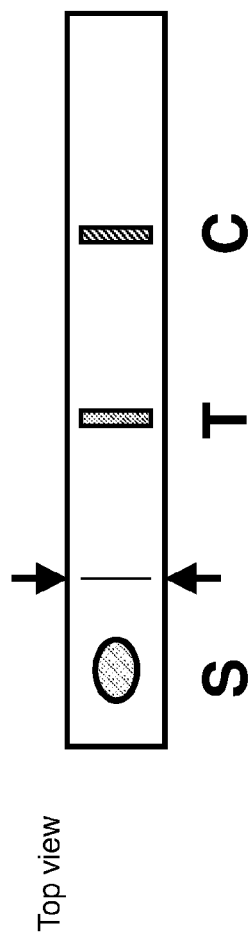
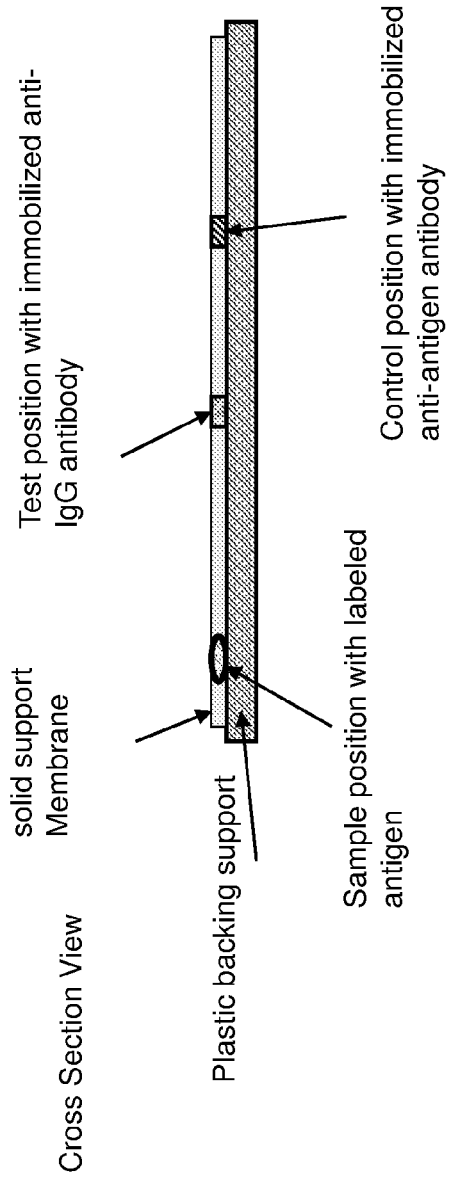
FIGURE 3A
FIGURE 3B

DETECTING INCLUSION BODY MYOSITIS

CROSS REFERENCE TO RELATED APPLICATIONS

This application is a 35 U.S.C. §371 National Phase Entry Application of International Application No. PCT/US2012/037275 filed May 10, 2012, which designates the U.S., and which claims benefit under 35 U.S.C. §119(e) of U.S. Provisional Application No. 61/484,279 filed May 10, 2011, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 18, 2014, is named Sequence_Listing_043214_070742_US.txt and is 27,320 bytes in size.

TECHNOLOGICAL FIELD

Embodiments of the technology described herein relate to the development of non-invasive diagnostics for the disorder inclusion body myositis.

BACKGROUND

Myositis is one form of inflammatory myopathy involving chronic inflammation of the skeletal muscles. It is a rare disease in which the immune system chronically inflames the body's muscle tissue. The etiology of the immune system's attack in currently unknown. Persistent inflammation progressively weakens the muscles, causing muscle soreness, joint pain and fatigue.

Myositis can take several forms and usually develops slowly over time and can range in severity from mild to debilitating or worse. The three major types of myositis are dermatomyositis (DM), polymyositis (PM), and inclusion body myositis (IBM). PM affects skeletal muscles on both sides of the body and mostly affects people between the ages of 31 and 60. Progressive muscle weakness often leads to difficulty swallowing (dysphagia), rising from a sitting position, climbing stairs, lifting objects, or reaching overhead. People with PM may also experience arthritis, shortness of breath, and heart arrhythmias.

In addition to progressive muscle weakness, patients with DM have a characteristic skin rash that precedes or accompanies progressive muscle weakness. The rash looks patchy, with purple or red discolorations, and is characteristically found on the eyelids and on skin overlying joints of knuckles, elbows, knees, and toes. Red rashes are also found on other locations such as the face, neck, shoulders, upper chest, and back. The rash sometimes occurs without obvious muscle involvement.

IBM is characterized by gradual (over months or years) progressive muscle weakness and wasting that affect both proximal and distal muscles. IBM affects individuals in a variety of different ways from the age of onset. Symptoms of the disease usually begin after the age of 50, although the disease can occur earlier. Muscle weakness may affect only one side of the body. Falling and tripping are usually the first noticeable symptoms of IBM. For some individuals the disorder begins with weakness in the wrists and fingers that causes difficulty with pinching, buttoning, and gripping objects. There may be weakness of the wrist and finger muscles and atrophy (thinning or loss of muscle bulk) of the forearm muscles and quadriceps muscles in the legs. Difficulty swallowing occurs in approximately half of IBM cases. Unlike PM and DM, IBM occurs more frequently in men than in women. In addition to physically symptomatic changes, the muscles of IBM patients have small degenerative structures that with special staining appear as holes called vacuoles in the affected muscle fibers.

Diagnosing IBM can be challenging. Circulating autoantibodies, such as anti-Jo and anti-SRP, have been identified in PM and DM, and have been used to aid both in diagnosis and the treatment of these two conditions. However, to date, no autoantibody has been reported to be associated with IBM. Because IBM affects different people in different ways and at different rates, there is no "textbook case" of IBM. Consequently, IBM is often initially misdiagnosed and a definitive diagnosis is delayed. IBM is often misdiagnosed as some other inflammatory myopathy, usually PM. For example, a course of prednisone is typically completed with no improvement and eventually IBM is suspected. IBM weakness comes on over months or years and progresses steadily, whereas PM has an onset of weeks or months. Nowadays, differential diagnosis of IBM involves systematically ruling out other possible causes such PM, DM, chronic inflammatory demyelinating polyradiculoneuropathy, Duchenne muscular dystrophy, and myasthenia gravis etc. Currently the only definitive test for IBM is a muscle biopsy to confirm the physical changes in the affected muscles.

SUMMARY

Embodiments of the technology described herein are based on the discovery of circulating autoantibodies that are specific to inclusion body myositis (IBM) and not dermatomyositis (DM) and polymyositis (PM). In the blood samples of patients with IBM, there are autoantibodies that target at least one ~43 kilodalton (kDa) protein in a muscle lysate. The discovery was performed by one-dimension sodium dodecyl sulfate polyacrylamide gel electrophoresis (1D SDS-PAGE) under denaturing conditions and Western blot analysis. There are also autoantibodies that target to a ~41 kDa cytosolic 5'-nucleotidase 1A protein (NT5C1A) and isoforms of a cytosolic 5'-nucleotidase 1B protein (NT5C1B) (45 kDa-69 kDa). Healthy patients free of any inflammation conditions and patients with other myositis, e.g., PM and DM, do not have any such autoantibodies.

The objective here is to provide non-invasive diagnostic methods, assays, devices, kits and systems for diagnosing the likelihood of IBM. The correlation of the presence autoantibodies against at least one ~43 kDa protein, NTC1A and NTC1B isoforms in patients with IBM facilitate such objective. The non-invasive diagnostic methods, assays, devices, kits and systems are also useful for evaluating treatment effectiveness and also IBM prognosis and progression.

Accordingly, in one embodiment, provided herein is a method of diagnosing or detecting IBM in a patient in need thereof, the method comprising detecting the presence of autoantibodies that are reactive to at least a ~43 kDa protein from a muscle lysate sample or a mammalian cell lysate, the autoantibodies are from a blood sample of the patient. In one embodiment, a detectable presence of such autoantibodies indicates the likelihood of IBM in the patient.

In one embodiment, provided herein is a method for confirming IBM in a patient, the method comprising detecting the presence of autoantibodies binding to or are reactive to at least a ~43 kDa protein from a muscle lysate or a mammalian cell lysate. In one embodiment, the autoantibodies bind to or are reactive to at least a protein in a ~40-~60 kDa protein band from a blood sample of the patient having IBM in a 1D SDS PAGE gel. The autoantibodies are from a blood sample of the patient. In one embodiment, a detectable presence of such autoantibodies confirms the likelihood of IBM in the patient.

In one embodiment, provided is a method for identifying the likelihood of a patient having IBM comprising measuring a level of autoantibodies that are reactive to at least a ~43 kDa protein from a muscle lysate or a mammalian cell lysate, the autoantibodies are from a blood sample from the patient; and comparing the level of autoantibodies measured to a reference level, wherein the level of autoantibodies at least 5% over that of the reference level indicates that the patient is likely to have IBM. In another embodiment, a detectable presence of such autoantibodies confirms the likelihood of IBM in the patient.

In another embodiment, provided herein is a method for evaluating the efficacy of a treatment for a patient having IBM, the assay comprising measuring a level of autoantibodies that are reactive to at least a ~43 kDa protein from a muscle lysate or a mammalian cell lysate, the autoantibodies are from in at least two blood samples obtained from a patient at different times, wherein the different times are a first time point and a second time point, wherein the second time point is after the first time point, and wherein the patient has IBM and is being treated for IBM; and comparing the levels of the autoantibodies in the at least two blood samples, wherein a decrease in the level of the autoantibodies taken at the second time point compared to the first time point indicates that the treatment is effective, wherein an increase in the level of the autoantibodies taken at the second time point compared to the first time point or the levels are approximately the same indicates that the treatment is not effective, and wherein when the level of autoantibodies in the second time point decreases to below a detection limit indicates that treatment is effective and the patient is in remission.

In one embodiment of any method described herein, detecting the presence or measuring of autoantibodies targeting at least a ~43 kDa protein from a muscle lysate or a mammalian cell lysate comprising the steps of (a) contacting a blood sample from the patient with a muscle lysate or a mammalian cell lysate; (b) forming an antibody-protein complex between the autoantibody present in the blood sample and a protein from the muscle lysate or the mammalian cell lysate; (c) removing any unbound autoantibodies not in a complex with a protein from the muscle lysate or the mammalian cell lysate; (d) adding a detection antibody that is labeled and is reactive to an antibody from the blood sample; (e) removing any unbound labeled detection antibody; and (f) converting the label to a detectable signal, the detectable signal indicates the presence of autoantibodies against at least a ~43 kDa protein used in step (a).

In one embodiment, provided herein an assay for identifying the likelihood of a patient having IBM comprising measuring a level of autoantibodies reactive to a NT5C1A, a NT5C1B, or a peptide fragment thereof in a blood sample obtained from a patient in need thereof; and comparing the level of the autoantibodies in the blood sample with a reference level, wherein a detectable increase of at least 5% over that of the reference level indicates the likelihood of IBM.

In another embodiment, provided herein is an assay for evaluating the efficacy of a treatment for patient having IBM, the assay comprising measuring a level of autoantibodies reactive to a NT5C1A, or NT5C1B, or a peptide fragment thereof, or an isolated peptide, or a fusion protein described herein in at least two blood samples obtained from a patient at different times, wherein the different times are a first time point and a second time point, wherein the second time point is after the first time point, and wherein the patient has IBM and is being treated for IBM; and comparing the levels of the autoantibodies in at least two blood samples, wherein a decrease in the level of the autoantibodies taken at the second time point compared to the first time point indicates that the treatment is effective, wherein an increase in the level of the autoantibodies taken at the second time point compared to the first time point or the levels are approximately the same indicates that the treatment is not effective, and wherein when the level of autoantibodies in the second time point decreases to below a detection limit indicates that treatment is effective and the patient is in remission.

In one embodiment of any of the assays described herein, the level of reactive autoantibodies is measured by the steps comprising (a) contacting the blood sample from the patient with the NT5C1A, NT5C1B or a peptide fragment thereof, or an isolated peptide, or a fusion protein described herein; (b) forming an antibody-protein complex between the autoantibody present in the blood sample and the NT5C1A, NT5C1B or a peptide fragment, or an isolated peptide, or a fusion protein used in step (a) respectively; removing any unbound autoantibodies not in a complex with a protein or peptide; (c) adding a detection antibody that is labeled and is reactive to an antibody from the blood sample; (d) removing any unbound labeled detection antibody; and (e) converting the label to a detectable signal; a detectable signal indicates the presence of autoantibodies against the NT5C1A, NT5C1B, or a peptide fragment, or an isolated peptide, or a fusion protein used in step (a) respectively.

In one embodiment of any method or assay described herein, the patient presents symptoms of IBM, such as progressive muscle weakness, muscle pain and/or muscle fatigue. In one embodiment of any method or assay described herein, the PM, DM, other known autoimmune disorders has been rule out in the patient, i.e., confirming that the patient is not suffering from PM, DM, or Myasthenia gravis etc.

In one embodiment of any method or assay described herein, the patient is suspected of having IBM.

In one embodiment of any method or assay described herein, the method further comprising selecting a patient suspected of having IBM.

In one embodiment of any method or assay described herein, the patient is a human.

In one embodiment of any method described herein, the muscle lysate or mammalian cell lysate is derived from a human. In one embodiment, the mammalian cell lysate is HELA cell lysate.

In one embodiment of any of the assays described herein, the NT5C1B is selected from any one of the known isoforms of NT5C1B described herein.

In one embodiment of any of the assays described herein, the protein fragment of NT5C1A or NT5C1B comprises at least 6 contiguous amino acid residues and is not a full-length NT5C1A, a full-length NT5C1B polypeptide or isoforms thereof.

In one embodiment of any of the assays described herein, the protein fragment of NT5C1A or NT5C1B is an isolated peptide selected from the group consisting of AKIFYDN-LAPKKKPKSPKPQNAVTIAVSSRALFRMD (SEQ. ID. NO:6), RALFRMDEEQQIYTEQGVEEYVRYQLEHENEPFSPG (SEQ. ID. NO:7), SQLRVAFDGDAVLFSDESERIVKAHGLDRFFEHEKA (SEQ. ID. NO:8), KIRPHIFFDDQMFHVAGAQEMGTVAAHVPYGVAQTP (SEQ. ID. NO:9), HVAGAQEMGTVAAHVPYGVAQTPRRTAPAKQAPSAQ (SEQ. ID. NO:10), SQWSRISRSPSTKAPSIDEPRSRNTSAKLPSSSTSS (SEQ. ID. NO:11), DGDAVLFSDESEHFTKEHGLDKFFQYDTLCESKPLA (SEQ. ID. NO:12), DGDAVLFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), and HGLD(R/K)FF (SEQ. ID. NO:16).

In one embodiment of any of the assays described herein, the protein fragment of NT5C1A or NT5C1B is fused or conjugated to a heterologous protein (i.e., a non-NT5C1A or NT5C1B protein) to form a fusion or chimeric protein such that the fusion protein is not a full-length NT5C1A, a full-length NT5C1B polypeptide or isoforms thereof. In some embodiments, the protein fragment of NT5C1A or NT5C1B is fused to a polymer.

In one embodiment of any method or assay for efficacy evaluation described herein, the treatment is experimental.

In one embodiment of any method or assay for efficacy evaluation described herein, the second time point is at least one month after the start of treatment.

In one embodiment of any method or assay described herein, the IBM is idiopathic.

In one embodiment of any method or assay described herein, the muscle lysate, the mammalian cell lysate, the NT5C1A or the NT5C1B or the isoform thereof, or the peptide fragment thereof, or the isolated peptide, or the fusion protein used is deposited or immobilized on a solid support.

In one embodiment of any method or assay described herein, the support is in the format of a dipstick, a test strip, a latex bead, a microsphere or a multi-well plate.

In one embodiment of any method or assay described herein, the detection antibody is labeled by covalently linking to an enzyme, label with a fluorescent compound or metal, or label with a chemiluminescent compound.

In one embodiment of any method or assay described herein, the blood sample is a plasma or serum sample. In another embodiment of any method or assay described herein, the blood sample is human plasma or a human serum sample.

In one embodiment, provided herein is an isolated peptide derived from the sequence of a cytosolic 5'-nucleotidase 1A protein (NT5C1A), a cytosolic 5'-nucleotidase 1B protein (NT5C1B) or an isoform thereof, the isolated peptide is bound by autoantibodies in a blood sample of a patient having inclusion body myositis (IBM).

In one embodiment, provided is a fusion protein that comprises an isolated peptide described herein fused to a heterologous peptide or polypeptide, wherein the fusion protein is not a full-length NT5C1A, a full-length NT5C1B polypeptide or isoform thereof.

In one embodiment, the isolated peptide consists essentially of AKIFYDNLAPKKKPKSPKPQNAVTIAVSSRALFRMD (SEQ. ID. NO:6), RALFRMDEEQQIYTEQGVEEYVRYQLEHENEPFSPG (SEQ. ID. NO:7), SQLRVAFDGDAVLFSDESERIVKAHGLDRFFEHEKA (SEQ. ID. NO:8), KIRPHIFFDDQMFHVAGAQEMGTVAAHVPYGVAQTP (SEQ. ID. NO:9), HVAGAQEMGTVAAHVPYGVAQTPRRTAPAKQAPSAQ (SEQ. ID. NO:10), SQWSRISRSPSTKAPSIDEPRSRNTSAKLPSSSTSS (SEQ. ID. NO:11), DGDAVLFSDESEHFTKEHGLDKFFQYDTLCESKPLA (SEQ. ID. NO:12), DGDAVLFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), or HGLD(R/K)FF (SEQ. ID. NO:16).

In another embodiment, provided herein is a device for identifying the presence or a level of autoantibodies that are reactive to a NT5C1A, a NT5C1B or a peptide fragment thereof, or an isolated peptide, or a fusion protein described herein in a blood sample from a patient comprising at least a NT5C1A or NT5C1B or protein fragment thereof, and at least one solid support, wherein the NT5C1A or NT5C1B or protein fragment thereof is deposited on the support.

In one embodiment, the device further comprises a detection antibody, wherein the detection antibody is specific for the antibodies of the patient and the detection antibody produces a detectable signal.

In one embodiment of any device described herein, the device performs an assay in which an antibody-protein or antibody-peptide complex is formed, e.g., an immunological assay.

In one embodiment of any device described herein, the NT5C1A or NT5C1B, or protein fragment thereof is selected from the group consisting of human NTC1A (SEQ. ID. NO: 1); human isoforms of NTC1B (SEQ. ID. NOs: 2-5), AKIFYDNLAPKKKPKSPKPQNAVTIAVSSRALFRMD (SEQ. ID. NO:6), RALFRMDEEQQIYTEQGVEEYVRYQLEHENEPFSPG (SEQ. ID. NO:7), SQLRVAFDGDAVLFSDESERIVKAHGLDRFFEHEKA (SEQ. ID. NO:8), KIRPHIFFDDQMFHVAGAQEMGTVAAHVPYGVAQTP (SEQ. ID. NO:9), HVAGAQEMGTVAAHVPYGVAQTPRRTAPAKQAPSAQ (SEQ. ID. NO:10), SQWSRISRSPSTKAPSIDEPRSRNTSAKLPSSSTSS (SEQ. ID. NO:11), DGDAVLFSDESEHFTKEHGLDKFFQYDTLCESKPLA (SEQ. ID. NO:12), DGDAVLFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), and HGLD(R/K)FF (SEQ. ID. NO:16).

In one embodiment of any device described herein, the protein fragment of NT5C1A or NT5C1B is fused or conjugated to a heterologous protein (i.e., a non-NT5C1A or NT5C1B protein) to form a fusion or chimeric protein such that the fusion protein is not a full-length NT5C1A, a full-length NT5C1B polypeptide or isoforms thereof.

In one embodiment of any device described herein, the assay is a serological immunoassay.

In one embodiment, provided is a test kit comprising any one of a device described herein. In one embodiment, the kit further comprising at least one detection antibody and optionally at least an agent for developing a detectable signal from the detection antibody. The kits can further comprise tubes or any other collection device for blood sample. In one embodiment, the kit can optionally further comprise at least one diagram and/or instructions describing the interpretation of test results.

In another embodiment, provided herein is a system comprising a measuring module measuring autoantibody information comprising a detectable signal from an immunoassay indicating the presence or level of antibodies that are reactive to at least a ~43 kDa protein from a muscle lysate or a mammalian cell lysate in a blood sample obtained from a patient; a storage module configured to store data output from the measuring module; a comparison module adapted to compare the data stored on the storage module with a reference level, and to provide a retrieved content, and an output module for displaying the retrieved content for the user, wherein the retrieved content showing the presence of detectable amount of antibodies reactive against to at least a ~43 kDa protein from a muscle lysate or a mammalian cell lysate indicates that the patient has IBM or has a relapse of IBM.

In another embodiment, provided herein is a system comprising a measuring module measuring autoantibody information comprising a detectable signal from an immunoassay indicating the presence or level of antibodies that are reactive to a NT5C1A, NT5C1B or protein fragments from a blood sample obtained from a patient; a storage module configured to store data output from the measuring module; a comparison module adapted to compare the data stored on the storage module with a reference level, and to provide a retrieved content, and an output module for displaying the retrieved content for the user, wherein the retrieved content showing the presence of detectable amount of antibodies reactive against NT5C1A, NT5C1B or protein fragment indicates that the patient has IBM or has a relapse of IBM.

In another embodiment, provided herein is a system to evaluate the effectiveness of a treatment or to facilitate the prognosis evaluation of IBM in a patient, comprising a measuring module configured to receive and output autoantibody information from a blood sample obtained from a patient, wherein the autoantibodies information measures the level of auto antibodies that are reactive to at least a ~43 kDa protein from a muscle lysate or a mammalian cell lysate; a storage module configured to store output information from the measuring module; a comparison module adapted to compare the data stored on the storage module with a reference data, and to provide a comparison content, wherein the reference data comprises previous data from the same patient wherein the previous data had indicated detectable amounts of autoantibodies, and an output module for displaying the comparison content for the user, wherein if there is no detectable amount of autoantibodies reactive at least a ~43 kDa protein from a muscle lysate or a mammalian cell lysate, then the patient is in remission or if there is a reduction of at least 5% compared to a prior reading, then the treatment is effective in the patient.

In another embodiment, provided herein is a system to evaluate the effectiveness of a treatment or to facilitate the prognosis evaluation of IBM in a patient, comprising a measuring module configured to receive and output autoantibody information from a sample obtained from a patient, wherein the autoantibodies information measures the level of autoantibodies that are reactive to a NT5C1A or a NT5C1B or a protein fragment thereof, or an isolated peptide, or a fusion protein described herein; a storage module configured to store output information from the measuring module; a comparison module adapted to compare the data stored on the storage module with a reference data, and to provide a comparison content, wherein the reference data comprises previous data from the same patient wherein the previous data had indicated detectable amounts of autoantibodies, and an output module for displaying the comparison content for the user, wherein if there is no detectable amount of autoantibodies reactive against NT5C1A or a NT5C1B or a peptide fragment thereof, or an isolated peptide, or a fusion protein respectively, then the patient is in remission or if there is a reduction of at least 5% compared to a prior reading, then the treatment is effective in the patient.

In one embodiment, provided herein is a computer readable storage medium comprising: a storing data module containing data from a sample obtained from a subject that represents a signal level from an immunoassay for antibodies that are reactive to at least a ~43 kDa protein from a muscle lysate or a mammalian cell lysate, or a NT5C1A or a NT5C1B or a protein fragment thereof, or an isolated peptide, or a fusion protein described herein; a comparison module that compares the data stored on the storing data module with a reference data, and to provide a comparison content, and an output module displaying the comparison content for the user, wherein the presence of a detectable amount of antibodies reactive against the ~43 kDa protein from a muscle lysate or a mammalian cell lysate, or the NT5C1A or the NT5C1B or the protein fragment, or an isolated peptide, or a fusion protein described herein of at least 5% relative to the reference data indicates that the subject has IBM or has a relapse of IBM.

In one embodiment of any system, storage medium, method or assay described herein, the reference level comprises data from a population of non-IBM healthy individuals.

Definitions of Terms

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean ±1%.

The term "protein fragment" of a NTC1A or a NTC1B refers to any subject polypeptide or protein having an amino acid residue sequence shorter than that of a polypeptide whose amino acid residue sequence is described herein. A fragment of a NTC1A or a NTC1B is a shortened or truncated NTC1A or NTC1B proteins. The polypeptide can have N-terminus or C-terminus truncations and/or also internal deletions. In one embodiment, a protein fragment of a NTC1A or a NTC1B have about 50 or less contiguous amino acid residues. In some embodiments, protein fragments of a NTC1A or a NTC1B have about 40, 30 or 20 contiguous amino acid residues. In one embodiment, protein fragments of a NTC1A or a NTC1B have about 10 or less than contiguous amino acid residues. In one embodiment, the "protein fragment" of a NTC1A or a NTC1B is one that the autoantibodies from a blood sample of a patient having IBM reacts with, in other words, the "protein fragment" of a NTC1A or a NTC1B in an antigen of the autoantibodies from a blood sample of a patient having IBM. In one embodiment, the "protein fragment" of a NTC1A or a NTC1B is a peptide.

In one embodiment, a peptide of NTC1A or a NTC1B as used herein refer to a polymer of 50 or less contiguous amino acid residues derived from a full-length NTC1A or a NTC1B. In one embodiment, "peptide" and "protein fragment" are used interchangeably.

As used herein, the term "treat' or treatment" refers to reducing or alleviating at least one adverse effect or symptom associated with IBM. These include reducing the amount of autoantibodies against at least a ~43 kDa protein from a muscle lysate or a mammalian cell lysate, a NTC1A, a NTC1B protein, reducing, inhibiting or stopping the production of auto-antibodies against such proteins, suppression of the immune system, and reducing the inflammation and degradation/damage associated with the activities of the autoantibodies, progression of muscle weakness, muscle pain and fatigue. In one embodiment, treatment administered to the patient encompassed more than type or kind of treatment strategy or approach or target. For example, the treatment is a combination of immunosuppression by drug administration, a physical exercise therapy, a nutrition program and a gene or biologic therapy.

The term "subject" as used herein refers to a mammal. In another embodiment, the subject is a human. As used herein, the terms "subjects", "individuals" or "patients" are used interchangeably. A subject can be male or female.

The term "consisting of" refers to compositions, methods, and respective components thereof as described herein, which are exclusive of any element not recited in that description of the embodiment.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of elements that do not materially affect the basic and novel or functional characteristic(s) of that embodiment.

As used herein, the term "idiopathic IBM" is currently used to describe IBM that is not caused by any known etiology. In one embodiment, "idiopathic IBM" is not PM or DM.

As used herein, the term "autoantibodies" and "antibodies" against a 43 kDa protein in a muscle lysate or a mammalian cell lysate, or a NT5C1A or a NT5C1B are used interchangeably. Such antibodies are produced by a subject and in reactive to an endogenous protein in the subject. In one embodiment, the "autoantibodies" are antibodies reactive against a self-protein.

As used herein, the term "endogenous protein" is a protein encoded by the genome of the subject. In one embodiment, an "endogenous protein" is a self-protein with respect to the subject.

As used herein, the term "reactive" when used in the context of an antibody refers to the binding of the antibody with its antigen. For example, an anti-NTC1A antibody is reactive to NTC1A, the antibody's antigen. In one embodiment, an antibody is "reactive" to an antigen also means the antibody is targeted against that antigen.

The term "identity" here refers to the degree of relatedness between two or more protein sequences, which is determined by the match between these sequences. The percentage identity is obtained as the percentage of identical amino acids in two or more sequences taking account of gaps and other sequence features.

The terms "identical" or percent "identity", in the context of two or more polypeptide or protein sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical."

As used herein, an "isolated peptide" refers to a peptide that does not occur in the natural environment, and thus an "isolated peptide" is made "by the hand of man" from its components (i.e. the amino acid residues) or its full-length naturally occurring polypeptide.

As used herein, the term "fusion protein" or "fusion polypeptide" refers to a protein created by joining two genes or two proteins/peptides together. In the laboratory, this can be achieved through the creation of a fusion gene which is done through the removal of the stop codon from a DNA sequence of the first protein and then attaching the DNA sequence of the second protein in frame. The resulting DNA sequence will then be expressed by a cell as a single protein. In a fusion protein, the two proteins that will be joined together with a linker or spacer peptide added between the two proteins. This linker or spacer peptide often contain protease cleavage site to facilitate the separation of the two proteins after expression and purification The making of fusion protein as a technique is commonly used for the identification and purification of proteins through the fusion of a GST protein, FLAG peptide or a hexa-his peptide.

By "conjugated" is meant the covalent linkage of at least two molecules. As described herein, a NTC1A or NTC1B peptide is conjugated to a polymer or a solid support, a label (e.g., a latex bead or gold particles) or to a non-related (i.e., non-NTC1A or NTC1B peptide or protein).

The term "statistically significant" or "significantly" refers to statistical significance and generally means a two standard deviation (2SD) difference, above or below a reference value. Additional definitions are provided in the text of individual sections below.

The terms "increased" or "increase" means an increase of at least 5% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms "decrease," "reduce," "reduced", and "reduction" are all used herein generally to mean a decrease by at least 5% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment. In one embodiment, a "decrease" is the absence of autoantibodies as measured by the detection limit of an assay method for antibodies, e.g., ELISA or Western blot analysis.

As used herein, the "detection limit" of an assay method for antibodies is the background level of the signal produced by the assay method.

As used herein, an "effective" treatment for IBM is evaluated by a reduction of at least 5% of autoantibodies in the blood sample of a patient, the reduction is compared to a prior reading of autoantibodies in the blood sample of the same patient or to a reference level of such autoantibodies in the blood sample(s) of healthy subjects not having IBM. In other embodiments, the reduction can be at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of such autoantibodies detectable in the blood sample of the patient.

The term "antibody" is meant to be an immunoglobulin protein that is capable of binding an antigen. Antibody as used herein is meant to include antibody fragments, e.g. F(ab')2, Fab', Fab, capable of binding the antigen or antigenic fragment of interest.

The term "labeled antibody", as used herein, includes antibodies that are labeled by a detectable means and include, but are not limited to, antibodies that are enzymatically, radioactively, fluorescently, colorimetrically and chemiluminescently labeled. Antibodies can also be labeled with a detectable tag, such as c-Myc, HA, VSV-G, HSV, FLAG, V5, or HIS. The detection and quantification of an autoantibody present in a blood sample correlate to the intensity of the signal emitted from the detectably labeled antibody.

The term "label" refers to a composition capable of producing a detectable signal indicative of the presence of the target autoantibody present in a blood sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "agent" as used herein refers to a chemical entity or biological product, or combination of chemical entities or biological products, that are used in developing the detectable signal indicative of the presence of the target autoantibody present in a blood sample.

The term "support" refers to conventional supports such as beads, particles, dipsticks, fibers, filters, membranes and silane or silicate supports such as glass slides.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" can refer to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

BRIEF DESCRIPTION OF THE DRAWINGS

FIG. 2 shows the multiple alignment of four isoforms (SEQ ID NOS 2-5, respectively, in order of appearance) of the human cytosolic 5'-nucleotidase 1B (NT5C1B) protein.

FIGS. 3A (top view) and 3B (side view) are schematic diagrams of an exemplary test strip assay for determining the presence and/or level of autoantibodies in a fluid sample.

DETAILED DESCRIPTION

Figure 1:
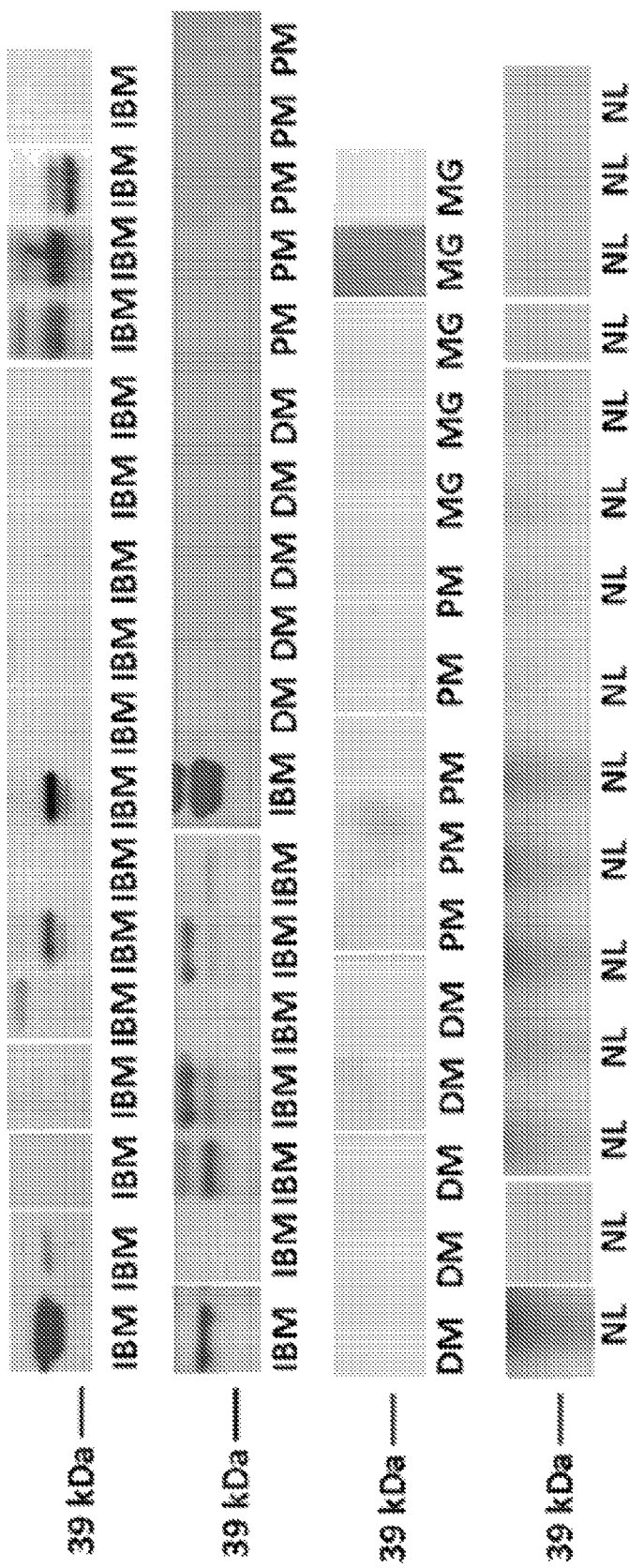
FIG. 1 are Western blots stowing the presence of circulating autoantibodies against a 43 kDa muscle protein in blood samples of patients having inclusion body myositis (IBM). Images from all immunoblots are shown. Reactivity is present in 13 of 25 different IBM plasma samples, but in none of 10 dermatomyositis (DM), 10 polymyositis (PM), 5 myasthenia gravis (MG) or 15 normal volunteer (NL) plasma samples.

Embodiments and all aspects of the technology described herein are based on the discovery of circulating autoantibodies that target specific muscle proteins in patients having IBM. These patients were definitively diagnosed with IBM by muscle tissue biopsies; their muscles have the classic appearance of vacuole-like holes in the muscles, deposits of abnormal proteins within the cells and presence of filamentous inclusions in the muscles. Alternatively, these patients were differential diagnosed whereby all other known possible causes of symptoms associated with IBM have been systematically ruled out.

The inventors found that IBM patients have autoantibodies that target at least a ~43 kilodalton (kDa) protein from a muscle sample in a Western blot analysis. Lysates of normal healthy human muscle sample was separated in a one-dimension sodium dodecyl sulfate polyacrylamide electrophoresis gel (SDS-PAGE gel) under denaturing conditions and electro-transferred to nitrocellulose membranes. The membranes were contacted with the plasma or serum of several IBM human patients and then processed for Western blot analyses. The blots revealed binding of autoantibodies in the human plasma to at least one ~43 kDa protein. The apparent molecular weight (MW) of the targeted muscle protein is estimated by way of a molecular size standard on the same SDS-PAGE gel under SDS denaturing conditions. Healthy patients free of any inflammation conditions and patients with other myositis, e.g., PM and DM, do not have any detectable autoantibodies targeting at least a ~43 kilodalton (kDa) protein from a muscle sample in a Western blot analysis under 1D SDS-PAGE conditions.

Proteins in the muscle lysate are naturally occurring proteins in a patient, i.e., they are endogenous proteins, and are considered to be self-proteins with respect to that patient. In fact all proteins expressed by the genome of the patient are also considered to be self-proteins with the exception of integrated viral genome in infected patients. The function of immune system in a patient is to protect the patient from foreign pathogens. In order to perform this function, the immune system must be able to distinguish self-proteins from foreign proteins; the cells of the immune system should not bind self-proteins and should only bind to foreign proteins from pathogens and other foreign particles. Therefore, in a normal healthy patient, there should not be any antibodies reactive to any muscle lysate or any self-protein. An antibody that targets, binds, and is reactive against a self-protein is an autoantibody.

Since the presence of autoantibodies targeting at least a ~43 kDa protein is found only in IBM patients and not in healthy subjects or patients with other myostits, detection of such autoantibodies can be useful for diagnosing, detecting and/or confirming IBM in a subject, especially when there is currently no easy, non-invasive method of diagnosing IBM except via the invasive method of a muscle biopsy.

Accordingly, in one embodiment, provided herein is a method of diagnosing or detecting IBM in a patient in need thereof, the method comprising detecting the presence of autoantibodies that are reactive to at least a ~43 kDa protein from a muscle lysate sample or a mammalian cell lysate, the autoantibodies are from a blood sample of the patient. In one embodiment, a detectable presence of such autoantibodies indicates the likelihood of IBM in the patient.

In one embodiment, provided herein is a method for confirming IBM in a patient, the method comprising detecting the presence of autoantibodies binding or are reactive to at least a ~43 kDa protein from a muscle lysate or a mammalian cell lysate. The autoantibodies are from a blood sample of the patient. In one embodiment, a detectable presence of such autoantibodies confirms the likelihood of IBM in the patient.

In one embodiment, provided is a method for identifying the likelihood of a patient having IBM comprising measuring a level of autoantibodies that are reactive to at least a ~43 kDa protein from a muscle lysate or a mammalian cell lysate, the autoantibodies are from a blood sample from the patient; and comparing the level of autoantibodies measured to a reference level, wherein the level of autoantibodies of at least 5% over that of the reference level indicates that the patient is likely to have IBM.

In another embodiment, provided herein is a method for evaluating the efficacy of a treatment for a patient having IBM, the assay comprising measuring a level of autoantibodies that are reactive to at least a ~43 kDa protein from a muscle lysate or a mammalian cell lysate in at least two blood samples obtained from a patient at different times, wherein the different times are a first time point and a second time point, wherein the second time point is after the first time point, and wherein the patient has IBM and is being treated for IBM; and comparing the levels of the autoantibodies in the at least two blood samples, wherein a decrease in the level of the autoantibodies taken at the second time point compared to the first time point indicates that the treatment is effective, wherein an increase in the level of the autoantibodies taken at the second time point compared to the first time point or the levels are approximately the same for both time points indicates that the treatment is not effective, and wherein when the level of autoantibodies in the second time point decreases to below a detection limit of the measuring assay method used indicates that the patient is in remission.

In some embodiments of any method described herein, other mammalian cell lysates can be substitute for the muscle lysate used. Example of other mammalian cell lysates includes HELA cell lysate.

In one embodiment of any method described herein, the detecting or measuring of autoantibodies targeting at least a ~43 kDa protein from a muscle lysate or a mammalian cell lysate comprises one dimension SDS-PAGE and Western blot analysis. In another embodiment of any method described herein, the detecting or measuring of autoantibodies comprises an enzyme-linked immunoadsorbent assay (ELISA).

In one embodiment of any method described herein, detecting the presence or measuring of autoantibodies targeting at least a ~43 kDa protein from a muscle lysate or a mammalian cell lysate comprising the steps of (a) contacting a blood sample from the patient with a muscle lysate or a mammalian cell lysate; (b) forming an antibody-protein complex between the autoantibody present in the blood sample and a protein from the muscle lysate or the mammalian cell lysate; (c) removing any unbound autoantibodies not in a complex with a protein from the muscle lysate or the mammalian cell lysate; (d) adding a detection antibody that is labeled and is reactive to an antibody from the blood sample; (e) removing unbound labeled detection antibody; and (f) converting the label to a detectable signal, the detectable signal indicates the presence of autoantibodies against at least a ~43 kDa protein used in step (a). For example, the detection antibody in reactive against human antibodies.

In one embodiment of any method described herein, the method further comprises separating the proteins in the muscle lysate or the mammalian cell lysate prior to contacting with the blood sample. In one embodiment of any method described herein, the muscle lysate or the mammalian cell lysate is separated by 1D SDS-PAGE; the proteins in the muscle lysate or the mammalian cell lysate are separated by size and/or charge during electrophoresis under denaturing conditions.

In one embodiment of any method described herein, the method further comprising depositing or immobilizing proteins of the muscle lysate or the mammalian cell lysate on a solid support prior to contacting with the blood sample. For example, the muscle lysate or the mammalian cell lysate is depositing or immobilized at the bottom of a multi-well plate, such as in ELISA assay plates. The support used can be in the format of a nitrocellulose membrane, a polyvinylidene fluoride membrane, a dipstick, a test strip, a latex bead, a microsphere or a multi-well plate. In one embodiment, non-specific interaction between the solid support and proteins in the lysate occurs such that the support is coated with some lysate protein. In one embodiment, a known amount of muscle lysate or mammalian cell lysate is deposited or immobilized to a solid support. The range of protein is between 0.1 ng-10 mg.

In one embodiment of any method described herein, the muscle lysate or the cell mammalian lysate is separated by 1D SDS-PAGE prior to contacting with the blood sample. In another embodiment of any method described herein, the proteins in muscle lysate or the cell mammalian lysate are separated by 1D SDS-PAGE and immobilized on a solid support prior to contacting with the blood sample.

In one embodiment of any method described herein, the muscle lysate or the mammalian cell lysate is derived from a mammal, e.g., human, monkey, rat, mouse, pig, horse, cat, dog etc. In one embodiment, the muscle lysate is a human muscle lysate. In another embodiment, the muscle lysate is derived from skeletal muscles. In another embodiment, the human muscle lysate is derived from skeletal muscles.

The inventors proceeded to identify at least one of the ~43 kDa protein from the human muscle lysate that were bound by autoantibodies in the plasma of IBM patients. The inventors found that IBM patients have autoantibodies that target two related proteins in the human skeletal muscles: a cytosolic 5'-nucleotidase 1A (NT5C1A) and a cytosolic 5'-nucleotidase 1B (NT5C1B), in Western blot analyses containing denatured human muscle proteins. Normal human muscle lysates were separated by 1D SDS-PAGE and electro transferred to nitrocellulose membranes. When these membranes were contacted with the plasma of patients with IBM in Western blot analysis, the plasma showed a selective immune-reactivity against a protein band having an apparent molecular weight (MW) of ~43 kDa on the 1D SDS-PAGE gel. This ~43 kDa protein band was excised and further analyzed by mass spectrometry. The inventors identified one ~43 kDa protein as NT5C1A in two separate methods described in Example 2 The estimated molecular weight of NT5C1A based on the predicted primary amino acid sequence is approximately 41 kDa. In addition to NT5C1A, the inventors also identified a related protein, NT5C1B. There are several isoforms of NT5C1B (MW ranging from ~45 kDa to ~69 kDa) and all isoforms have approximately 65% sequence identity to NT5C1A. The inventors also uncovered the sequences of specific peptides derived from NT5C1A and NT5C1B that were recognized by the autoantibodies of IBM patients. In other words, the autoantibodies from IBM patients bind these peptides. These peptides are AKIFYDNLAPKKKPKSPKPQNAVTIAVSSRALFRMD (SEQ. ID. NO:6), RALFRMDEEQQIYTEQGVEEYVRYQLEHENEPFSPG (SEQ. ID. NO:7), SQLRVAFDGDAV-LFSDESERIVKAHGLDRFFEHEKA (SEQ. ID. NO:8), KIRPHIFFDDQMFHVAGAQEMGTVAAHVPYGVAQTP (SEQ. ID. NO:9), HVAGAQEMGTVAAHVPYGVAQT-PRRTAPAKQAPSAQ (SEQ. ID. NO:10), SQWSRISRSP-STKAPSIDEPRSRNTSAKLPSSSTSS (SEQ. ID. NO:11), DGDAVLFSDESEHFTKEHGLDKFFQYDTLCESKPLA (SEQ. ID. NO:12), DGDAVLFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), and HGLD(R/K)FF (SEQ. ID. NO:16). Healthy subjects free of any inflammation conditions and patients with other myositis, e.g., PM and DM, do not have detectable autoantibodies that react, bind or target NT5C1A or NT5C1B.

NT5C1A or NT5C1B are naturally occurring proteins in a patient and are considered to be self-proteins with respect to that patient. The function of immune system in a patient is to protect the patient from foreign pathogens. In order to perform this function, the immune system must be able to distinguish self-proteins from foreign proteins; the cells of the immune system should not bind self-proteins and should only bind to foreign proteins from pathogens. Therefore, in a normal healthy patient, there should not be any antibodies reactive to NT5C1A or NT5C1B. An antibody that targets, binds, and is reactive against a self-protein is an autoantibody.

Since the presence of anti-NT5C1A and/or anti-NT5C1B autoantibodies is found only in IBM patients and not in healthy subjects or patients with other myositis, detection of anti-NT5C1A and/or anti-NT5C1B autoantibodies can be used to diagnose IBM, thereby providing an easily non-invasive method of diagnosing IBM in lieu of the invasive method of a muscle biopsy. Additionally, detection of anti-NT5C1A and/or anti-NT5C1B autoantibodies can be used to (1) verify whether myositis, muscle weakness and joint pain in a patient is due to autoantibodies immunoreactive to NT5C1A and/or NT5C1B; (2) confirm a suspected case of IBM before other symptoms occur or progress further; often IBM diagnosis occurs after many year of misdiagnosis; (3) determine whether symptoms of muscle weakness are caused by a known autoimmune disease or disorder, a muscle or a nerve problem; (4) differentiate between some types of myostits and myopathies such as PM, DM, dystrophies, and congenital myopathies; (5) follow the course (progression, remission, relapse or status quo) of IBM myositis in a patient during a treatment program; and (6) permit evaluation of the efficacy of a treatment for IBM.

While previous studies have reported an association between IBM and the presence of various autoantibodies, thus suggesting an autoimmune process in IBM, none have been identified as disease specific (13) and their prevalence is less than that seen with DM and PM. (3, 14, 15, 16 and 17). In a review of 99 patients with sporadic IBM, 43 (44%) had elevated titers of one or more of nine different non disease-specific autoantibodies. (13) While 8 of 16 (50%) of the IBM patients tested here for autoantibodies where positive for ANA, there was no co-relationship between this positivity and the presence of 43 kDa autoreactivity.

It should be noted that the detection of anti-NT5C1A and/or anti-NT5C1B autoantibodies or autoantibodies against at least a ~43 kDa protein in muscle lysates from a blood sample of patients with IBM have a sensitive of 50% and a specificity of 100%. Current serological diagnostic tests for PM and DM, e.g., anti-Jo antibodies, have a sensitivity of about ~20% and a specificity of less than 50%. This mean that the current serological tests for PM and DM under diagnose about 80% of the time. Accordingly, compared to the serological diagnostics available for PM and DM, the non-invasive diagnostic methods and assays described herein are at least greater sensitivity and specificity at detecting IBM.

Accordingly, a simple blood sample can be used to test for and detect autoantibodies reactive against at least a ~43 kDa protein from a muscle cell lysate or a mammalian cell lysate or reactive against a NTC1A, or NTC1B, or protein fragments thereof. Such a method would be highly favorable over the current diagnostic method of a muscle tissue biopsy which is an invasive technique. In one embodiment, the autoantibodies can be detected by an immunoassay wherein an antibody-protein complex is formed. In one embodiment, the immunoassay is a serological immunoassay.

Accordingly, in one embodiment, provided herein an assay for identifying the likelihood of a patient having IBM comprising measuring a level of autoantibodies that are reactive to a NT5C1A, a NT5C1B, or a peptide fragment thereof, or an isolated peptide, or a fusion protein described herein, the autoantibodies are from a blood sample obtained from a patient in need thereof; and comparing the level of the autoantibodies in the blood sample with a reference level, wherein a detectable increase of at least 5% over that of the reference level indicates the likelihood of IBM.

In another embodiment, provided herein is an assay for evaluating the efficacy of a treatment for patient having IBM, the assay comprising measuring a level of autoantibodies reactive to a NT5C1A, NT5C1B, or a peptide fragment thereof, or an isolated peptide, or a fusion protein described herein in at least two blood samples obtained from a patient at different times, wherein the different times are a first time point and a second time point, wherein the second time point is after the first time point, and wherein the patient has IBM and is being treated for IBM; and comparing the levels of the autoantibodies in the at least two blood samples, wherein a decrease in the level of the autoantibodies taken at the second time point compared to the first time point indicates that the treatment is effective, wherein an increase in the level of the autoantibodies taken at the second time point compared to the first time point or the levels are approximately the same at both time points indicates that the treatment is not effective, and wherein when the level of autoantibodies in the second time point decreases to below a detection limit indicates that the treatment is effective and the patient is in remission.

In one embodiment of any of the assays described herein, the level of reactive autoantibodies is measured by Western blot analysis or ELISA.

In one embodiment of any of the assays described herein, the level of reactive autoantibodies is measured by the steps comprising (a) contacting the blood sample from the patient with the NT5C1A, NT5C1B or peptide fragment thereof, or an isolated peptide, or a fusion protein described herein; (b) forming an antibody-protein complex between the autoantibody present in the blood sample and the NT5C1A, NT5C1B or peptide fragment or an isolated peptide, or a fusion protein used in step (a) respectively; removing any unbound autoantibodies not in a complex with a protein or peptide; (c) adding a detection antibody that is labeled and is reactive to an antibody from the blood sample; (d) removing any unbound labeled detection antibody; and (e) converting the label to a detectable signal; a detectable signal indicates the presence of autoantibodies against the NT5C1A, NT5C1B, or peptide fragment, or an isolated peptide, or a fusion protein used in step (a).

In one embodiment of any method or assay described herein, the patient presents symptoms of IBM, such as progressive muscle weakness, muscle pain and/or muscle fatigue. In one embodiment of any method or assay described herein, the PM, DM, other known autoimmune disorders has been rule out in the patient.

In one embodiment of any method or assay described herein, the method further comprising selecting a patient suspected of having IBM. In one embodiment, the patient suspected of having IBM presents at least one symptom known to be associated with IBM. In another embodiment, the patient presents skeletal muscle pain and/or muscle fatigue. In another embodiment, the patient presents skeletal muscle weakness. A skilled physician can evaluate with basic muscle strength test known in the art.

In one embodiment of any method or assay described herein, the patient is a human. In one embodiment, the patient is a human over 40 years old. In another embodiment, the patient is a human over 50 years old. In one embodiment, the human patient is male. In one embodiment, the human patient is male and over 40 years old. In one embodiment, the human patient is female and over 40 years old.

In one embodiment of any of the assays described herein, the NT5C1B is selected from any one of the known isoforms of NT5C1B described herein. In one embodiment of any of the assays described herein, the use of peptide fragments of the various isoforms of NT5C1B described herein are contemplated. In another embodiment of any of the assays described herein, the use of peptide fragments of NT5C1A is also contemplated. Similarly, in other embodiments of any of the assays described herein, the use of isolated peptides derived from NTC1A or NTC1B and isoforms thereof, or a fusion protein comprising a peptide derived from NTC1A or NTC1B and isoforms thereof described herein are contemplated.

In one embodiment of any of the assays described herein, the protein fragment of NT5C1A or NT5C1B comprises at least 6 contiguous amino acid residues and is not a full-length NT5C1A, a full-length NT5C1B polypeptide or isoforms thereof.

In one embodiment of any of the assays described herein, the protein fragment of NT5C1A or NT5C1B used is an isolated peptide selected from the group consisting of AKIFYDNLAPKKKPKSPKPQNAVTIAVSSRALFRMD (SEQ. ID. NO:6), RALFRMDEEQQIYTEQGVEEYVRYQLEHENEPFSPG (SEQ. ID. NO:7), SQLRVAFDGDAVLFSDESERIVKAHGLDRFFEHEKA (SEQ. ID. NO:8), KIRPHIFFDDQMFHVAGAQEMGTVAAHVPYGVAQTP (SEQ. ID. NO:9), HVAGAQEMGTVAAHVPYGVAQTPRRTAPAKQAPSAQ (SEQ. ID. NO:10), SQWSRISRSPSTKAPSIDEPRSRNTSAKLPSSSTSS (SEQ. ID. NO:11), DGDAVLFSDESEHFTKEHGLDKFFQYDTLCESKPLA (SEQ. ID. NO:12), DGDAVLFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), and HGLD(R/K)FF (SEQ. ID. NO:16).

In one embodiment of any method or assay for evaluating efficacy, the treatment is experimental. Currently, there is no known effective treatment for IBM. In one embodiment, an effective treatment for IBM would at the minimum encompass reducing the level of autoantibodies to at least a ~43 kDa protein from a muscle lysate, or a mammalian cell lysate, or NT5C1A or the NT5C1B, or a peptide fragment, or an isolated peptide, or a fusion protein described herein thereof. In another embodiment, an effective treatment for IBM would at the minimum encompass reducing at least one symptom known to be associated with IBM, e.g., muscle pain or weakness.

In one embodiment of any method or assay for evaluating efficacy, the first time point is prior to any treatment. In another embodiment of the method or assay for evaluating efficacy, the first time point is after the start of at least one treatment. In some embodiments, more than one type of treatment is administered concurrently to the patient.

In one embodiment of any method or assay for evaluating efficacy, the second time point is at least one month after the start of at least one treatment. In another embodiment of any method or assay for evaluating efficacy, the second time point is at least one month after the first time point and both the first time point and the second time point are after the start of at least one treatment. In some embodiments, a third and fourth sample time points are performed. In any embodiment, the comparison is always between the data of a later time point with the data of an earlier time point, the earlier time point can be the immediate prior time point of the later time point.

In one embodiment of any method or assay for evaluating treatment efficacy, the level of the antibodies can be detected by an immunoassay wherein an antibody-protein complex is formed. The subject has initially been evaluated with symptoms consistent with IBM and has a detectable amount of autoantibodies against at least a ~43 kDa protein from a muscle lysate, or a mammalian cell lysate, or NT5C1A or the NT5C1B, or the peptide fragment thereof, or an isolated peptide, or a fusion protein described herein. Upon treatment, for example, with novel immunosuppressive therapy or other experimental treatment, over time, there is a decrease in the amount of detectable autoantibodies against at least a ~43 kDa protein from a muscle lysate, or a mammalian cell lysate, or detectable autoantibodies against NT5C1A or the NT5C1B, or the peptide fragment thereof. In an ideal case, the amount of autoantibodies should fall below the detectable level of the detection/measuring methods described herein and the subject is deemed to be in remission for IBM. A decrease in the level of autoantibodies in the second time point compared to the first time point (or a later time point compared to an earlier time point) is at least 5%, at least 5%, at least 20%, at least 30%, at least 40%, at least 50%, at least 60%, at least 70%, at least 80%, at least 90%, 100% and all the percentages between 10-100% drop in the titer of autoantibodies. In one embodiment, below the detection limit is when the level of antibodies is reduced to between 95-100% or more compared to the first time point when the subject was initially evaluated with symptoms consistent with IBM, tested positive for autoantibodies against at least a ~43 kDa protein from a muscle lysate, or a mammalian cell lysate, or a NT5C1A or NT5C1B, or a peptide fragment thereof, or an isolated peptide, or a fusion protein described herein, and no treatment has been administered to the subject. The assay methods used for measuring the levels of autoantibodies are identical for all the samples collected at different time points from the subject. Decreasing titer of auto antibodies indicate that the treatment is effective in the subject.

In other embodiments, there is no decrease in the level of antibodies in the second time point compared to the first time point. Instead, there can be an increase or a stable level of antibodies.

In one embodiment, there is an increase in antibody level in the second time point compared to the first time point and the first time point has no detectable auto-antibodies. This indicates that the patient has relapsed and the IBM has recurred.

In one embodiment, there is an increase in antibody level in the second time point compared to the first time point and the first time point has detectable autoantibodies. This indicates worsening of the disease and/or lack of efficacious treatment. The increase is at least 5%, at least 10%, at least 20%, at least 30%, at least 50% at least 100%, at least 200%, at least 300%, at least 500%, at least 1000%, or more and including all the percentages between 10-1000%.

In one embodiment, there is a stable level of autoantibody, wherein the auto-antibodies detectable at the second and first time points are comparably similar within statistical analysis variances or deviation, about 1%, 2%, 3%, 4%, 5% and all the percentages between 1%-5% standard deviation from the level of auto-antibodies from the first time point. The stable level of autoantibody indicates stable disease, wherein the treatment has been of insufficient duration (i.e., that it should be continued if clinically indicated) or is ineffective.

In one embodiment of any method or assay described herein, the IBM is idiopathic prior to the present discovery. Idiopathic IBM arises spontaneously or is from an obscure or unknown cause. In one embodiment of any method or assay described herein, the patient has not have a muscle biopsy performed.

In one embodiment of any method or assay described herein, the blood sample is a plasma or serum sample. Methods of preparing of plasma or serum from a blood sample are known in the art. A skill artisan can obtained the plasma or serum by any method known in the art, e.g., by centrifugation of a blood sample in the presence of an anti-coagulant to obtain plasma.

The inventor showed that there was no autoantibody reactive against at least a ~43 kDa protein from a muscle lysate detected for the blood samples of healthy subjects free of any inflammation conditions. There was also no such autoantibody detectable in patients with other myositis by way of Western blot analysis. Accordingly, in one embodiment of any methods and assays described herein, the reference level is the detection limit of the assay used to measure the level of antibody binding to the at least a ~43 kDa protein from a muscle lysate or a mammalian cell lysate, or the NT5C1A or the NT5C1B, or the peptide fragment thereof, or an isolated peptide, or a fusion protein described herein. Accordingly, in one embodiment of any method or assay described herein, a level of autoantibodies above the detection limit of an immunological assay method used indicates the likelihood that the patient has IBM. As shown in Example 1, the reference level is the detection limit of a Western blot analysis. A level of autoantibodies above this detection limit of a Western blot analysis indicates the likelihood that the patient has IBM. It is assumed that the reagents and conditions of the immunological assay method used for the patient and the reference levels are kept the same. Similarly for the methods for evaluating treatment efficacy, the assays for measuring the levels of autoantibodies at the various time points are the same. As another example, if the immunological assay is an ELISA, then the reference level is the detection limit of an ELISA. A level of autoantibodies above this detection limit of an ELISA indicates the likelihood that the patient has IBM.

In one embodiment of any method or assay described herein, the reference level is the level of autoantibodies binding to at least a ~43 kDa protein from a muscle lysate or a mammalian cell lysates in a blood sample of a healthy subject free of any inflammation conditions. In another embodiment of any method or assay described herein, the reference level is the level of autoantibodies binding to the NT5C1A or the NT5C1B, or the peptide fragment thereof, or an isolated peptide, or a fusion protein described herein in a blood sample of a healthy subject free of any inflammation conditions.

In one embodiment, the amount of anti-NTC1A, anti-NTC1B or anti-~43 kDa protein autoantibodies in a healthy non-IBM individual or a population of healthy non-IBM individuals as determined by conventional ELISA or Western blot set forth in Example 1 can be considered as the background or reference level. The collected blood sample, e.g., sera or plasma, from the healthy non-IBM individuals are diluted 1:100 and used in Western blot analysis. The intensity of visible bands on the blots is quantified by densitometry. From this densitometry data, the average value and the one order of standard deviation are computed.

In one embodiment, the reference level is the average level obtained for a population of healthy subject free of any inflammation conditions. The following is an example for obtaining a reference level from a population of 25 healthy human subjects and should not be construed as limited to this example and methodology. Blood samples are taken from 25 healthy human subjects. The blood samples are measured for the level of autoantibodies binding to at least a ~43 kDa protein from a muscle lysate or a mammalian cell lysate, or NT5C1A or the NT5C1B, or the peptide fragment thereof, or an isolated peptide, or a fusion protein described herein. The levels of autoantibodies can be measured by a number of immunological assay methods known in the art, e.g., quantitative Western blots and ELISA. The levels obtained for these 25 subjects are then added together and averaged, giving an average reference level. The size of the population from which the average reference level is obtained can vary anywhere from 3 to 100 or more, e.g., 500 subjects. The statistics, the average value and one order of standard deviation can be uploaded to the computer system and data storage media described herein.

The method of measuring the levels of autoantibodies in the patient with or suspected of having IBM and the method of measuring the levels of autoantibodies in the healthy patient should the same. For example, if the level of autoantibodies in the patient's blood was measured by ELISA, then the reference level used for comparison is that obtained by ELISA. Patients having at least 5% more than this average amount of anti-NTC1A, anti-NTC1B or anti-~43 kDa protein autoantibodies is likely to have IBM, especially if the patient is also presents the clinical features of the disease, e.g. progressive muscle weakness, pain and fatigue.

In one embodiment of any method or assay described herein, the NT5C1A or the NT5C1B or the isoform thereof, or the peptide fragment thereof, or an isolated peptide, or a fusion protein described herein is deposited or immobilized on a solid support. The support can be in the format of a dipstick, a test strip, a latex bead, a microsphere or a multi-well plate. In one embodiment, a known amount of a muscle lysate, a mammalian cell lysate, a NT5C1A or a NT5C1B or an isoform thereof, or the peptide fragment thereof, or an isolated peptide, or a fusion protein described herein is deposited or coupled to a solid support. The range of protein is between 0.1 ng-10 mg.

In one embodiment of any method or assay described herein, the support is in the format of a dipstick, a test strip, a latex bead, a microsphere or a multi-well plate. Any solid support can be used, including but not limited to, nitrocellulose, solid organic polymers, such as polystyrene, or laminated dipsticks such as described in U.S. Pat. Nos. 5,550,375 and 5,656,448, which is specifically incorporated herein by reference in their entirety.

In one embodiment of any method or assay described herein, the detection antibody is labeled by covalently linking to an enzyme, label with a fluorescent compound or metal, label with gold or latex, or label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid.

In one embodiment, the detection antibody is specifically reactive only to the specie of the patient. For example, if the patient is a human, then the detection antibody is an anti-human antibody.

In one embodiment of any assay described herein, more than one of NT5C1A, NT5C1B, isoforms thereof, peptide fragment thereof, or an isolated peptide, or a fusion protein described herein can be used. For example, a collection of several NT5C1A and/or NT5C1B peptide fragments or isolated peptides are used. For example, any combinations of AKIFYDNLAPKKKPKSPKPQNAVTIAVSSRAL-FRMD (SEQ. ID. NO:6), RALFRMDEEQQIYTE-QGVEEYVRYQLEHENEPFSPG (SEQ. ID. NO:7), SQL-RVAFDGDAVLFSDESERIVKAHGLDRFFEHEKA (SEQ. ID. NO:8), KIRPHIFFDDQMFHVAGAQEMGT-VAAHVPYGVAQTP (SEQ. ID. NO:9), HVAGAQEMGT-VAAHVPYGVAQTPRRTAPAKQAPSAQ (SEQ. ID. NO:10), SQWSRISRSPSTKAPSIDEPRSRNTSAK-LPSSSTSS (SEQ. ID. NO:11), DGDAVLFSDESEHFTKE-HGLDKFFQYDTLCESKPLA (SEQ. ID. NO:12), DGDAV-LFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), and HGLD(R/K)FF (SEQ. ID. NO:16) can be used for the assays described herein. For example, any combination of several NT5C1A and/or NT5C1B peptide fragments can be deposited or immobilized on a solid support.

In one embodiment of any assay described herein, the several NT5C1A and/or NT5C1B peptide fragments or isolated peptides used are covalently linked. For example, DGDAVLFSDESERIVKAHGLDRFF (SEQ. ID. NO:13) is covalently linked to KIRPHIFFDDQMFHVAGAQEMGT-VAAHVPYGVAQTP (SEQ. ID. NO:9) forming a dimer of peptide fragments. In one embodiment of any assay described herein, the several NT5C1A and/or NT5C1B peptide fragments used are covalently linked together forming dimers, trimmers and other multimers. In one embodiment of any assay described herein, the dimers, trimmers and other multimers of several NT5C1A and/or NT5C1B peptide fragments used are deposited or immobilized on a solid support.

NTC1A, NTC1B, Isoforms of NTC1B and Peptides

The human cytosolic 5'-nucleotidase 1A (EC=3.1.3.5) is an enzyme that dephosphorylates the 5' and 2'(3')-phosphates of deoxyribonucleotides and has a broad substrate specificity. The enzyme helps to regulate adenosine levels in heart during ischemia and hypoxia. It is highly expressed in skeletal muscle and has been detected at intermediate levels in heart, brain, kidney and pancreas. The full-length NTC1A polypeptide has 368 amino acid residues. Alternate names of NTC1A include cN-1A, cN1A, and cN-1. The UNIPRO- TEIN identifier for NTC1A is Q9BXI3. The GENBANK™ Accession number NTC1A is NP_115915.1. (SEQ. ID. NO:1).

MEPGQPREPQEPREPGPGAETAAAPVWEEAKIFYDNLAPKKKPKSPKPQNA
VTIAVSSRALFRMDEEQQIYTEQGVEEYVRYQLEHENEPFSPGPAFPFVKA
LEAVNRRLRELYPDSEDVFDIVLMTNNHAQVGVRLINSINHYDLFIERFCM
TGGNSPICYLKAYHTNLYLSADAEKVREAIDEGIAAATIFSPSRDVVVSQS
QLRVAFDGDAVLFSDESERIVKAHGLDRFFEHEKAHENKPLAQGPLKGFLE
ALGRLQKKFYSKGLRLECPIRTYLVTARSAASSGARALKTLRSWGLETDEA
LFLAGAPKGPLLEKIRPHIFFDDQMFHVAGAQEMGTVAAHVPYGVAQTPRR
TAPAKQAPSAQ

The human cytosolic 5'-nucleotidase 1B (EC=3.1.3.5) is an enzyme related to NTC1A. There are at least four isoforms of NTC1B and they are the result of alternate splicing of the primary transcript. The isoforms have about 65% identity to NTC1A Like NTC1A, NTC1B dephosphorylates the 5' and 2'(3')-phosphates of deoxyribonucleotides and helps to regulate adenosine levels. It is highly expressed in testis, placenta and pancreas, and is also detected at lower levels in heart, kidney, liver and lung. Alternate names of NTC1B include autoimmune infertility-related protein, cN1B, cN-1B, AIRP and FKSG85.

Alternative splicing of the human NTC1B gene produces several isoforms, 1-5. UNIPROTEIN identifiers for the isoforms 1-4 are Q96P26-1 (SEQ. ID. NO:2), Q96P26-2 (SEQ. ID. NO:2), Q96P26-2 (SEQ. ID. NO:3), and Q96P26-4 (SEQ. ID. NO:4) respectively. GENBANK Accession numbers of the isoforms are NP_001002006, NP_001186015.1, NP_001186016.1, NP_001186017.1, NP_001186033.1, NP_001002006.1, NM_001002006.2 and NP_150278.2. Alignments of four isoforms Q96P26 1-4 are shown in FIG. 2.

Q96P26-1
(SEQ. ID. NO: 2)
MSQTSLKQKKNEPGMRSSKESLEAEKRKESDKTGVRLSNQMRRAVNPNHSL
RCCPFQGHSSCRRCLCAAEGTALGPCHTIRIYIHMCLLWEQGQQITMMRGS
QESSLRKTDSRGYLVRSQWSRISRSPSTKAPSIDEPRSRNTSAKLPSSSTS
SRTPSTSPSLHDSSPPPLSGQPSLQPPASPQLPRSLDSRPPTPPEPDPGSR
RSTKMQENPEAWAQGIVREIRQTRDSQPLEYSRTSPTEWKSSSQRRGIYPA
STQLDRNSLSEQQQQQREDEDDYEAAYWASMRSFYEKNPSCSRPWPPKPKN
AITIALSSCALFNMVDGRKIYEQEGLEKYMEYQLTNENVILTPGPAFRFVK
ALQYVNARLRDLYPDEQDLFDIVLMTNNHAQVGVRLINSVNHYGLLIDRFC
LTGGKDPIGYLKAYLTNLYIAADSEKVQEAIQEGIASATMFDGAKDMAYCD
TQLRVAFDGDAVLFSDESEHFTKEHGLDKFFQYDTLCESKPLAQGPLKGFL
EDLGRLQKKFYAKNERLLCPIRTYLVTARSAASSGARVLKTLRRWGLEIDE
ALFLAGAPKSPILVKIRPHIFFDDHMFHIEGAQRLGSIAAYGFNKKFSS

Q96P26-2
(SEQ. ID. NO: 3)
MSQTSLKQKKNEPGMRSSKESLEAEKRKESDKTGVRLSNQGSQESSLRKTD
SRGYLVRSQWSRISRSPSTKAPSIDEPRSRNTSAKLPSSSTSSRTPSTSPS
LHDSSPPPLSGQPSLQPPASPQLPRSLDSRPPTPPEPDPGSRRSTKMQENP
EAWAQGIVREIRQTRDSQPLEYSRTSPTEWKSSSQRRGIYPASTQLDRNSL
SEQQQQQREDEDDYEAAYWASMRSFYEKNPSCSRPWPPKPKNAITIALSSC
ALFNMVDGRKIYEQEGLEKYMEYQLTNENVILTPGPAFRFVKALQYVNARL
RDLYPDEQDLFDIVLMTNNHAQVGVRLINSVNHYGLLIDRFCLTGGKDPIG
YLKAYLTNLYIAADSEKVQEAIQEGIASATMFDGAKDMAYCDTQLRVAFDG
DAVLFSDESEHFTKEHGLDKFFQYDTLCESKPLAQGPLKGFLEDLGRLQKK
FYAKNERLLCPIRTYLVTARSAASSGARVLKTLRRWGLEIDEALFLAGAPK
SPILVKIRPHIFFDDHMFHIEGAQRLGSIAAYGFNKKFSS

Q96P26-3
(SEQ. ID. NO: 4)
MQENPEAWAQGIVREIRQTRDSQPLEYSRTSPTEWKSSSQRRGIYPASTQL
DRNSLSEQQQQQREDEDDYEAAYWASMRSFYEKNPSCSRPWPPKPKNAITI
ALSSCALFNMVDGRKIYEQEGLEKYMEYQLTNENVILTPGPAFRFVKALQY
VNARLRDLYPDEQDLFDIVLMTNNHAQVGVRLINSVNHYGLLIDRFCLTGG
KDPIGYLKAYLTNLYIAADSEKVQEAIQEGIASATMFDGAKDMAYCDTQLR
VAFDGDAVLFSDESEHFTKEHGLDKFFQYDTLCESKPLAQGPLKGFLEDLG
RLQKKFYAKNERLLCPIRTYLVTARSAASSGARVLKTLRRWGLEIDEALFL
AGAPKSPILVKIRPHIFFDDHMFHIEGAQRLGSIAAYGFNKKFSS

Q96P26-4
(SEQ. ID. NO: 5)
MSQTSLKQKKNEPGMRSSKESLEAEKRKESDKTGVRLSNQMRRAVNPNHSL
RCCPFQGHSSCRRCLCAAEGTALGPCHTIRIYIHMCLLWEQGQQITMMRGS
QESSLRKTDSRGYLVRSQWSRISRSPSTKAPSIDEPRSRNTSAKLPSSSTS
SRTPSTSPSLHDSSPPPLSGQPSLQPPASPQLPRSLDSRPPTPPEPDPGSR
RSTKMQENPEAWAQGIVREIRQTRDSQPLEYSRTSPTEWKSSSQRRGIYPA
STQLDRNSLSEQQQQQREDEDDYEAAYWASMRSFYEKNPSCSRPWPPKPKN
AITIALSSCALFNMVDGRKIYEQEGLEKYMEYQLTNENVILTPGPAFRFVK
ALQYVNARLRDLYPDEQDLFDIVLMTNNHAQVGVRLINSVNHYGLLIDRFC
LTGGKDPIGYLKAYLTNLYIAADSEKVQEAIQEGIASATMFDGAKDMAYCD
TQLRVAFDGDAVLFSDESEHFTKEHGLDKFFQYDTLCESKPLAQGPLKGFL
EDLGRLQKKFYAKNERLLCPIRTYLVTARSAASSGARVLKTLRRWGLEIDE
ALFLAGAPKSPILVKIRPHIFFDDHMFHIEGAQRKSLGWMS

In one embodiment, the NTC1A and NTC1B are mammalian proteins. In one embodiment, the NTC1A and NTC1B are human NTC1A and human NTC1B.

In one embodiment, provided herein is an isolated peptide derived from the sequence of a cytosolic 5'-nucleotidase 1A protein (NT5C1A), a cytosolic 5'-nucleotidase 1B protein (NT5C1B) or an isoform thereof, the isolated peptide is bound by autoantibodies in a blood sample of a patient having inclusion body myositis (IBM). One characteristic of the peptide is its binding to autoantibodies from a blood sample e.g., plasma or serum, from a patient having IBM. In one embodiment, the patient is one who has had a muscle biopsy performed to definitively confirm the presence of IBM. In another embodiment, the patient is one who has all the symptoms known associated with IBM and also have all other known possible causes systematically ruled out.

In one embodiment, the NT5C1A, NT5C1B or isoforms thereof is derived from a mammal. In one embodiment, the NT5C1A, NT5C1B or isoforms thereof is derived from a human.

In one embodiment, the patient is a human.

Such isolated peptides are useful for detecting autoantibodies in a blood sample of a patient suspected of having IBM. Such isolated peptides are useful for the development of non-invasive diagnosis or detection assays, devices, systems and kits for IBM.

In one embodiment, the isolated peptide comprises at least 6 contiguous amino acid residues and is not a full-length NT5C1A, a full-length NT5C1B polypeptide or isoforms thereof. The 6 amino acid residues are consecutive, reflecting what is encoded and expressed in the intact full length NT5C1A polypeptide, a full-length NT5C1B polypeptide or isoforms thereof. In another embodiment, the isolated peptide that binds autoantibodies from a patient having IBM comprises no more than 50 amino acids of NT5C1A, NT5C1B polypeptide or isoforms thereof. In yet another embodiment, the isolated peptide comprises at least 7, 8, 9, 10, 11, 12, 13, 14, 15, 16, 17, 18, 19, 20, 21, 22, 23, 24, 25, 26, 27, 28, 29, or 30 consecutive amino acid residues of NT5C1A, NT5C1B polypeptide or isoforms thereof. In another embodiment, the isolated peptide has no more than 30 consecutive amino acid residues. In yet another embodiment, the isolated peptide has no more than 29, 28, 27, 26, 25, 24, 23, 22, 21, 20, 19, 18, 17, 16, 15, 14, 13, 12, 11, 10, 9, 8, or 7 consecutive amino acid residues of NT5C1A, NT5C1B polypeptide or isoforms thereof. In another embodiment, the isolated peptide has 50 or fewer consecutive amino acids and includes peptides with 49, 48, 47, 46, 45, 44, 43, 42, 41, 40, 39, 38, 37, 36, 35, 34, 33, 32, 31, and 30 consecutive amino acids of NT5C1A, NT5C1B polypeptide or isoforms thereof.

In one embodiment, the isolated peptide is selected from the group consisting of AKIFYDNLAPKKKPKSPKPQ-NAVTIAVSSRALFRMD (SEQ. ID. NO:6), RALFRMDE-EQQIYTEQGVEEYVRYQLEHENEPFSPG (SEQ. ID. NO:7), SQLRVAFDGDAVLFSDESERIVKAHGLDRFFE-HEKA (SEQ. ID. NO:8), KIRPHIFFDDQMFHVA-GAQEMGTVAAHVPYGVAQTP (SEQ. ID. NO:9), HVA-GAQEMGTVAAHVPYGVAQTPRRTAPAKQAPSAQ (SEQ. ID. NO:10), SQWSRISRSPSTKAPSIDEPRSRNT-SAKLPSSSTSS (SEQ. ID. NO:11), DGDAVLFSDESEH-FTKEHGLDKFFQYDTLCESKPLA (SEQ. ID. NO:12), DGDAVLFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), and HGLD(R/K)FF (SEQ. ID. NO:16).

The isolated peptide described herein can be made by any method known in the art. For example, by recombination molecular biology methods, by synthetic chemical synthesis, or protein fragmentation or cleavage of a full-length NT5C1A, a full-length NT5C1B polypeptide or isoforms thereof. Protein fragmentation of a full-length protein can be achieved by limited enzymatic digestion, e.g., by trypsin, endoproteinase GluC or chymotrypsin etc. Peptides synthesis methods are described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and is exemplified by the disclosure of U.S. Pat. No. 4,105,603. Classical solution synthesis is described in detail in "Methoden der Organischen Chemic (Houben-Weyl): Synthese von Peptiden", E. Wunsch (editor) (1974) Georg Thieme Verlag, Stuttgart West Germany.

The fragment condensation method of synthesis is exemplified in U.S. Pat. No. 3,972,859. Other available syntheses are exemplified in U.S. Pat. No. 3,842,067, U.S. Pat. No. 3,872,925, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego, #9830). The foregoing disclosures are incorporated herein by reference. Recombinant techniques are well known to those skilled in the art. Representative methods are disclosed in Maniatis, et al., Molecular cloning, a Laboratory Manual, 2nd edition, Cold Springs Harbor Laboratory (1989), incorporated herein by reference.

In one embodiment, the isolated peptide is placed, deposited, immobilzed or conjugated to a solid support. The support is in the format of a dipstick, a test strip, a latex bead, a microsphere or a multi-well plate.

In one embodiment, the isolated peptide is covalently linking to a label, e.g., with a fluorescent compound or metal, with latex that can be colored, with biotin, with proteins, with enzymes, or with a chemiluminescent compound. The following are only exemplary and should not be construed as limited to these. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1, 3-benzene disulphonic acid.

In one embodiment, the isolated peptide comprises at least one conservative amino acid substitution and substantially retains immunoreactivity with autoantibodies in the blood sample of a patient having IBM. In one embodiment, the isolated peptide comprises at least one conservative amino acid substitution and no more than five conservative amino acid substitutions, and substantially retains immunoreactivity with autoantibodies in the plasma of a patient having IBM. The immunoreactivity with autoantibodies in the plasma of a patient having IBM can be tested by any method known in the art, e.g., by dot blots, peptide gel Western analysis or by ELISA.

As used herein, the phrase "substantially retains immunoreactivity with autoantibodies" when used in reference with an isolated peptide having conservative amino acid substitutions means that the autoantibodies described herein would still bind, recognize and react with such isolated peptide comprising at least one conservative amino acid substitution. The bind, recognize and react (ie., the immunological antigenic reaction of the autoantibody) is retained and can be ascertained by the known immunological assays described herein. In one embodiment, the conservative amino acid substitution does not destroy the antigenic epitope recognized the autoantibodies. In one embodiment, the isolated peptide comprises two, three, four or five conservative amino acid substitutions and also substantially retains immunoreactivity with autoantibodies described herein.

The conservative amino acid substitution variant of isolated peptides of NTC1A or NTC1B are still recognized and bound by autoantibodies from a blood sample of a patient having IBM. Conservative amino acid residue substitution is well known in the art. Conservative amino acid substitutions replace an amino acid with another amino acid of similar chemical structure. Examples of such substitution are glycine for alanine, leucine for valine, serine for threonine, and aspartate for glutamate. For example, GDAVLFSDESE (SEQ. ID. NO:17) can be altered to a peptide GEAVLFSDESE (SEQ. ID. NO:18), GDAVLFSDDSD (SEQ. ID. NO:19), or GDAALFSDESE (SEQ. ID. NO:20), or GDAALFSDESD (SEQ. ID. NO:21). In one embodiment, only one of the amino acids is substituted with a conservative substitution. In another embodiment, two substitutions can be made. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Conservative amino acid substitutions do not change the overall structure of the peptide nor the type of amino acid side chains available for forming van der Waals bonds with a binding partner. Conservative amino acid substitution can be achieved during chemical synthesis of the peptide by adding the desired substitute amino acid at the appropriate sequence in the synthesis process. Alternatively, molecular biology methods can be used. The coding sequence of a peptide described herein can be made by annealing two single strand nucleic acids that are complementary to each other. Alternatively, site-directed mutagenesis can be used for conservative amino acid substitution in the peptides described herein. Methods of chemical peptide synthesis, molecular biology methods for production of peptides, and site-directed mutagenesis are known in the art.

In one embodiment, the isolated peptide described herein is fused to a heterologous peptide or polypeptide forming a fusion or chimeric protein, wherein the fusion protein is not a full-length NT5C1A a full-length NT5C1B polypeptide or isoform thereof.

As used herein, the term "heterologous peptide or polypeptide" refers the polymer of amino acid residue that are not naturally associated or are part of the NTC1A or NTC1B protein as encoded by the genome.

In one embodiment, provided is a fusion protein that comprises an isolated peptide described herein fused to a heterologous peptide or polypeptide, wherein the fusion protein is not a full-length NT5C1A, a full-length NT5C1B polypeptide or isoform thereof. The fusion protein is formed by the fusion of a peptide described herein with another heterologous protein or a portion thereof. The heterologous protein is any protein that is not a member of the NTC1A or NTC1B family. The fusion gives rise to a NTC1A or NTC1B chimeric polypeptide. Such fusion proteins comprising NTC1A or NTC1B peptides described herein can serve to facilitate protein expression, solubility during expression, and purification, e.g. thioredoxin, glutathione S-transferase, avidin and six histidine tags.

In certain embodiments, the isolated peptide described herein are dimerized or multimerized by covalent attachment to at least one linker moiety. The linker moiety can be, although not necessarily, a C1-12 linking moiety optionally terminated with one or two —NH— linkages and optionally substituted at one or more available carbon atoms with a lower alkyl substituent. Another the linker can comprise —NH—R—NH— wherein R is a lower (C1-6) alkylene substituted with a functional group, such as a carboxyl group or an amino group, that enables binding to another molecular moiety (e.g., as may be present on the surface of a solid support during peptide synthesis or to a pharmacokinetic-modifying agent such as PEG). In certain embodiments the linker is a lysine residue. In certain other embodiments, the linker bridges the C-termini of two peptide monomers, by simultaneous attachment to the C-terminal amino acid of each monomer. In other embodiments, the linker bridges the peptides by attaching to the side chains of amino acids not at the C-termini. When the linker attaches to a side chain of an amino acid not at the C-termini of the peptides, the side chain preferably contains an amine, such as those found in lysine, and the linker contains two or more carboxy groups capable of forming an amide bond with the peptides.

The isolated peptide described herein may be oligomerized using the biotin/streptavidin system. Oligomerization can enhance one or more activities of peptides as described herein. Biotinylated analogs of peptide monomers may be synthesized by standard techniques known to those skilled in the art. For example, the peptide monomers may be C-terminally biotinylated. These biotinylated monomers are then oligomerized by incubation with streptavidin (e.g., at a 4:1 molar ratio at room temperature in phosphate buffered saline (PBS) or HEPES-buffered RPMI medium for 1 hour). In a variation of this process, biotinylated peptide monomers may be oligomerized by incubation with any one of a number of commercially available anti-biotin antibodies, e.g., goat anti-biotin.

In some embodiments, the isolated peptides described herein can be linked physically in tandem to form a polymer of NTC1A or NTC1B peptides. The isolated peptides making up such a polymer can be spaced apart from each other by a peptide linker. A "peptide linker" is a short (e.g., about 1-40, e.g., 1-20 amino acids) sequence of amino acids that is not part of the NTC1A or NTC1B or variant sequence. A linker peptide is attached on its amino-terminal end to one polypeptide or polypeptide domain and on its carboxyl-terminal end to another polypeptide or polypeptide domain. Examples of useful linker peptides include, but are not limited to, glycine polymers ((G)n) including glycine-serine and glycine-alanine polymers (e.g., a (Gly4Ser)n repeat where n=1-8 (SEQ ID NO: 22), preferably, n=3, 4, 5, or 6). The NTC1A or NTC1B peptides described herein can also be joined by chemical bond linkages, such as linkages by disulfide bonds or by chemical bridges. Molecular biology techniques that are well known to those skilled in the art can be used to create a polymer of NTC1A or NTC1B peptides. In one embodiment, combination of a NTC1A or NTC1B peptide and variant peptide is found in the polymer. Isolated peptide sequences described can also be linked together using non-peptide cross-linkers (Pierce 2003-2004 Applications Handbook and Catalog, Chapter 6) or other scaffolds such as HPMA, polydextran, polysaccharides, ethyleneglycol, poly-ethylene-glycol, glycerol, sugars, and sugar alcohols (e.g. sorbitol, mannitol).

Other examples of linking moiety known in the art include but are not limited to polyethylene glycol (PEG), mPEG-SPA-NHS or mPEG-NPC (Nektar Therapeutics, San Carlos Calif.), a linker molecule containing two carboxylic acids such as: —CO—$(CH_2)_n$-uX—$(CH_2)_m$-CO— where n is an integer between zero and 10, m is an integer between one and 10, X is selected from O, S, $N(CH_2)pNR1$, NCO $(CH_2)pNR1$, and CHNR1, R1 is selected from H, Boc (tert-butyloxycarbonyl), Cbz, and p is an integer between 1 and 10; the linker having the structure —NH—R—NH— wherein R is a lower (C1-6) alkyl substituted with a functional group such as a carboxyl group or an amino group that enables binding to another molecular moiety; For example, the linker may be a lysine (K) residue or a lysine amide (K—NH$_2$, a lysine residue wherein the carboxyl group has been converted to an amide moiety —CONH$_2$). Methods of conjugation are well known in the art, for example, P. E. Thorpe, et. al, 1978, Nature 271, 752-755; Harokopakis E., et. al., 1995, Journal of Immunological Methods, 185:31-42; S. F. Atkinson, et. al., 2001, J. Biol. Chem., 276:27930-27935; and U.S. Pat. Nos. 5,601,825, 5,180,816, 6,423,685, 6,706,252, 6,884,780, and 7,022,673, which are hereby incorporated by reference in their entirety.

Inclusion Body Myositis (IBM)

The inflammatory myopathies are autoimmune diseases of skeletal muscle, and consist of three major subtypes: dermatomyositis (DM), polymyositis (PM), and inclusion body myositis (IBM). Circulating autoantibodies have been detected in DM and PM (reviewed in (1)) and sought in IBM (2); however, none have been reported as prominently present in, or specific to, IBM (3). Since 1984, IBM has been believed to be a cytotoxic T-cell mediated disease with no humoral autoimmunity (4). Microarray studies reported in 2001, surprisingly showed that the most abundantly present transcripts in IBM muscle samples compared to normal muscle were immunoglobulin transcripts, unique to the B cell lineage (5, 6). This finding led to the demonstration in IBM muscle of abundant plasma cells (7) with immunoglobulin gene rearrangements characteristic of clonal expansion in response to local antigen stimulation (8), and the presence of a permissive environment for ectopic lymphoid structures suggestive of local maturation of B cells in muscle (9).

Aspects of the technology described herein relate to the diagnosis, prognosis, and treatment efficacy evaluation of IBM. As used herein, "inclusion body myositis" or "IBM" refers to an inflammatory myopathy in which the muscle cells of the subject comprise inclusion bodies. Methods of differential diagnosis of IBM include evaluating the following: age (typically >30 years); duration of illness (typically >6 months, mostly over months or years); gender (typically males >females 2:1); signs and symptoms of progressive muscle weakness; and an assortment of laboratory tests. In general, the clinical evaluation would include, but is not limited to, physical examination, measurement of electrical activity in the muscles of the subject (e.g. a nerve conduction test or an electromyogram (EMG)), a muscle biopsy (e.g. to look for signs of inflammation, muscle fiber death, vascular deformities and/or inclusion bodies), ultrasound to look for muscle inflammation, magnetic resonance imaging to reveal abnormal muscle and evaluate muscle disease, antibody tests, and a family history. IBM primarily affects men over the age of 50 but can affect younger subjects and women. Symptoms of IBM that can be useful in making a diagnosis of IBM include, but are not limited to, muscle weakness, muscle atrophy, or pain; falling and tripping, difficulty swallowing (dysphagia) occurs in approximately half of IBM cases.

In some embodiments, muscle weakness can begin in the wrists, fingers, and quadriceps; weakness of the swallowing muscles can occur. In some embodiments, IBM can be distinguished from other inflammatory myopathies (e.g. PM and DM) by the subject having normal or only mildly elevated creatine kinase levels in the bloodstream, whereas subjects with PM or DM typically have extremely elevated levels of creatine kinase. In some embodiments, IBM can also be distinguished from PM and DM by determining that the heart and lung muscles are not affected.

A number of serological testing are performed to exclude other conditions that affects muscles. Detailed testing of the antinuclear antibodies (ANA), when present, is important in identifying other overlap syndromes, most often those with another autoimmune disorder. About 30% of patients have myositis-specific autoantibodies: antibodies to aminoacyl-tRNA synthetases (anti-synthetase antibodies), including anti-Jo-1; antibodies to signal recognition particle (SRP—anti-SRP antibodies); and antibodies to Mi-2, a nuclear helicase. The relationship between these autoantibodies and disease pathogenesis remains unclear, although antibody to Jo-1 is a significant marker for fibrosing alveolitis, pulmonary fibrosis, arthritis, and Raynaud's syndrome.

Factors which can put a subject at risk for developing IBM include, but are not limited to, infection with a virus, e.g. the HIV virus, the HTLV-1 virus, or the Coxsackie B virus; exposure to certain drugs (e.g. carticaine, penicillamine, interferon-alpha, cimetidine, carbimazole, phenyloin, growth hormone, and the vaccine for hepatitis B), and a family history of IBM.

Current treatments for IBM are primarily aimed at symptomatic relief and support of musculature. These treatments are limited in effectiveness and they include, without being limited to, immunosupressives, corticosteroids, and supportive treatment for symptoms. Supportive treatment for symptoms includes, but is not limited to physical therapy, exercise, heat therapy (e.g. microwave and ultrasound), orthotics and assistive devices, and rest.

Devices and Kits

In another embodiment, provided herein is a device for identifying the presence of a level of antibodies that are reactive to a NT5C1A, a NT5C1B, a peptide fragment thereof, or an isolated peptide, or a fusion protein described herein in a blood sample from a patient, the device comprises at least a NT5C1A or NT5C1B or protein fragment thereof, or an isolated peptide, or a fusion protein described herein, and at least one solid support, wherein the NT5C1A or NT5C1B or protein fragment thereof, or an isolated peptide, or a fusion protein described herein is deposited on the support.

In one embodiment, the NT5C1A or NT5C1B or protein fragment thereof, or an isolated peptide, or a fusion protein that is deposited on the solid support or is immobilized on the support. In one embodiment, the NT5C1A or NT5C1B or protein fragment thereof, or an isolated peptide, or a fusion protein described herein is a human NT5C1A or NT5C1B protein or protein fragment thereof. In one embodiment, the solid support is in the format of a dipstick, a test strip, a latex bead, a microsphere or a multi-well plate.

In one embodiment, the blood sample from the subject is a serum or a plasma sample.

In one embodiment of any device described herein, the device performs an immunoassay wherein an antibody-protein or antibody-peptide complex is formed. In one embodiment of any device described herein, the immunoassay. In one embodiment, the immunoassay is a serological immunoassay.

In one embodiment of any device described herein, the device is a LFIA test strip.

In one embodiment of any device described herein, the NT5C1A or NT5C1B, or protein fragment thereof, or an isolated peptide, or a fusion protein described herein is selected from the group consisting AKIFYDNLAPKKKPK-SPKPQNAVTIAVSSRALFRMD (SEQ. ID. NO:6), RAL-FRMDEEQQIYTEQGVEEYVRYQLEHENEPFSPG (SEQ. ID. NO:7), SQLRVAFDGDAVLFSDESERIVKAH-GLDRFFEHEKA (SEQ. ID. NO:8), KIRPHIFFDDQMF-HVAGAQEMGTVAAHVPYGVAQTP (SEQ. ID. NO:9), HVAGAQEMGTVAAHVPYGVAQTPRRTAPAKQAP-SAQ (SEQ. ID. NO:10), SQWSRISRSPSTKAPSIDEPRS- RNTSAKLPSSSTSS (SEQ. ID. NO:11), DGDAVLFSDESEHFTKEHGLDKFFQYDTLCESKPLA (SEQ. ID. NO:12), DGDAVLFSDESERIVKAHGLDRFF (SEQ. ID. NO:13), DGDAVLFSDESEHFTKEHGLDKFF (SEQ. ID. NO:14), GDAVLFSDESE (SEQ. ID. NO:15), and HGLD(R/K)FF (SEQ. ID. NO:16).

In some aspects, the devices described herein facilitate the diagnosis of IBM in a subject. The devices facilitate the detection of an amount of autoantibodies that are reactive to NT5C1A or NT5C1B, or protein fragment thereof, or an isolated peptide, or a fusion protein described herein. The detection is by way of producing a detectable signal. A detectable signal indicates likelihood of IBM in the subject.

In one embodiment of any device described herein comprises at least one solid support. Any solid support can be used, including but not limited to, nitrocellulose membrane, nylon membrane, solid organic polymers, such as polystyrene, or laminated dipsticks such as described in U.S. Pat. No. 5,550,375. The use of "dip sticks" or test strips and other solid supports have been described in the art in the context of an immunoassay for a number of antigens. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. The "dip stick" technology can be easily adapted for the embodiments described herein by one skilled in the art. In embodiments of the devices described herein, the antigen for the autoantibody is a NT5C1A or NT5C1B, or protein fragment thereof, or an isolated peptide, or a fusion protein described herein. The antigen is deposited on the support and the autoantibody is detected by any method known in the art, e.g., by a detection antibody. In one embodiment, the device described herein further comprises a detection antibody. In one embodiment, the detection antibody is detectably labeled.

In one embodiment, provided herein are kits that comprise devices described herein and at least one detection antibody, wherein the detection antibody is specific for the autoantibodies that are reactive to a NT5C1A or NT5C1B, or protein fragment thereof, or an isolated peptide, or a fusion protein described herein, the autoantibodies being in a blood sample of a subject. In one embodiment of the kit, the detection antibody is labeled. In one embodiment, the detection antibody produces a detectable signal. For example, if the autoantibodies are from a subject that is a human, the detection antibody is anti-human antibody. In one embodiment, the kit can include a second labeled NT5C1A or NT5C1B, or protein fragment thereof, or an isolated peptide, or a fusion protein described herein, the label produces a detectable signal Diagnostic kits for carrying out the methods described herein are produced in a number of ways. In one embodiment, the diagnostic kit comprises (a) at least one of a NT5C1A or a NT5C1B, or protein fragment thereof, or an isolated peptide, or a fusion protein described herein, the protein or peptide or fusion protein may or may not be conjugated to a solid support and (b) a detection antibody conjugated to a detectable group. In one embodiment, the diagnostic kit further comprises other reagent(s). The reagents include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. Alternatively, a test kit contains (a) a control antibody that reacts against the NT5C1A or NT5C1B, or protein fragment thereof, or the isolated peptide, or the fusion protein supplied with the kit, and (b) an additional detection antibody conjugated to a detectable group.

The test kit may be packaged in any suitable manner, typically with all elements in a single container, optionally with a sheet of printed instructions for carrying out the test.

In one embodiment of the kit described herein, the kit comprises LFIA test strips.

In one embodiment of the kit described herein, the kit further comprises at least an agent or substrate for producing a detectable signal from the detection antibody.

Examples of kits include but are not limited to ELISA assay kits, and kits comprising test strips and dipsticks. In an ELISA kit, an excess amount of NT5C1A or NT5C1B, or protein fragment thereof is immobilized on a solid support. A sample containing an unknown amount of autoantibodies to NT5C1A or NT5C1B, or protein fragment thereof, or an isolated peptide, or a fusion protein described herein is added to the immobilized antigen, resulting in the formation of a complex consisting of the protein and the antibody. The complex is detected by a labeled second antibody that is specific for an antibody from the patient, e.g., a detection antibody is specific for human antibodies and the patient is a human. The amount of label detected is a measure of the amount of autoantibody present in the blood sample (see example 4).

In some embodiments of the kits described herein, the kit comprises a test strip (e.g., a LFIA test strip) or a dipstick.

In some embodiments of the kits described herein, the labeled detection antibodies are detectably labeled by enzyme labeling, fluorescent labeling, biotin labeling or radioisotope labeling. Other labels include but are not limited to colloidal gold and latex beads. The latex beads can also be colored. Methods of labeling antibodies are known in the art, for example, as described in "Colloidal Gold. Principles. Methods and Applications", Hayat M A (ed.) (1989-91). Vols 1-3, Academic press, London; in "Techniques in Immunocytochemistry", Bullock G R and Petrusz P (eds) (1982-90) Vols 1, 2, 3, and 4, Academic Press, London; in "Principles of Biological Microtechnique", Baker J R (1970), Methuen, London; Lillie R D (1965), Histopathologic Technique and practical Histochemistry, 3rd ed, McGraw Hill, New York; Berryman M A, et al (1992), J. Histochem Cytochem 40, 6, 845-857, all of which are incorporated hereby reference in their entirety.

In a typical colloidal gold labeling technique, the unique red color of the accumulated gold label, when observed by lateral or transverse flow along a membrane on which an antigen is captured by an immobilized antibody, or by observation of the red color intensity in solution, provides an extremely sensitive method for detecting sub nanogram quantities of proteins in solution. A colloidal gold conjugate consists of a suspension of gold particles coated with a selected protein or macromolecule (such as an antibody or antibody-based moiety). The gold particles may be manufactured to any chosen size from 1-250 nm. This gold probe detection system, when incubated with a specific target, such as in a tissue section, will reveal the target through the visibility of the gold particles themselves. For detection by eye, gold particles will also reveal immobilized antigen on a solid phase such as a blotting membrane through the accumulated red color of the gold sol. Silver enhancement of this gold precipitate also gives further sensitivity of detection. Suppliers of colloidal gold reagents for labeling are available from SPI-MARK™. Polystyrene latex Bead size 200 nm colored latex bead coated with antibody SIGMA ALDRICH®, Molecular Probes, Bangs Laboratory Inc., and AGILENT® Technologies.

In other embodiments of the kits described herein, at least one of the labeled detection antibodies is an enzyme-labeled antibody. The anti-NT5C1A or NT5C1B antibody that is bound and captured by the immobilized NT5C1A or NT5C1B, or protein fragment thereof, or an isolated peptide, or a fusion protein described herein on the solid support (e.g. microtiter plate wells) is identified by adding a chromogenic substrate for the enzyme conjugated to the labeled detection antibody, e.g. anti-human IgG, and color production detected by an optical device such as an ELISA plate reader.

Other detection systems can also be used, for example, a biotin-streptavidin system. Quantification is determined using a streptavidin-peroxidase conjugate and a chromagenic substrate. Such streptavidin peroxidase detection kits are commercially available, e.g., from DAKO; Carpinteria, Calif.

Detection antibodies and NT5C1A or NT5C1B, or protein fragment thereof can alternatively be labeled. For example, labeling can be achieved with any of a number of fluorescent compounds such as fluorescein isothiocyanate, europium, lucifer yellow, rhodamine B isothiocyanate (Wood, P. In: Principles and Practice of Immunoassay, Stockton Press, New York, pages 365-392 (1991)) for use in immunoassays. In conjunction with the known techniques for separation of antibody-antigen complexes, these fluorophores can be used to quantify the level of autoantibodies. The same applies to chemiluminescent immunoassay in which case antibody or desired antigen can be labeled with isoluminol or acridinium esters (Krodel, E. et al., In: Bioluminescence and Chemiluminescence: Current Status, John Wiley and Sons Inc. New York, pp 107-110 (1991); Weeks, I. et al., Clin. Chem., 29:1480-1483 (1983)). Radioimmunoassay (Kashyap, M. L. et al., J. Clin. Invest., 60:171-180 (1977)) is another technique in which detection antibody can be used after labeling with a radioactive isotope such as $^{125}$I. Some of these immunoassays can be easily automated by the use of appropriate instruments such as the IMX™ (Abbott, Irving, Tex.) for a fluorescent immunoassay and Ciba Coming ACS 180™ (Ciba Corning, Medfield, Mass.) for a chemiluminescent immunoassay.

In some embodiments, the kits described herein further comprise standards of known amounts of NT5C1A or NT5C1B, or protein fragment thereof, or an isolated peptide, or a fusion protein described herein. In some embodiments, these standards of known amounts are deposited or immobilized on a solid support to form a calibration or titration standard devices for comparison with the device used with test samples. In one embodiment, the kit comprises calibration or titration standard devices having known amounts of antigen of the autoantibody of interest. For example, calibration or titration standard devices are strips with 0 ng, 0.5 ng, 1 ng, 2.5 ng, 5 ng, 10 ng, 20 ng, and 50 ng of antigen deposited or immobilized on a solid support.

In some embodiments, the kits described herein further comprise reference values of the levels of anti-NT5C1A or NT5C1B, or protein fragment thereof antibodies. The reference values are average levels of anti-NT5C1A or NT5C1B, or protein fragment thereof antibodies in samples from a population of non-IBM healthy humans. Reference values can be provided as numerical values, or as standards of known amounts or titer of anti-NT5C1A or NT5C1B, or protein fragment thereof antibodies presented in pg/ml-g/ml.

In some embodiments, the kits described herein further comprise at least one sample collection container for sample collection. Collection devices and container include but are not limited to syringes, lancets, BD VACUTAINER® blood collection tubes.

In some embodiments, the kits described herein further comprise instructions for using the kit and interpretation of results. For example, a chart showing FIG. 4 interpretation of results.

Figure 5:
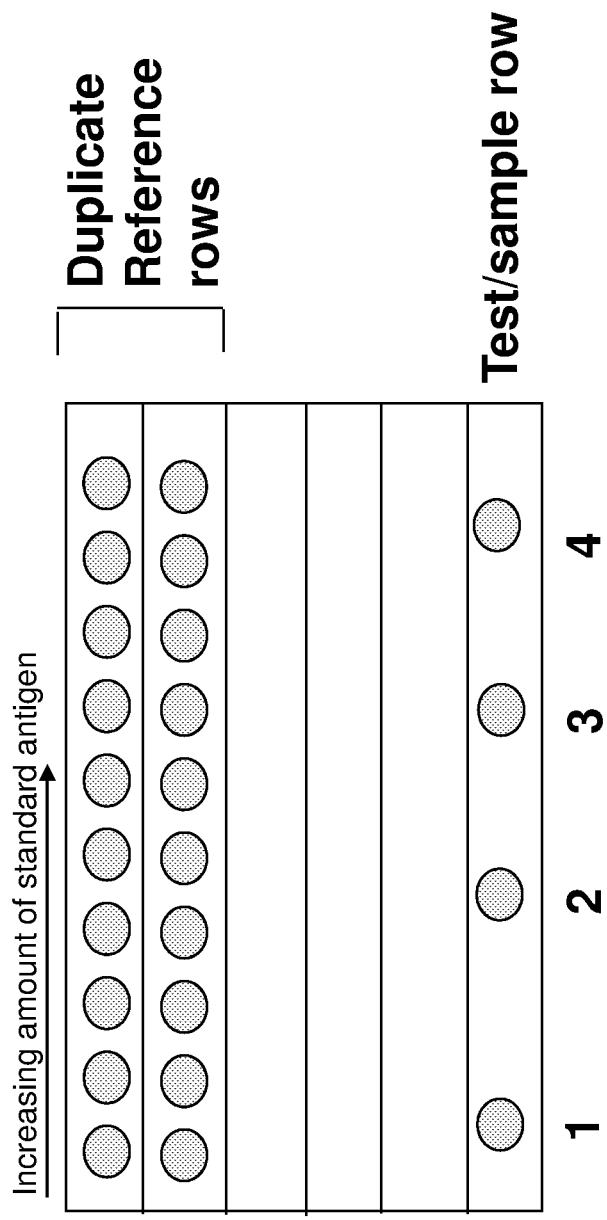
FIG. 5 is a schematic diagram of an exemplary ELISA plate assay comprising sample test wells and reference wells, the reference wells for generating standard titration curves.
Figure 6:
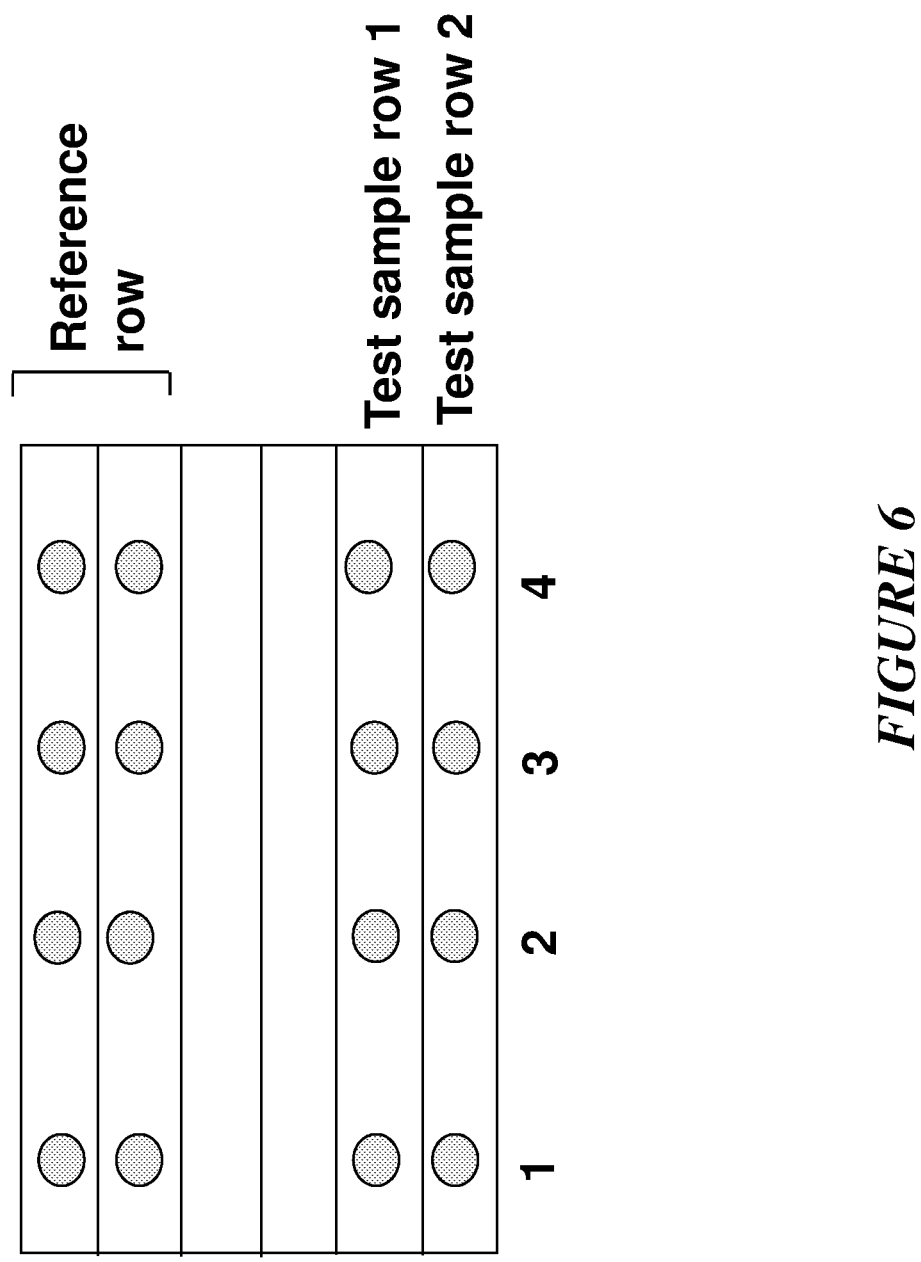
FIG. 6 shows a schematic diagram of another exemplary ELISA plate assay utilizing fixed amounts of standard NT5C1A or NT5C1B or peptide or fusion protein.
Figure 7:
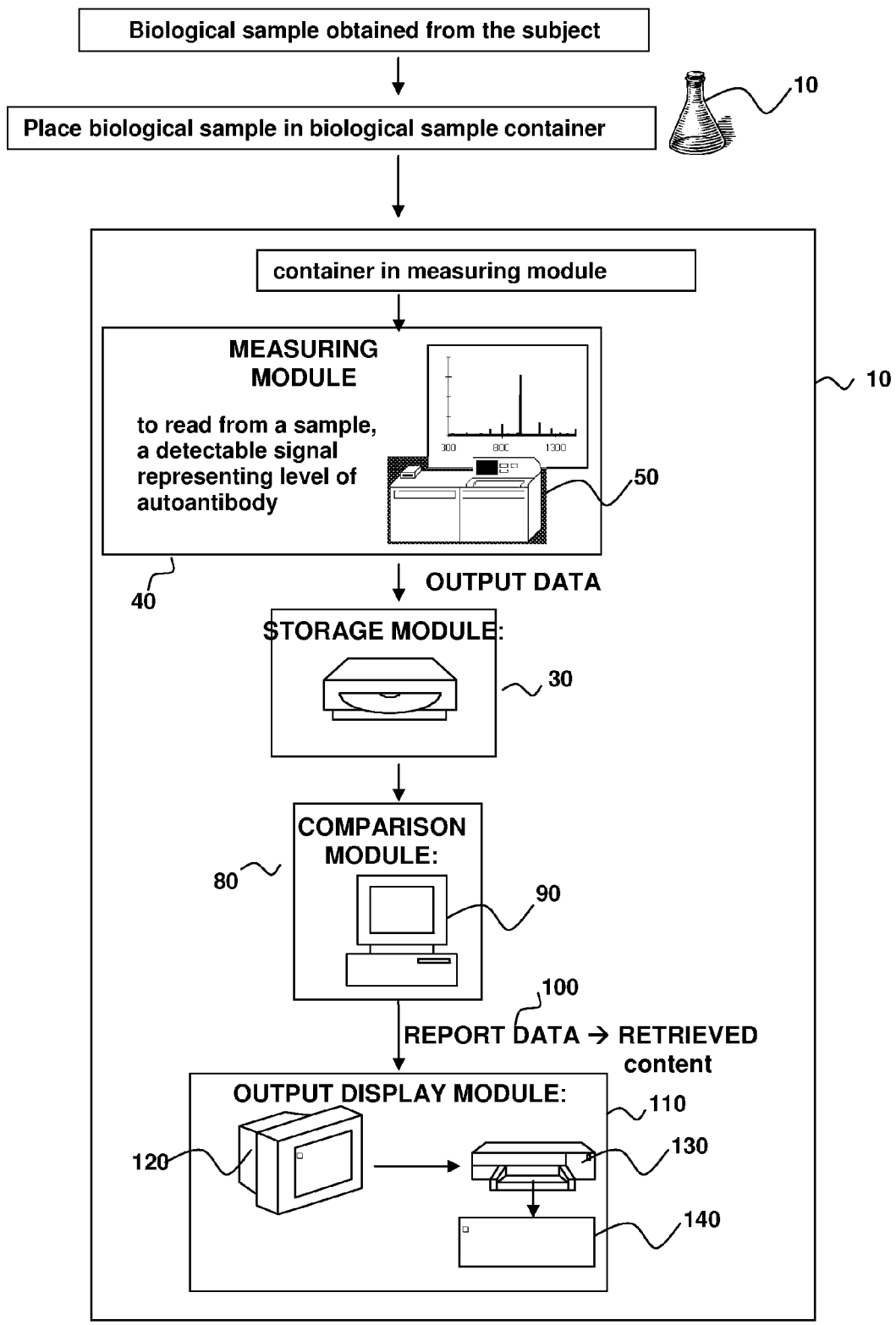
FIG. 7 is a block diagram showing an exemplary system for IBM diagnosis.
Figure 8:
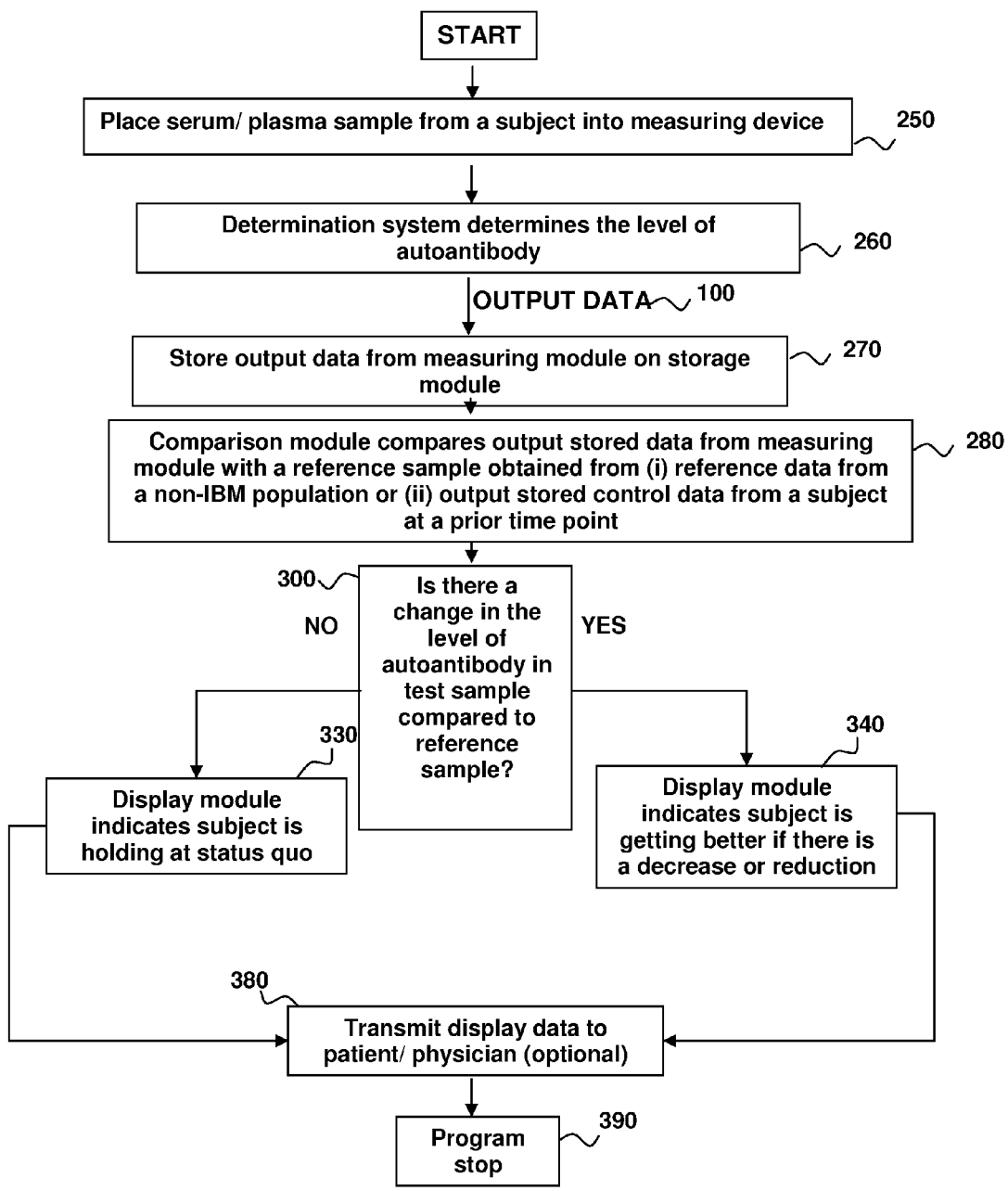
FIG. 8 is an exemplary set of instructions on a computer readable storage medium for use with the systems described herein.

As an exemplary, a typical ELISA-based kit assay would involve dispensing a sample containing the serum into microtiter plate wells, preferably in duplicates or triplicates (as in FIGS. 5 and 6). The wells are previously coated with immobilized unlabeled NT5C1A or NT5C1B, or protein fragment thereof, or an isolated peptide, or a fusion protein described herein, i.e., the antigen of the autoantibody of interest. In addition, a fixed amount of the standard anti-IgG provided with the kit is also dispensed into reference wells in the microtiter plate, also preferably in duplicates or triplicates, according the kit's instruction. The fixed amount of the standard anti-IgG corresponding to at least two fold of the reference value of the anti-NT5C1A or NT5C1B, or protein fragment thereof autoantibodies normally present in healthy subjects. A second fixed amount of the standard anti-IgG corresponding to two fold lower than of the reference value of the autoantibodies can be added to another set of reference wells. Subsequently, labeled detection antibody specific for the anti-NT5C1A or NT5C1B auto-antibodies or specific to an antibody of the patient is added to both sample and reference wells, e.g. an anti-IgG antibody or anti-human antibody. This is a "sandwich" ELISA assay, where the auto-antibodies are sandwich between the antigen and an anti-IgG antibody. Since the amount of label detected is a measure of the amount of auto-antibodies present in the wells, the amounts of label detected in the various wells provides means for comparing the level of the auto-antibodies in the sample with the reference value of the auto-antibodies normally present in healthy subject. For example, if the label is colored latex beads, greater color intensity in the sample wells compared to the reference wells indicates that the level of auto-antibodies in the sample is higher than two fold of the reference value of the auto-antibodies normally present in healthy subject. On the other hand, if the color intensity in the sample wells is lower compared to the reference well, that indicate that the level of the auto-antibodies in the sample is at least two fold lower than of the reference value of the auto antibody normally present in healthy subject.

Computer-Based Systems and Computer Data Storage

In another embodiment, provided herein is a system comprising a measuring module measuring autoantibody information comprising a detectable signal from an immunoassay indicating the presence or level of antibodies that are reactive to at least a ~43 kDa protein from a muscle lysate or a mammalian cell lysate, the autoantibodies are from a blood sample obtained from a patient; a storage module configured to store data output from the measuring module; a comparison module adapted to compare the data stored on the storage module with a reference level, and to provide a retrieved content, and an output module for displaying the retrieved content for the user, wherein the retrieved content, the presence of detectable amount of antibodies reactive against to at least a ~43 kDa protein from a muscle lysate or a mammalian cell lysate, indicates that the patient has IBM or has a relapse of IBM.

In another embodiment, provided herein is a system comprising a measuring module measuring autoantibody information comprising a detectable signal from an immunoassay indicating the presence or level of autoantibodies from a blood sample obtained from a patient, autoantibodies are reactive to a NT5C1A, NT5C1B or a protein fragment thereof, or an isolated peptide, or a fusion protein described herein; a storage module configured to store data output from the measuring module; a comparison module adapted to compare the data stored on the storage module with a reference level, and to provide a retrieved content, and an output module for displaying the retrieved content for the user, wherein the retrieved content, the presence of detectable amount of autoantibodies reactive against NT5C1A, NT5C1B or protein fragment, or an isolated peptide, or a fusion protein described herein, indicates that the patient has IBM or has a relapse of IBM.

In another embodiment, provided herein is a system for evaluating the efficacy of a treatment for a patient having IBM or to facilitate the prognosis evaluation of IBM in a patient, comprising: a measuring module configured to receive and output autoantibody information from a blood sample obtained from a patient, wherein the autoantibodies information measures the level of autoantibodies that are reactive to at least a ~43 kDa protein from a muscle lysate or a mammalian cell lysate; a storage module configured to store output information from the measuring module; a comparison module adapted to compare the data stored on the storage module with a reference data, and to provide a comparison content, wherein the reference data comprises previous data from the same patient wherein the previous data had indicated detectable amounts of auto-antibodies, and an output module for displaying the comparison content for the user, wherein if there is no detectable amount of autoantibodies reactive at least a ~43 kDa protein from the muscle lysate or the mammalian cell lysate, then the patient is in remission or if there is a reduction of at least 5% compared to a prior reading, then the treatment is effective in the patient.

In another embodiment, provided herein is a system for evaluating the efficacy of a treatment for a patient having IBM or to facilitate the prognosis evaluation of IBM in a patient, comprising: a measuring module configured to receive and output autoantibody information from a blood sample obtained from a patient, wherein the autoantibodies information measures the level of auto antibodies that are reactive to a NT5C1A or a NT5C1B or a protein fragment thereof, or an isolated peptide, or a fusion protein described herein; a storage module configured to store output information from the measuring module; a comparison module adapted to compare the data stored on the storage module with a reference data, and to provide a comparison content, wherein the reference data comprises previous data from the same patient wherein the previous data had indicated detectable amounts of autoantibodies, and an output module for displaying the comparison content for the user, wherein if there is no detectable amount of autoantibodies reactive against NT5C1A or a NT5C1B or a peptide fragment, or an isolated peptide, or a fusion protein described herein, then the patient is in remission or if there is a reduction of at least 5% compared to a prior reading, then the treatment is effective in the patient.

In one embodiment, provided herein is a computer readable storage medium comprising a storing data module containing data from a blood sample obtained from a subject that represents a signal level from an immunoassay for autoantibodies that are reactive to a reactive to at least a ~43 kDa protein from a muscle lysate or a mammalian cell lysate, or a NT5C1A or a NT5C1B or a protein fragment thereof, or an isolated peptide, or a fusion protein described herein; a comparison module that compares the data stored on the storing data module with a reference data, and to provide a comparison content, and an output module displaying the comparison content for the user, wherein the presence of a detectable amount of antibodies reactive against at least a ~43 kDa protein from a muscle lysate or a mammalian cell lysate, or a NT5C1A or a NT5C1B or a protein fragment thereof, or an isolated peptide, or a fusion protein of at least 5% relative to the reference data indicates that the subject has IBM or has a relapse of IBM.

In one embodiment of the system and storage medium described herein, the reference level comprises data from a population of non-IBM healthy individuals and/or non-IBM healthy individuals without any inflammatory conditions as described in this application. For example, the data are the detection signals obtained from the human sera or plasma from individuals of the population, from human sera or plasma at 1:100 dilution with 1×PBS and are immunoreactive with 0.5 g of at least a ~43 kDa protein from a muscle lysate or a mammalian cell lysate, or 0.5 g of a muscle lysate or a mammalian cell lysate, or 0.5 g of a NT5C1A or a NT5C1B or a protein fragment thereof, or an isolated peptide, or a fusion protein, wherein horse-radish peroxidase labeled anti-human IgG antibody is the labeled detection antibody and the detection signal is chemiluminescence.

In some embodiments, the reference data comprises previous data from the same subject or patient wherein the previous data had indicated detectable amounts of autoantibodies.

Alternatively, the reference data comprises data from a population of non-IBM healthy individuals and/or non-IBM healthy individuals without any inflammatory conditions, the reference data is the average of the detection signals obtained by any serological immunoassay using the human sera or plasma from non-IBM healthy individuals, and the detection signals correspond to the immunoreactivity of the sera or plasma with 0.5 g of a NT5C1A or a NT5C1B or a protein fragment thereof, Embodiments of the system and storage medium are described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media #30 can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present technology discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present technology. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the system and storage medium described herein include at minimum a measuring module #40, a storage module #30, a comparison module #80, and an output module #110. The functional modules can be executed on one, or multiple, computers, or by using one, or multiple, computer networks. The measuring module has computer executable instructions to provide e.g., expression information in computer readable form.

The measuring module #40 can comprise any system for detecting a signal representing expression level of auto-antibodies. Such systems can include DNA microarrays, RNA expression arrays, any ELISA detection system and/or any Western blotting detection system.

The information determined in the measuring system can be read by the storage module #30. As used herein the "storage module" is intended to include any suitable computing or processing apparatus or other device configured or adapted for storing data or information. Examples of electronic apparatus suitable for use with the present technology include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon expression level or protein level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment of the system and storage medium described herein, the reference data stored in the storage module to be read by the comparison module includes but are not limited to serological immunoassay, ELISA, and Western blot densitometry data obtained from a population of non-IBM subjects, a population of IBM subjects or expression data obtained from the same subject at a prior time point using the measuring module #40.

The "comparison module" #80 can use a variety of available software programs and formats for the comparison operative to compare expression data determined in the measuring module to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to normalized expression level of auto-antibodies, presence/absence of IBM in an individual, efficacy of treatment in an individual.

The comparison module, or any other module of the system and storage medium described herein, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executable will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GENBANK™ or Swiss Pro World Wide Web site).

The comparison module provides a computer readable comparison result that can be processed in computer readable form by predefined criteria, or criteria defined by a user, to provide a content-based in part on the comparison result that may be stored and output as requested by a user using an output module #110.

The content based on the comparison result, may be an expression value compared to a reference showing the presence/absence of IBM in an individual or the relapse or remission of IBM in a subject.

In one embodiment of any system described herein, the content based on the comparison result is displayed on a computer monitor #120. In one embodiment of any system described herein, the content based on the comparison result is displayed through printable media #130 and #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the system and storage medium described herein can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

Embodiments described herein therefore provide for systems (and computer readable media for causing computer systems) to perform methods for diagnosing IBM, assessing treatment efficacy of IBM, and/or monitoring recurrence of IBM in an individual.

Systems and computer readable media described herein are merely illustrative embodiments for detecting autoantibodies reactive against at least a ~43 kDa protein from a muscle lysate or a mammalian cell lysate, or 0.5 g of a muscle lysate or a mammalian cell lysate, or 0.5 g of a NT5C1A or a NT5C1B, or a protein fragment thereof, or an isolated peptide, or a fusion protein described herein in an individual, and are not intended to be limiting in scope. Variations of the systems and computer readable media described herein are possible and are intended to fall within the scope of systems and computer readable media described herein.

The modules of the machine, or those used in the computer readable medium, may assume numerous configurations. For example, function may be provided on a single machine or distributed over multiple machines.

Sample Collection and Preparation

Collections of samples can be performed by methods well known to those skilled in the art.

For example, the patient's blood can be drawn by trained medical personnel directly into anti-coagulants such as citrate and EDTA. The whole blood can be separated into the plasma portion, the cells, and platelets portion by refrigerated centrifugation at 3500×G for 2 minutes. After centrifugation, the supernatant is the plasma.

Alternately, the serum can be collected from the whole blood. Collect the blood in a hard plastic or glass tube; blood will not clot in soft plastic. Draw 15 mL of whole blood for 6 mL of serum. The whole blood is allowed to stand at room temperature for 30 minutes to 2 hours until a clot has formed. Carefully separate clot from the sides of the container using a glass rod or wooden applicator stick and leave overnight at 4° C. After which, decant serum, centrifuge, and/or using a Pasteur pipette, remove serum into a clean tube. Clarify the serum by centrifugation at 2000-3000 rpm for 10 minutes. The serum is stored at −20° or −80° C. before analysis for auto-antibodies is performed. Detailed description of obtaining serum using collection tubes can be found in U.S. Pat. No. 3,837,376 and is hereby incorporated by reference in its entirety. Blood collection tubes can also be purchased from BD Diagnostic Systems, Greiner Bio-One, and Kendall Company.

Detection of Autoantibodies

The detection of autoantibodies against at least a ~43 kDa protein from a muscle lysate or a mammalian cell lysate, or a NT5C1A, or a NT5C1B, or a protein fragment thereof, or an isolated peptide, or a fusion protein described herein in the blood, serum or plasma of a patient can be detected by any method known in the art. In one embodiment, the levels of autoantibodies in the blood samples of patients are detected by an immunoassay. Immunoassays include but are not limited to enzyme immunoassay (EIA), also called enzyme-linked immunosorbant assay (ELISA), radioimmunoassay (RIA), diffusion immunoassay (DIA), fluoroimmunoassay (FIA), chemiluminescent immunoassay (CLIA), counting immunoassay (CIA), lateral flow tests or immunoassay (LFIA), also known as lateral flow immunochromatographic assays, and magnetic immunoassay (MIA). In some embodiment, the immunoassay can be a quantitative or a semi-quantitative immunoassay.

An immunoassay is a biochemical test that measures the concentration of a substance in a biological sample, typically fluid sample such as serum, using the reaction of an antibody or antibodies to its antigen. The assay takes advantage of the specific binding of an antibody to its antigen. For the methods and assays described herein, specific binding of the autoantibodies with respective proteins or protein fragments, or an isolated peptide, or a fusion protein described herein occurs in the immunoassay to form an autoantibody-protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries. For the methods and assays described herein, wherein the autoantibodies are detected by ELISA, a known amount of antigen (e.g., 0.5 g of at least a ~43 kDa protein from a muscle lysate or a mammalian cell lysate, or 0.5 g of a muscle lysate or a mammalian cell lysate, or 0.5 g of a NT5C1A or a NT5C1B or a protein fragment thereof, or an isolated peptide, or a fusion protein described herein) is affixed to a surface or solid support. Then the sample to be tested, e.g. blood, serum or plasma, suspected of containing autoantibodies, is washed over the surface so that the autoantibodies can bind to the immobilized antigen if the autoantibodies are present. The surface is washed to remove any unbound antibodies from the test sample and a detection antibody is applied to the surface. The detection antibody is specific to the antibodies from the subject. For example, if the subject is a human, the detection antibody could be an anti-human IgG antibody. This detection antibody is labeled, usually by linkage to an enzyme. In the final steps of an ELISA, a substance or agent is added the enzyme-linked detection antibody, the substance or agent is that which the enzyme can convert to some detectable signal. For example, in the case of fluorescence ELISA, when light is shone upon the sample, any antigen/antibody complexes will fluoresce so that the amount of autoantibodies present in the sample can be measured. This is the indirect enzyme-linked immunosorbent assay.

The following is a general standard protocol for setting up and performing an indirect enzyme-linked immunosorbent assay. Using 96-well microtiter plates (Falcon Pro-Bindassay plate 3915; Becton Dickinson, Paramus, N.J.), test wells are coated with one or more desired or target antigen by incubation with 100 µl of a purified NT5C1A or NT5C1B or a protein fragment thereof, or an isolated peptide, or a fusion protein described herein (3 g/ml in PBS) or 100 µl of at least a ~43 kDa protein from a muscle lysate or a mammalian cell lysate, or 100 µl of a muscle lysate or a mammalian cell lysate (0.5 g/ml). The 100 µl aliquots are added to each well and incubated overnight at room temperature, with PBS substituted for the antigen in control wells. After the plates have been washed three times with PBS-TWEEN, 250 µl of 2% BSA in PBS is added to each well, and the plates are incubated for 1 h at room temperature. The plates are washed three times with PBS TWEEN and incubated for 1 h at room temperature with test sera or plasma and control sera or plasma (one high-positive serum or plasma specimen, two negative serum or plasma specimens, and one weak-positive serum or plasma specimen) diluted 1:100 in PBS TWEEN-BSA; each serum or plasma specimen is tested in triplicate in antigen-coated wells as well as in antigen control wells. The plate is then assayed (with appropriate controls) for the presence of human auto-antibodies IgG against the desired respective antigen (NT5C1A or NT5C1B or a protein fragment or cell/muscle lysate) by incubation for 1 h at room temperature with 100 µl of goat anti-human IgG conjugated with horseradish peroxidase (Bio-Rad, Richmond, Calif.) per well diluted 1:2,000 in PBS-Tween-BSA. After three washes in PBS-Tween, the substrate solution (o-phenylenediamine dihydrochloride; SIGMA-ALDRICH®) is added to each well. The plates are then incubated for 30 min at room temperature in darkness, and the reaction is terminated by the addition of 2N sulfuric acid. The optical density values at 490 nm ($OD_{490}$) are measured in a micro plate ELISA reader. For each serum specimen, mean $OD_{490}$ readings are calculated for the test wells and for the antigen control wells, the latter being subtracted from the former to obtain the net ELISA value.

In one embodiment, an ELISA involving at least one antibody with specificity for the particular desired antigen can also be performed. A known amount of antigen (e.g., 0.5 g of at least a ~43 kDa protein from a muscle lysate or a mammalian cell lysate, or 0.5 g of a muscle lysate or a mammalian cell lysate, or 0.5 g of a NT5C1A or a NT5C1B or a protein fragment thereof, or an isolated peptide, or a fusion protein described herein) is immobilized on a solid support (usually a polystyrene micro titer plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against at least a ~43 kDa protein from a muscle lysate or a mammalian cell lysate, a NT5C1A or NT5C1B or a protein fragment thereof, or an isolated peptide, or a fusion protein described herein and are not derived from the subject are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., blood, serum or plasma) from a patient is mixed with a known amount of desired antigen (e.g., at least a ~43 kDa protein from a muscle lysate or a mammalian cell lysate, a NT5C1A or NT5C1B or a protein fragment thereof) together with the horseradish peroxidase labeled antibodies and the mixture is then are added to coated wells to form competitive combination. After incubation, if the autoantibody level is high in the sample, a complex of autoantibodies-antigen-labeled antibody will form. This complex is free in solution and can be washed away. Washing the wells will remove the complex. Then the wells are incubated with TMB (3,3',5,5'-tetramethylbenzidene) color development substrate for localization of horseradish peroxidase-conjugated antibodies in the wells. There will be no color change or little color change if the autoantibody level is high in the sample. If there is no autoantibody or little autoantibodies present in the sample, a different complex in formed, the complex of solid support bound antibodies-antigen-labeled antibody. This complex is immobilized on the plate and is not washed away in the wash step. Subsequent incubation with TMB will produce much color change. Such a competitive ELSA test is specific, sensitive, reproducible and easy to operate.

In one embodiment, the reverse-sandwich (RS) ELISA is used (Miyazawa H., et. al, J Allergy Clin Immunol. 1988; 82:407-413), wherein the autoantibody of interest, in the methods and assays described herein, the autoantibodies against at least a ~43 kDa protein from a muscle lysate or a mammalian cell lysate, a NT5C1A or NT5C1B or a protein fragment thereof, or an isolated peptide, or a fusion protein described herein, is sandwiched by respective antigen; one antigen is affixed to a surface and the second antigen is soluble and tagged. This method is also known as the double-antigen sandwich method.

The following is a general standard protocol for setting up and performing a RS-ELISA. A 0.1 ml quantity of at least a ~43 kDa protein from a muscle lysate or a mammalian cell lysate, a NT5C1A or NT5C1B or a protein fragment thereof, or an isolated peptide, or a fusion protein described herein (0.5 µg/ml) plus bovine serum albumin (BSA; 25 µg/ml) in 0.5 M NaCl-0.1% $NaN_3$-0.05 M sodium carbonate (pH 9.6) is added to wells of Maxisorp microplates (Nalge Nunc, Copenhagen, Denmark). The plates are incubated overnight at 4° C. for antigen immobilization. After the wells are washed test sera diluted 1:4, 1:40, and 1:400 with FBS-PBST (10% [vol/vol] fetal bovine serum [FBS], 0.1% $NaN_3$-phosphate-buffered saline [PBS]-0.05% TWEEN 20 [PBST]) are added, and the plates are incubated for 60 min at room temperature. Seven threefold serial dilutions of a reference serum are used. After another wash, biotinylated respective desired antigen (0.05 μg/ml) in FBS-PBST is then added to the wells, and the reaction is allowed to take place for 60 min at room temperature. The wells are washed again, streptavidin-conjugated β-d-galactosidase (diluted 1:50,000 in PBST containing 1% BSA) is added, and the plates are incubated for 60 min at room temperature. After another wash, 0.2 mM 4-methylumbelliferyl-β-d-galactoside in 0.1 M NaCl-1 mM $MgCl_2$-0.1% BSA-0.1% NaN3-0.01 M sodium phosphate (pH 7.0) is added. The wells are sealed with tape, and the plates are immersed in 37° C. water for 60 min. Finally, 0.1 ml of 0.1 M glycine-NaOH (pH 10.2) is added to each well to stop the enzyme reaction. The fluorescence units (FU) in each well are measured with a Fluoroskan II apparatus (Flow Laboratories, Rockville, Md.). The antibody concentrations of the test sera or plasma are calculated from the titration curve of the respective reference serum or plasma with known antibody units per milliliter.

In one embodiment, the levels of autoantibodies in a blood sample are detected by a lateral flow immunoassay test (LFIA), also known as the immunochromatographic assay, or strip test. LFIAs are a simple device intended to detect the presence (or absence) of a target autoantibodies in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test it encounters a coloured reagent which mixes with the sample and transits the substrate encountering lines or zones which have been pretreated with an antibody or antigen. Depending upon the autoantibodies present in the sample the coloured reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be use on site in the field.

LFIA tests can be operated as either competitive or sandwich assays. Sandwich LFIAs are similar to sandwich ELISA.

Figure 4:
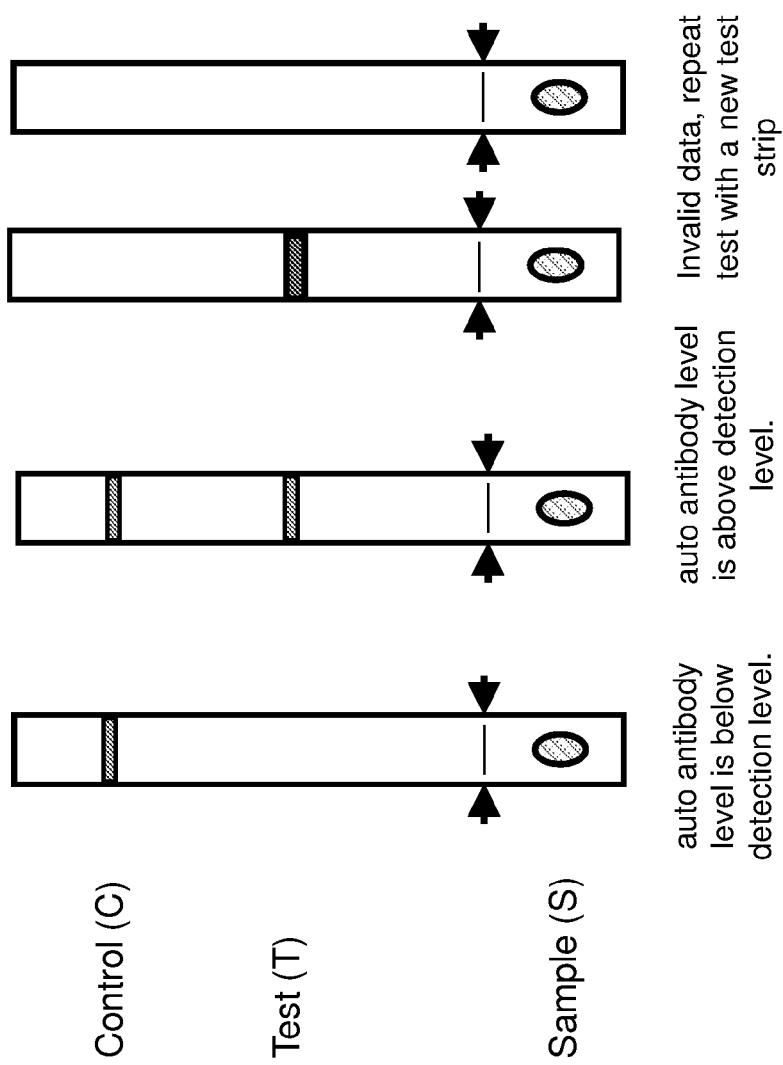
FIG. 4 is a schematic diagram showing the interpretation of the results obtained using the test strip shown in FIG. 3.

A typical test strip consists of the following components: (1) sample application area comprising an absorbent pad (i.e. the matrix or material) onto which the test sample is applied; (2) conjugate or reagent pad—this contains antibodies or antigen depending on whether the tested entity is an autoantibody or a biomarker (i.e., an antigen), the antibodies or antigen is usually colloidal gold particles, or latex microspheres; test results area comprising a reaction membrane—typically a hydrophobic nitrocellulose or cellulose acetate membrane onto which anti-antigen antibodies are immobilized in a line across the membrane as a capture zone or test line (a control zone may also be present, containing antibodies specific for the conjugate antibodies); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly. FIGS. 3-4 show the various components and embodiments of several test strips.

In some embodiments, the lateral flow immunoassay is a double antibody sandwich assay, a competitive assay, a quantitative assay or variations thereof.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technology for the detection of auto antibodies.

In one embodiment of any of the method or assay described herein, the detection antibody used is detectably labeled. As used herein "detectably labeled", includes antibodies that are labeled by a measurable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, HIS, or biotin.

In one embodiment, the detectable label is a dye. A "dye" refers to a substance, compound or particle that can be detected, particularly by visual, fluorescent or instrumental means. A dye can be, for example, but not limited to, a pigment produced as a coloring agent or ink, such as Brilliant Blue, 3132 Fast Red 2R and 4230 Malachite Blue Lake, all available from Hangzhou Hongyan Pigment Chemical Company, China. The "dye" can also be a particulate label, such as, but not limited to, blue latex beads or gold particles. The particulate labels may or may not be bound to a protein, depending upon if it is desired for the particles to move in the test strip or not. If the particles are to be immobilized in the test strip, the particles may be conjugated to a protein, e.g. the anti-antigen antibody, which in turn is bound to the test strip by either physical or chemical means.

Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif.

In one embodiment of any of the method or assay described herein, the detection antibody is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes contemplated for use to detectably label the antibodies include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In other embodiments, the detection antibody is label with a fluorescent compound. When the fluorescently labeled antibody is exposed to light of the proper wavelength, its presence can then be detected due to fluorescence. Among the most commonly used fluorescent labeling compounds are CY dyes, fluorescein isothiocyanate, rhodamine, phycoerytherin, phycocyanin, allophycocyanin, o-phthaldehyde and fluorescamine.

A detection antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

A detection antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904. These references are hereby incorporated by reference in their entirety.

Other techniques can be used to detect the autoantibodies in a sample. One such technique is Western blotting (Towbin et at., Proc. Nat. Acad. Sci. 76:4350 (1979)); another is an adaptation of the Western blot, the dot blots. In the Western blots, the at least a ~43 kDa protein from a muscle lysate or a mammalian cell lysate, a NT5C1A or NT5C1B or a protein fragment thereof, or an isolated peptide, or a fusion protein described herein can be dissociated with detergents and heat, and separated on an SDS-PAGE gel before being transferred to a solid support, such as a nitrocellulose membrane. The membrane is incubated with a sample suspected of containing autoantibodies against at least a ~43 kDa protein from a muscle lysate or a mammalian cell lysate, a NT5C1A or NT5C1B or a protein fragment thereof, or an isolated peptide, or a fusion protein respectively. The membrane is then washed to remove unbound proteins and proteins (including antibodies) with non-specific binding. Detectably labeled enzyme-linked secondary or detection antibodies can then be used to detect and assess the amount of autoantibodies in the sample tested. The intensity of the signal from the detectable label corresponds to the amount of enzyme present, and therefore the amount of auto-antibodies against respective antigen. Levels can be quantified, for example by densitometry.

In some embodiments, the immunoassays operate on a purely qualitative basis. However it is possible to measure the intensity of the test line to determine the quantity of autoantibodies in the blood sample when using an immunoassay such a LFIA. Implementing a magnetic immunoassay (MIA) in the lateral flow test form also allows for getting a quantified result.

In one embodiment, the detection of autoantibodies against at least a ~43 kDa protein from a muscle lysate or a mammalian cell lysate, a NT5C1A or NT5C1B or a protein fragment thereof, or an isolated peptide, or a fusion protein described herein is considered positive when the immunoassay signal is at least 5% over that of an control immunoassay signal obtained in the absence of an antibody against the respective antigen thereof or in the presence of a non-related antibody.

By a "non-related antibody" means an antibody that does not bind or is not reactive against at least a ~43 kDa protein from a muscle lysate or a mammalian cell lysate, a NT5C1A or NT5C1B or a protein fragment thereof, or an isolated peptide, or a fusion protein described herein.

In another embodiment, the control immunoassay signal is that obtained with the serum of non-IBM healthy subject, these subjects do not have the clinical features of the disease. In another embodiment, these non-IBM healthy subjects do not have any inflammatory conditions. In another embodiment, the control immunoassay signal is the average value obtained for a population of non-IBM healthy subjects. A population is at least 25 non-IBM healthy subjects, preferably more.

The present technology can be defined in any of the following numbered paragraphs:

[01] A method for identifying the likelihood of a patient having IBM comprising:
  (a) measuring a level of autoantibody that target at least a ~43 kilodalton (kDa) protein from a muscle lysate or a mammalian cell lysate, the autoantibodies are from a blood sample from the patient; and
  (b) comparing the level of autoantibody measured to a reference level, wherein a level of autoantibody at least 5% over that of the reference level indicates that the patient is likely to have IBM.

[02] A method for evaluating the efficacy of a treatment for a patient having IBM, the assay comprising:
  (a) measuring a level of autoantibodies that are reactive to at least a ~43 kDa protein from a muscle lysate or a mammalian cell lysate in at least two blood samples obtained from a patient at different times, wherein the different times are a first time point and a second time point, wherein the second time point is after the first time point, and wherein the patient has IBM and is being treated for IBM; and
  (b) comparing the levels of the autoantibodies in the at least two blood samples, wherein a decrease in the level of the autoantibodies taken at the second time point compared to the first time point indicates that the treatment is effective, wherein an increase in the level of the autoantibodies taken at the second time point compared to the first time point or the levels are approximately the same indicates that the treatment is not effective, and wherein when the level of autoantibodies in the second time point decreases to below a detection limit indicates that the patient is in remission.

[03] The method of paragraph 1 or 2, wherein the measurement of autoantibodies targeting the ~43 kDa protein from the muscle lysate or the mammalian cell lysate comprises a one-dimension SDS-PAGE (1D SDS-PAGE) and a Western blot.

[04] The method of paragraph 1, 2 or 3, wherein the measurement of autoantibodies targeting the ~43 kDa protein from the muscle lysate or the mammalian cell lysate comprises separating the proteins in the muscle lysate or the mammalian cell lysate in a 1D SDS-PAGE gel and electrotransfer of the separated proteins to a solid support.

[05] The method of any one of paragraphs 1-4, wherein the measurement of autoantibodies targeting the ~43 kDa protein from the muscle lysate or the mammalian cell lysate comprises the steps of:
(a) contacting a blood sample from the patient with a muscle lysate or a mammalian cell lysate;
(b) forming an antibody-protein complex between the autoantibody present in the blood sample with a protein from the muscle lysate or mammalian cell lysate respectively;
(c) washing to remove any unbound autoantibodies not in a complex with a protein from the muscle lysate or the mammalian cell lysate;
(d) adding a detection antibody that is labeled and is reactive to the autoantibody from the blood sample;
(e) washing to remove any unbound labeled detection antibody; and
converting the label to a detectable signal, the detectable signal indicates the presence of autoantibodies against at least a ~43 kDa protein used in step (a).

[06] The method of any one of paragraphs 1-5, the blood sample from the patient is plasma or serum.

[07] The method of any one of paragraphs 1-6, the patient is a human.

[08] The method of any one of paragraphs 1-7, the muscle lysate or the mammalian cell lysate is derived from a human.

[09] The method of paragraph 8, the mammalian cell lysate is HELA cell lysate.

[10] The method of any one of paragraphs 1-9, the method further comprising selecting a patient suspected of having IBM.

[11] The method of paragraph 10, the patient presents at least one symptom known to be associated with IBM.

[12] The method of paragraph 11, the patient has progressive muscle weakness, skeletal muscle pain and/or muscle fatigue.

[13] The method of any one of paragraphs 1-12, the detection antibody is labeled by covalently linking to an enzyme, label with a fluorescent compound or metal, or label with a chemiluminescent compound.

[14] The method of any one of paragraphs 2-13, the treatment is experimental.

[15] The method of any one of paragraphs 2-14, wherein the second time point is at least one month after the start of treatment.

[16] The method of any one of paragraphs 1-15, wherein the IBM is idiopathic.

[17] An isolated peptide derived from the sequence of a cytosolic 5'-nucleotidase 1A protein (NT5C1A), or a cytosolic 5'-nucleotidase 1B (NT5C1B) protein or isoforms thereof, the peptide binds autoantibodies in a blood sample of a patient having inclusion body myositis (IBM).

[18] The isolated peptide of paragraph 17, wherein the peptide comprising at least 6 contiguous amino acid residues and is not a full-length NT5C1A, a full-length NT5C1B polypeptide or isoforms thereof.

[19] The isolated peptide of paragraph 17 or 18, wherein sequence of the NT5C1A, NT5C1B or isoforms thereof is derived from a human.

[20] The isolated peptide of any one of paragraphs 17-19, wherein the patient is a human.

[21] The isolated peptide of any one of paragraphs 17-20, wherein the isolated peptide is selected from the group consisting of SEQ. ID. Nos: 3-13.

[22] The isolated peptide of any one of paragraphs 17-21, wherein the isolated peptide is made by recombination molecular biology method, by synthetic chemical synthesis, or protein fragmentation or enzymatic digestion of a full-length NT5C1A, a full-length NT5C1B polypeptide or isoforms thereof.

[23] The isolated peptide of any one of paragraphs 17-22, wherein the isolated peptide comprises at least one conservative amino acid substitutions and substantially retains immunoreactivity with autoantibodies in the blood sample of a patient having IBM.

[24] The isolated peptide of paragraph 23, wherein the isolated peptide comprises no more than five conservative amino acid substitutions.

[25] The isolated peptide of any one of paragraphs 17-24, wherein the isolated peptide wherein the isolated peptide is placed or conjugated to a solid support.

[26] The isolated peptide of any one of paragraphs 17-25, wherein the isolated peptide is fused to a heterologous peptide or polypeptide to form a fusion or chimeric protein, wherein the fusion protein is not a full-length NT5C1A a full-length NT5C1B polypeptide or isoform thereof.

[27] An isolated peptide derived from the sequence of a cytosolic 5'-nucleotidase 1A protein (NT5C1A), or a cytosolic 5'-nucleotidase 1B protein (NT5C1B) or isoform thereof having immunoreactivity with autoantibodies in a blood sample of a patient having inclusion body myositis (IBM), the isolated peptide consisting essentially of SEQ. ID. Nos: 6-16 or a conservative amino acid substitution variant thereof that substantially retains immunoreactivity with autoantibodies in the blood sample of a patient having IBM.

[28] The isolated peptide of paragraph 27, wherein the isolated peptide is placed or conjugated to a solid support.

[29] The isolated peptide of paragraph 27 or 28, wherein the isolated peptide is fused to a heterologous peptide or polypeptide to form a fusion or chimeric protein, wherein the fusion protein is not a full-length NT5C1A, a full-length NT5C1B polypeptide or isoform thereof.

[30] A fusion protein comprising a peptide of any one of paragraphs 17-25 and 27-29 fused to a heterologous peptide or polypeptide, wherein the fusion protein is not a full-length NT5C1A, a full-length NT5C1B polypeptide or isoform thereof.

[31] An assay comprising:
(a) measuring a level of autoantibodies that are reactive to a cytosolic 5'-nucleotidase 1A (NT5C1A), or a cytosolic 5'-nucleotidase 1B (NT5C1B), or an isoform thereof, or a peptide fragment thereof, or an isolated peptide of any one of paragraphs 17-29 or a fusion protein of paragraph 30, the autoantibodies being in a blood sample obtained from a patient who presents symptoms of inclusion body myositis (IBM); and
(b) comparing the level of the antibodies in the blood sample with a reference level, wherein a detectable of at least 5% in the antibodies in the patient over that of the reference level indicates the likelihood of IBM.

[32] An assay for evaluating the efficacy of a treatment in a patient with IBM comprising:
(a) measuring a level of autoantibodies that are reactive to a cytosolic 5'-nucleotidase 1A (NT5C1A), or a cytosolic 5'-nucleotidase 1B (NT5C1B), a NT5C1B isoform thereof, a peptide fragment thereof, or an isolated peptide of any one of paragraphs 17-29, or a fusion protein of paragraph 30, the autoantibodies being in at least two blood samples obtained from a patient at different times, wherein the different times are a first time point and a second time point, wherein the second time point is after the first time point, and wherein the patient has inclusion body myositis (IBM) and is being treated for IBM; and
(b) comparing the levels of the antibodies in the at least two blood samples, wherein a decrease in the level of the antibodies taken at the second time point compared to the first time point indicates that the treatment is effective, wherein an increase in the level of the antibodies taken at the second time point compared to the first time point or the levels are approximately the same indicates that the treatment is not effective, and wherein when the level of antibodies in the second time point decreases to below a detection limit indicates that there is remission.

[33] The assay of paragraph 32, wherein the treatment is experimental.

[34] The assay of paragraph 32 or 33, wherein the second time point is at least one month after the start of treatment.

[35] The assay of any one of paragraphs 31-34, wherein the IBM is idiopathic.

[36] The assay of any one of paragraphs 31-35, wherein the blood sample is a plasma or serum sample.

[37] The assay of any one of paragraphs 31-36, wherein the reactive autoantibodies is measured by the steps comprising:
(a) contacting the blood sample from the patient with the NT5C1A or the NT5C1B or the isoform thereof, or the peptide fragment or the isolated peptide of any one of paragraphs 17-29 or a fusion protein of paragraph 30;
(b) forming an autoantibody-protein complex between the autoantibody present in the blood sample with the NT5C1A or the NT5C1B or the isoform thereof, or the peptide fragment or the isolated peptide of any one of paragraphs 17-29 or a fusion protein of paragraph 30 respectively used in step (a);
(c) washing to remove any unbound autoantibodies not in a complex with a protein or peptide or fusion protein;
(d) adding a detection antibody that is labeled and is reactive to the autoantibody from the blood sample;
(e) washing to remove any unbound labeled detection antibody; and
(f) converting the label to a detectable signal, the detectable signal indicates the presence of autoantibodies against the NT5C1A or the NT5C1B or the isoform thereof, or the peptide fragment or the isolated peptide of any one of paragraphs 17-29 or a fusion protein of paragraph 30 respectively used in step (a).

[38] The assay of paragraph 37, wherein the NT5C1A or the NT5C1B or the isoform thereof, or the peptide fragment thereof or the isolated peptide of any one of paragraphs 17-29 or a fusion protein of paragraph 30 used in step (a) is deposited or immobilized on a solid support.

[39] The assay of paragraph 38, wherein the support is in the format of a dipstick, a test strip, a latex bead, a microsphere or a multi-well plate.

[40] The assay of paragraphs 37, 38 or 39, wherein the detection antibody is labeled by covalently linking to an enzyme, label with a fluorescent compound or metal, or label with a chemiluminescent compound.

[41] The assay of any one of paragraphs 31-40, more than one of NT5C1A, NT5C1B, isoform thereof, peptide fragment thereof, or the isolated peptide of any one of paragraphs 17-29 or a fusion protein of paragraph 30 is used.

[42] A device for identifying a presence or a level of autoantibodies that are reactive to a NT5C1A, a NT5C1B or a peptide fragment thereof in a blood sample from a patient comprising:
(a) at least a NT5C1A or NT5C1B isoform thereof, peptide fragment thereof, or an isolated peptide of any one of paragraphs 17-29 or a fusion protein of paragraph 30; and
(b) at least one solid support, wherein the protein or peptide or fusion protein of step a is deposited on the support.

[43] The device of paragraph 42, wherein the device performs an assay in which an antibody-protein or antibody-peptide complex is formed.

[44] The device of paragraph 43, wherein the assay is a serological immunoassay.

[45] The device of any one of paragraphs 42-44, wherein the NT5C1A or NT5C1B, or protein fragment thereof is selected from the group consisting of SEQ. ID. NOS: 1-16.

[46] The device of any one of paragraphs 42-45, the solid support is in the format of a dipstick, a microfluidic chip, a multi-well plate or a cartridge.

[47] A kit comprising:
a. a device according to paragraphs 42-46; and
b. at least a detection antibody, wherein the detection antibody is specific for the antibodies of a patient.

[48] The kit of paragraph 47, wherein the detection antibody is detectably labeled.

[49] The kit of paragraph 47 or 48, further comprising at least an agent for producing a detectable signal from the detection antibody.

[50] A system comprising:
(a) a measuring module measuring autoantibody information comprising a detectable signal from an immunoassay indicating the presence or level of autoantibodies that are reactive to at least a NT5C1A or NT5C1B isoform thereof, peptide fragment thereof, or an isolated peptide of any one of paragraphs 17-29 or a fusion protein of paragraph 30, the autoantibodies are from a blood sample obtained from a patient;
(b) a storage module configured to store data output from the measuring module;
(c) a comparison module adapted to compare the data stored on the storage module with a reference level, and to provide a retrieved content, and
(d) an output module for displaying the retrieved content for the user, wherein the retrieved content, the presence of detectable amount of autoantibodies reactive against the protein or peptide or fusion protein used of step a, indicates that the patient has IBM or has a relapse of IBM.

[51] The system of paragraph 50, wherein the reference level comprises data from a population of non-IBM healthy individuals.

[52] A system for evaluating the efficacy of a treatment in a patient with IBM or to facilitate the prognosis evaluation of IBM in a patient, comprising:
(a) a measuring module configured to receive and output auto-antibody information from a blood sample obtained from a patient, wherein the autoantibodies information measures a level of autoantibodies that are reactive to a NT5C1A or NT5C1β isoform thereof, a peptide fragment thereof, or an isolated peptide of any one of paragraphs 17-29 or a fusion protein of paragraph 30;
(b) a storage module configured to store output information from the measuring module;
(c) a comparison module adapted to compare the data stored on the storage module with a reference data, and to provide a comparison content, wherein the reference data comprises previous data from the same patient wherein the previous data had indicated detectable amounts of autoantibodies, and
(d) an output module for displaying the comparison content for the user, wherein if there is no detectable amount of autoantibodies reactive against the protein or peptide or fusion protein of step a, then the patient is in remission or if there is a reduction of at least 5% compared to a prior reading, then the treatment is effective in the patient.

The embodiments described in this disclosure are not intended to be exhaustive or to limit the disclosure to the precise embodiments disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present technology. These publications are provided solely for their disclosure prior to the filing date of the present application. Nothing in this regard should be construed as an admission that the inventors are not entitled to antedate such disclosure by virtue of prior technology or for any other reason. All statements as to the date or representation as to the contents of these documents is based on the information available to the applicants and does not constitute any admission as to the correctness of the dates or contents of these documents.

Definitions of common terms used herein can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006 and Current Protocols in Protein Sciences 2009, Wiley Intersciences, Coligan et al., eds.

Unless otherwise stated, the embodiments described herein were performed using standard procedures, as described, for example in The ELISA guidebook, Sambrook et al., Molecular Cloning: A Laboratory Manual (3 ed.), Cold Spring Harbor Laboratory Press, Cold Spring Harbor, N.Y., USA (2001) and Davis et al., Basic Methods in Molecular Biology, Elsevier Science Publishing, Inc., New York, USA (1995) which are both incorporated by reference herein in their entireties.

This technology is further illustrated by the following examples which should not be construed as limiting.

EXAMPLES

Example 1

Identification of a Circulating Autoantibody Against a 43-kDa Muscle Autoantigen that is Specific to Inclusion Body Myositis (IBM) Among Other Patients with Autoimmune Myopathies Materials and Methods Patient Samples.

Plasma samples from 25 patients with IBM (mean/range age 69/50-87 years), 25 patients with other autoimmune myopathies (mean/range age 48/24-91), and 15 healthy volunteers (mean/range age 52/34-62 years) were probed against normal healthy human muscle lysates. Diagnostic criteria for IBM, dermatomyositis (DM), and polymyositis (PM) were as previously described (19). In particular, all patients with IBM fulfilled European Neuromuscular Centre (ENMC) criteria for probable or definite IBM (20). All healthy volunteers were required to have been free of any infectious or inflammatory diseases, the use of immuno-modulatory agents or vaccination at least for six months prior to collection of blood sample.

Preparation of Gels and Immunoblots.

Muscle lysates were prepared and probed as previously described (19). Briefly, 5 mg of cryostat sectioned normal human muscle was dounce homogenized in 200 μl of lysis buffer (containing 10 mM HEPES, 10 mM KCl, 1 mM EDTA, 0.1 mM EGTA, 10 mM DTT, 5 mM $MgCl_2$ and ROCHE® Complete Protease Inhibitor) and centrifuged at 2,000 g for 10 minutes at 4° C. The supernatant was removed and 30 μg loaded in individual wells of 4-12% NuPAGE Novex Bis-Tris Gels (cat# NP0322BOX, INVITROGEN™). Proteins were separated using SDS-PAGE and transferred to a nitrocellulose membrane. Human plasma (1:1000 dilution) was used as primary antibody and goat anti human-IgG HRP (cat#31410, Pierce Biotechnology, 1:60, 0000 dilution) as secondary antibody, both for 1 hour at room temperature. Blots were developed using the SUPERSIGNAL™ West Pico kit (cat#34077, Pierce Biotechnology, 5 min, room temperature).

Statistical Analysis.

To demonstrate the presence of selective immunoreactivity against a 43 kDa muscle protein in plasma of patients with IBM, the Fisher's exact test was used to compared the disease controls and healthy volunteers, as well as determining the effects of gender, treatment, race and the ANA positivity on such reactivity. The non-parametric Mann-Whitney test was used to determine the effect of age and disease duration on plasma immunoreactivity against the 43 kDa muscle protein.

Results

Immunoblots were performed with plasma samples from 25 people with IBM, 25 people with other autoimmune muscle disease (10 DM patients, 10 PM patients, and 5 myasthenia gravis), and 15 healthy volunteers against normal human muscle lysates. While previous studies have probed myositis blood against proteins derived from non-muscle sources, such as those prepared from HeLa cells (10), sought herein were autoantibodies against proteins derived from human muscle.

Immunoblots against normal human muscle lysates of blood samples from 65 people showed reactivity to an approximately 43 kDa muscle protein in 52% (13 of 25) of IBM samples and in no other autoimmune myopathy or healthy volunteer samples (0 of 40; p<0.0001 Fisher's exact test) (FIG. 1). The detection of a 43 kDa muscle autoantigen thus had a sensitivity of 52% and specificity of 100% for IBM among 50 patients with autoimmune myopathies. The approximately 43-kDa band was sometimes (8 of 13 of positive samples) associated with a fainter nearby band, that may be seen with post-translational modification or partial protein degradation.

IBM is a disease of middle to late age; our patients with IBM were therefore older (mean age 68 years) than patients with other autoimmune myopathies (mean age 48 years), but the presence of the anti-43 kDa autoantibody did not appear age-associated. The mean age of the 13 IBM patients with anti-43-kDa autoantibodies (67 years) did not differ from the mean age of the 13 oldest control patients, none of whom had anti-43-kDa autoantibodies (64 years; p=0.21 Mann-Whitney test). Even within the group of IBM, age played no role in the development of anti-43-kDA autoreactivity, as the mean age of IBM patients with autoreactivity (67 years) did not differ from those without autoreactivity (69 years; p=0.76 Mann-Whitney test). Disease duration was not different between IBM patients demonstrating 43 kDa autoreactivity (6 years) and those without reactivity (8 years; p=0.6 Mann-Whitney test). Gender (p=0.21) and race (p=1.0) were also not associated with the presence of the 43-kDa autoantibody when comparing all patients studied (Fisher's exact test for both analyses).

Treatment status did not appear to affect autoantibody detection, even though most patients with IBM were untreated while most patients with DM and PM received immunomodulating therapy. Within the group of IBM, the proportion of antibody positive untreated patients (12 of 21) did not differ from that of antibody positive treated patients (1 of 4; p=0.32 Fisher's exact test). Analysis of data of all untreated patients showed statistically significant development of autoantibodies in IBM (12 of 21) but not in other disease controls (0 of 7; p=0.01 Fisher's exact test for both comparisons) despite lack of treatment. For the 16 IBM patients tested for anti-nuclear antibodies (ANA) there was no relationship between 43 kDa autoreactivity and a positive test for ANA (p=1 Fisher's exact test).

Autoimmune muscle injury in IBM has been widely believed to be mediated by cytotoxic T cell mechanisms alone (reviewed in (11)). The demonstration of antigen-stimulated plasma cell antibody production (8) and now a circulating IBM autoantibody against a 43 kDa muscle protein provides compelling evidence for humoral autoimmunity in IBM. Because of the principal of linked recognition (B cell aided maturation of T cell requires that both B cell immunoglobulin and T cell receptor recognize the same molecular complex), antigens to which autoantibodies are directed may also be candidates for T cell directed autoimmunity. The sensitivity was 52% and the specificity was 100% of this autoantibody, in the group of IBM and other inflammatory myopathy patients described herein.

Example 2

Autoantigen Identification in Inclusion Body Myositis

Two independent approaches to antigen identification have identified cytosolic 5'-nucleotidase 1A (NT5C1A) as the at least ~43 kDa autoantigen previously reported (21) in patients with inclusion body myositis (IBM).

In the first approach, a screening method using 2-Dimensional gel separation of human muscle lysates probed with a human IBM blood sample yielded identification of NT5C1A as a potential candidate (Table 1). This is an approximately 41 kDa protein identified on the basis of at least seven distinct matching peptides found in the trypsin digest of an appropriate band by mass spectrometry.

In the second approach, a comprehensive peptidome screening assay (22) containing over 400,000 peptides representing over 24,000 proteins was applied to 6 IBM blood samples. Exceedingly high scores were identified for 5 distinct NT5C1A peptides from 4 of the 6 samples (Table 2). For 3 samples, NT5C1A peptide ranked #1 from among more than 400,000 peptides and for the 4th sample NT5C1A peptides ranked #2 and #3, with p-values ranging from approximately $10^{-171}$ to $10^{-434}$. Multiple highly scored NT5C1A peptides were detected in each of the 4 samples. The 2 samples without highly ranked NT5C1A peptide reactivity both showed high reactivity to peptides from a highly homologous paralog gene NT5C1B with ranks #29 and #30 and estimated p-values of $10^{-10}$ to $10^{-38}$. Although NT5C1B is not an approximately 43 kDa protein (MW 69 kDa), it has approximately 65% identical to NT5C1A and antibody reactivity to NT5C1B peptides likely reflects cross reactivity to NT5C1A.

Peptidome screening assay demonstrated strong binding of IBM plasma to the NT5C1A peptide AKIFYDNLAPKKKPKSPKPQNAVTIAVSSRALFRMD (SEQ. ID. NO:6) in two patients (Sample 4 and Sample 6) and no binding with patient Sample 3 as listed in Table 2. To confirm that SEQ. ID. NO:6 was recognized by autoantibodies in Sample 4 and Sample 6, these 3 samples were tested in a Western blot analysis against this peptide (SEQ. ID. NO:6) as well as dot blots. Both the Western blot and dot blot showed strong reactivity in Sample 4 and Sample 6 but no reactivity in Sample 3 (data not shown). This confirms reactivity of IBM plasma against the NT5C1A peptide.

The position of the peptide AKIFYDNLAPKKKPKSPKPQNAVTIAVSSRALFRMD (SEQ. ID. NO:6) within NT5C1A is highlighted in bold the FASTA sequence shown in SEQ. ID. NO:1. A BLAST search of this peptide sequence against the human protein nr database showed that only human NT5C1A contains this sequence, confirming that reactivity is against the protein NT5C1A.

NT5C1A Immunohistochemistry of IBM Muscle Biopsy Specimens

Immunohistochemistry of two out of six IBM muscle samples have demonstrated abnormal distribution of the NT5C1A protein, which appears to be aggregated in the muscle sarcoplasm (data not shown).

Example 3

Exemplary Diagnostic Semi-Quantitative Lateral Flow Immunoassay Test Strips

The levels of auto-antibodies described herein can also be determined using test strips as illustrated in FIG. 3-4. In the test strip, the membrane is divided into three separate regions: a sample (S) position at one end of the membrane, a test (T) position located at the middle of the membrane, and a control (C) position found at the opposite end the membrane (FIG. 3A). Located at S is an excess quantity of dehydrated desired antigen. The desired antigen can be a 43 kDa protein from a muscle lysate, a NTC1A, a NTC1B isoform, or peptide thereof, or an isolated peptide or fusion protein described herein. The desired antigen can be conjugated to colloidal gold beads or latex beads for visualization purposes. At T, there is an excess quantity of anti-IgG antibodies immobilized on the membrane. At C, there is another immobilized anti-IgG antibody that is reactive to the desired antigen (FIG. 3A).

The excess quantity of dehydrated desired antigen at S position is such that when a sample (e.g. serum) is applied at S, autoantibody-antigen complexes are formed as well as there is free antigen are still available to bind the immobilized anti-IgG at position C.

The S position is where a sample of serum is applied. The arrowheads delineate the boundary limit that the sample serum should not cross on the membrane when applying the serum to the membrane. The water in the serum rehydrates the desired antigen. An antibody-antigen complex is produced when the autoantibody reactive to forms a complex with the rehydrated desired antigen. A mixture of the autoantibody-antigen complexes and non-complexed antigen move by capillary action away from position S towards position T and C.

Upon arrival at the T position, the autoantibody-antigen complex will bind the immobilized anti-IgG antibody and be immobilized at the T position. The localized concentration of autoantibody-antigen complex that is colloidal gold or latex bead labeled will become visible as a colored line at the T position (FIG. 4, middle test strip). The greater the amount of autoantibodies in the sample, the broader the visible band at T. When the area remains clear at the T position, this means that there no or below detectable levels of autoantibodies (FIG. 4, far left test strip). At the C position, the free and labeled antigen originating from position S will be bound and captured by the immobilized anti-IgG that is reactive to the desired antigen. This will in turn result in a concentration of a colloidal gold or latex bead labeled at the C position and will become visible as colored line at the C position. The C position result serves as a test control that there is functional in the test strip and should always be present (FIG. 4).

The test strip can be designed in a form of a dipstick test strip (FIG. 3B). As a dipstick test strip, the strip is dipped into a sample of serum at the S position end with sample level not to exceed the boundary limit. The strip is then laid horizontally with the membrane surface facing up on a flat surface. A fixed amount of time is given for the rehydration of the desired antigen, capillary action, and antibody binding reaction to take place. At the end of the fixed time, there should be visible bands at the C position and depending on the level of auto-anti-antibody, there may or may not be a visible band at the T position (FIG. 4).

Example 4

Exemplary Semi-Quantitative Diagnostic ELISA Immunoassay

The levels of autoantibodies described herein can be determined using an ELISA assay as illustrated in FIG. 5. An ELISA assay comprises performing a standard calibration or titration assay and a sample assay in order to determine the amount of autoantibodies in a sample obtained from a subject. As shown, the ELISA assay microtiter plate consists of two duplicate reference rows for performing a standard calibration or titration assay. Increasing amount of human IgG is placed and immobilized in individual wells of each reference row to produce the data which will be used to generate a standard calibration or titration curve. Standard amounts of IgG protein ranging from 0-50 ng/ml or pg/ml are placed in the reference rows. Excess amounts desired antigen are immobilized in the sample wells of plate. The desired antigen in these sample wells function to capture any autoantibodies in the test sample. A test sample (e.g., blood, serum or plasma) is placed in the sample wells. Subsequently, a horse-radish peroxidase labeled anti-human IgG antibody is added to the wells. The mixtures in the wells are allowed to incubate at room temperature for 90 min and the liquid is decanted. The wells are washed five times with deionized water. Then an aliquot of 3,3',5,5' tetramethylbenzidine (TMB) reagent is added into each well. The mixture is gently mixed for 10 seconds and incubated at room temperature (18-25° C.) for 20 minutes. The enzymatic reaction is terminated by adding 1N HCl. Gentle agitation is carried out till all the blue color changes to yellow color completely. The amount of color by-product is determined by reading its absorbance at 450 nm with a microtiter well reader. The $A_{450}$ correspond to the amount of human IgG antibodies in the wells. The amount of the auto-antibodies in a test sample can be estimated from the $A_{450}$ obtained from the sample wells and the standard calibration or titration curve is generated from the data obtained from the reference wells.

In an alternate embodiment, the modified ELISA assay as shown in FIG. 6 can be used. As in FIG. 5, the reference rows and sample wells are labeled (FIG. 6). Excess amounts of desired antigen are immobilized in the sample wells of plate. A fixed amount of human IgG is placed in duplicate reference wells. This fixed amount is the reference value corresponds to the average amount of the autoantibodies found in the blood test sample serum of non-IBM healthy subjects. The blood sample, serum or plasma, is also placed in the duplicate sample wells. The assay plate is process as described herein. The $A_{450}$ obtained from the sample wells are compared with those obtained for the corresponding reference rows in order to determine whether there is an increase or decrease in the amount of autoantibodies in the test sample.

REFERENCES

1. Mammen A L (2010) Dermatomyositis and polymyositis: Clinical presentation, autoantibodies, and pathogenesis. Ann N Y Acad Sci 1184: 134-153.
2. Dalakas M C, IIIa I, Gallardo E, Juarez C (1997) Inclusion body myositis and paraproteinemia: incidence and immunopathologic correlations. Ann Neurol 41: 100-104.

3. Hengstman G J, Brouwer R, Egberts W T, Seelig H P, Jongen P J, et al. (2002) Clinical and serological characteristics of 125 Dutch myositis patients. Myositis specific autoantibodies aid in the differential diagnosis of the idiopathic inflammatory myopathies. J Neurol 249: 69-75.
4. Engel A G, Arahata K (1984) Monoclonal antibody analysis of mononuclear cells in myopathies. II: Phenotypes of autoinvasive cells in polymyositis and inclusion body myositis. Ann Neurol 16: 209-215.
5. Greenberg S A (2001) DNA microarray gene expression analysis technology and its application to neurological disorders. Neurology 57: 755-761.
6. Greenberg S A, Sanoudou D, Haslett J N, Kohane I S, Kunkel L M, et al. (2002) Molecular profiles of inflammatory myopathies. Neurology 59: 1170-1182.
7. Greenberg S A, Bradshaw E M, Pinkus J L, Pinkus G S, Burleson T, et al. (2005) Plasma cells in muscle in inclusion body myositis and polymyositis. Neurology 65: 1782-1787.
8. Bradshaw E M, Orihuela A, McArdel S L, Salajegheh M, Amato A A, et al. (2007) A Local Antigen-Driven Humoral Response Is Present in the Inflammatory Myopathies. J Immunol 178: 547-556.
9. Salajegheh M, Pinkus J L, Amato A A, Morehouse C, Jallal B, et al. (2010) Permissive environment for B-cell maturation in myositis muscle in the absence of B-cell follicles. Muscle Nerve 42: 576-583.
10. Sato S, Hirakata M, Kuwana M, Suwa A, Inada S, et al. (2005) Autoantibodies to a 140-kd polypeptide, CADM-140, in Japanese patients with clinically amyopathic dermatomyositis. Arthritis Rheum 52:1571-1576.
11. Greenberg S A (2007) Proposed immunologic models of the inflammatory myopathies and potential therapeutic implications. Neurology 69: 2008-2019.
12. Ghirardello A, Rampudda M, Ekholm L, Bassi N, Tarricone E, et al. (2010) Diagnostic performance and validation of autoantibody testing in myositis by a commercial line blot assay. Rheumatology (Oxford) 49: 2370-2374.
13. Koffman B M, Rugiero M, Dalakas M C (1998) Immune-mediated conditions and antibodies associated with sporadic inclusion body myositis. Muscle Nerve 21: 115-117.
14. Brouwer R, Hengstman G J, Vree Egberts W, Ehrfeld H, Bozic B, et al. (2001) Autoantibody profiles in the sera of European patients with myositis. Ann Rheum Dis 60: 116-123.
15. Gunawardena H, Betteridge Z E, McHugh N J (2008) Newly identified autoantibodies: relationship to idiopathic inflammatory myopathy subsets and pathogenesis. Curr Opin Rheumatol 20: 675-680.
16. Limaye V S, Lester S, Bardy P, Thompson P, Cox S, et al. (2010 [Epub ahead of print]) A three-way interplay of DR4, autoantibodies and synovitis in biopsy-proven idiopathic inflammatory myositis. Rheumatol Int.
17. Sordet C, Goetz J, Sibilia J (2006) Contribution of autoantibodies to the diagnosis and nosology of inflammatory muscle disease. Joint Bone Spine 73: 646-654.
18. Sato S, Hoshino K, Satoh T, Fujita T, Kawakami Y, et al. (2009) RNA helicase encoded by melanoma differentiation-associated gene 5 is a major autoantigen in patients with clinically amyopathic dermatomyositis: Association with rapidly progressive interstitial lung disease. Arthritis Rheum 60: 2193-2200.
19. Salajegheh M, Kong S W, Pinkus J L, Walsh R J, Liao A, et al. (2010) Interferon-stimulated gene 15 (ISG15) conjugates proteins in dermatomyositis muscle with perifascicular atrophy. Ann Neurol 67: 53-63.
20. Hoogendijk J E, Amato A A, Lecky B R, Choy E H, Lundberg I E, et al. (2004) 119th ENMC international workshop: trial design in adult idiopathic inflammatory myopathies, with the exception of inclusion body myositis, 10-12 Oct. 2003, Naarden, The Netherlands. Neuromuscul Disord 14:337-345.
21. Salajegheh M, Lam T, Greenberg S A. Autoantibodies against a 43 KDa muscle protein in inclusion body myositis. PLoS One. 2011; 6:e20266
22. Larman H B, Zhao Z, Laserson U et al. Autoantigen discovery with a synthetic human peptidome. Nat Biotechnol. 2011; 29:535-541

TABLE 1

NT5C1A protein identified by mass spectrometry of a band removed from a 2-D gel corresponding with a reactive band from an IBM patient plasma sample.

| Accession Number | Protein Description | Mass | Mascot Score | Elution [min] | Sequence | Exp. m/z | Exp. Charge | Match Error Probability |
|---|---|---|---|---|---|---|---|---|
| IPI:IPI00000146.1 | Tax_Id=9606 Gene_Symbol= NT5C1A Cytosolic 5'-nucleotidase 1A | 41191.17 | 47.63 | 18.75425 | K.SPKPQNAVTIAVSSR.A | 519.3246 | 3 | 1.53E-05 |
| | | | 51.71 | 18.79737 | K.SPKPQNAVTIAVSSR.A | 519.2615 | 3 | 1.15E-10 |
| | | | 64.37 | 16.51299 | R.DVVVSQSQLR.V | 566.583 | 2 | 0 |
| | | | 51.62 | 16.62047 | R.DVVVSQSQLR.V | 565.9702 | 2 | 1.39E-10 |
| | | | 52.19 | 28.7559 | R.EAIDEGIAAATIFSPSR.D | 875.6157 | 2 | 3.72E-11 |
| | | | 47.89 | 22.38639 | R.EPGPGAETAAAPVWEEAK.I | 905.7371 | 2 | 6.55E-06 |

TABLE 1-continued

NT5C1A protein identified by mass spectrometry of a band removed from a 2-D gel corresponding with a reactive band from an IBM patient plasma sample.

| Accession Number | Protein Description | Mass | Mascot Score | Elution [min] | Sequence | Exp. m/z | Exp. Charge | Match Error Probability |
|---|---|---|---|---|---|---|---|---|
| | | | 46.68 | 26.80885 | R.LINSINHYDLFIER.F | 583.1718 | 3 | 0 |
| | | | 54.81 | 26.84406 | R.LINSINHYDLFIER.F | 583.3791 | 3 | 0 |
| | | | 47.49 | 32.52767 | R.SWGLETDEALFLAGAPK.G | 903.1512 | 2 | 1.8E-05 |
| | | | 86.46 | 26.69042 | R.VAFDGDAVLFSDESER.I | 879.4851 | 2 | 0 |

TABLE 2

Peptidome library screen of 6 samples identified highly scored NT5C1A and NT5C1B peptides in all samples. Numbers represent $-\log_{10}$ p-values (e.g., 5.47 = p-value of $10^{-5.47}$). The peptides are SEQ. ID. NO: 6-12 respectively in order of appearance in the table.

| Protein | Peptide | Sample1 | Sample2 | Sample3 | Sample4 | Sample5 | Sample6 | Peptide |
|---|---|---|---|---|---|---|---|---|
| NT5C1A | Pep-2 | 0.17 | 5.47 | 0.03 | 293.52 | 0.01 | 171.36 | AKIFYDNLAPKKKPKSPKPQNAVTIAVSSRALFRMD |
| NT5C1A | Pep-3 | 0.28 | 434.78 | 0.28 | 0.04 | 36.88 | 21.85 | RALFRMDEEQQIYTEQGVEEYVRYQLEHENEPFSPG |
| NT5C1A | Pep-8 | 0.3 | 3.03 | 0.19 | 3.44 | 201.95 | 173.05 | SQLRVAFDGDAVLFSDESERIVKAHGLDRFFEHEKA |
| NT5C1A | Pep-12 | 0.01 | 0.1 | 0.35 | 0.15 | 0.27 | 7.07 | KIRPHIFFDDQMFHVAGAQEMGTVAAHVPYGVAQTP |
| NT5C1A | Pep-13 | 0.02 | 0.01 | 0.48 | 3.1 | 0.01 | 25.3 | HVAGAQEMGTVAAHVPYGVAQTPRRTAPAKQAPSAQ |
| NT5C1B | Pep-3 | 38.41 | 0.16 | 10.98 | 0.38 | 0.01 | 0.93 | SQWSRISRSPSTKAPSIDEPRSRNTSAKLPSSSTSS |
| NT5C1B | Pep-15 | 0.01 | 0.28 | 0.01 | 0.96 | 80.1 | 1.76 | DGDAVLFSDESEHFTKEHGLDKFFQYDTLCESKPLA |

What is claimed is:

1. A method of treating inclusion body myositis (IBM) in a patient in need, the method comprising:
   (a) performing a non-invasive diagnosis to confirm IBM in the patient,
   wherein the non-invasive diagnosis comprises detecting the presence of an autoantibody in a serum or plasma sample obtained from said patient, wherein the autoantibody reacts with at least one ~43 kDa antigen,
   wherein the detection is by performing an immunoassay with the serum or plasma sample obtained from said patient with a human muscle extract or mammalian cell extract,
   wherein the immunoassay is a Western Blot analysis of a one-dimensional SDS-PAGE gel wherein the human muscle extract is separated on the ID SDS-PAGE,
   wherein said autoantibody, produces a detectable reactivity to the ~43 kDa antigen on the Western blot,
   wherein the patient has an inflammatory myopathy,
   and wherein the patient exhibits at least one of the following symptoms: progressive muscles weakness, muscle soreness or pain, muscle atrophy, dysphagia, joint pain, a propensity for falling and tripping, and muscle fatigue; and
   (b) administering an appropriate therapy to the patient in lieu of performing a muscle biopsy in said patient after confirming IBM when the presence of the autoantibody is detected in step (a), wherein said appropriate therapy comprises administering immunosupressives, or corticosteroids or a combination thereof.

2. The treatment method of claim 1, wherein the inflammatory myopathy is idiopathic.

3. The treatment method of claim 1, wherein the inflammatory myopathy is selected from the group consisting of dermatomyositis (DM), polymyositis (PM), or inclusion body myositis (IBM).

4. The treatment method of claim 1, wherein the human muscle extract or mammalian cell extract are obtained from healthy volunteers who are free of any infection or inflammatory diseases, or the use of inflammatory agents or vaccinations.

* * * * *

SEQUENCE LISTING

<160> NUMBER OF SEQ ID NOS: 23

<210> SEQ ID NO 1
<211> LENGTH: 368
<212> TYPE: PRT
<213> ORGANISM: Homo sapiens

<400> SEQUENCE: 1

Met Glu Pro Gly Gln Pro Arg Glu Pro Gln Glu Pro Arg Glu Pro Gly
1               5                   10                  15

Pro Gly Ala Glu Thr Ala Ala Ala Pro Val Trp Glu Glu Ala Lys Ile
                20                  25                  30

Phe Tyr Asp Asn Leu Ala Pro Lys Lys Lys Pro Lys Ser Pro Lys Pro
            35                  40                  45

Gln Asn Ala Val Thr Ile Ala Val Ser Ser Arg Ala Leu Phe Arg Met
        50                  55                  60

Asp Glu Glu Gln Gln Ile Tyr Thr Glu Gln Gly Val Glu Glu Tyr Val
    65                  70                  75                  80

Arg Tyr Gln Leu Glu His Glu Asn Glu Pro Phe Ser Pro Gly Pro Ala
                85                  90                  95

Phe Pro Phe Val Lys Ala Leu Glu Ala Val Asn Arg Arg Leu Arg Glu

```
            100                 105                 110
Leu Tyr Pro Asp Ser Glu Asp Val Phe Asp Ile Val Leu Met Thr Asn
        115                 120                 125

Asn His Ala Gln Val Gly Val Arg Leu Ile Asn Ser Ile Asn His Tyr
130                 135                 140

Asp Leu Phe Ile Glu Arg Phe Cys Met Thr Gly Asn Ser Pro Ile
145                 150                 155                 160

Cys Tyr Leu Lys Ala Tyr His Thr Asn Leu Tyr Leu Ser Ala Asp Ala
                165                 170                 175

Glu Lys Val Arg Glu Ala Ile Asp Glu Gly Ile Ala Ala Thr Ile
        180                 185                 190

Phe Ser Pro Ser Arg Asp Val Val Ser Gln Ser Gln Leu Arg Val
        195                 200                 205

Ala Phe Asp Gly Asp Ala Val Leu Phe Ser Asp Glu Ser Glu Arg Ile
210                 215                 220

Val Lys Ala His Gly Leu Asp Arg Phe Phe Glu His Glu Lys Ala His
225                 230                 235                 240

Glu Asn Lys Pro Leu Ala Gln Gly Pro Leu Lys Gly Phe Leu Glu Ala
                245                 250                 255

Leu Gly Arg Leu Gln Lys Lys Phe Tyr Ser Lys Gly Leu Arg Leu Glu
                260                 265                 270

Cys Pro Ile Arg Thr Tyr Leu Val Thr Ala Arg Ser Ala Ala Ser Ser
            275                 280                 285

Gly Ala Arg Ala Leu Lys Thr Leu Arg Ser Trp Gly Leu Glu Thr Asp
        290                 295                 300

Glu Ala Leu Phe Leu Ala Gly Ala Pro Lys Gly Pro Leu Leu Glu Lys
305                 310                 315                 320

Ile Arg Pro His Ile Phe Phe Asp Asp Gln Met Phe His Val Ala Gly
                325                 330                 335

Ala Gln Glu Met Gly Thr Val Ala Ala His Val Pro Tyr Gly Val Ala
                340                 345                 350

Gln Thr Pro Arg Arg Thr Ala Pro Ala Lys Gln Ala Pro Ser Ala Gln
                355                 360                 365

<210> SEQ ID NO 2
<211> LENGTH: 610
<212> TYPE: PRT
<213> ORGANISM: Homo sapiens

<400> SEQUENCE: 2

Met Ser Gln Thr Ser Leu Lys Gln Lys Lys Asn Glu Pro Gly Met Arg
1               5                   10                  15

Ser Ser Lys Glu Ser Leu Glu Ala Glu Lys Arg Lys Gly Ser Asp Lys
            20                  25                  30

Thr Gly Val Arg Leu Ser Asn Gln Met Arg Arg Ala Val Asn Pro Asn
        35                  40                  45

His Ser Leu Arg Cys Cys Pro Phe Gln Gly His Ser Ser Cys Arg Arg
    50                  55                  60

Cys Leu Cys Ala Ala Glu Gly Thr Ala Leu Gly Pro Cys His Thr Ile
65                  70                  75                  80

Arg Ile Tyr Ile His Met Cys Leu Leu Trp Glu Gln Gly Gln Gln Ile
                85                  90                  95

Thr Met Met Arg Gly Ser Gln Glu Ser Ser Leu Arg Lys Thr Asp Ser
            100                 105                 110
```

```
Arg Gly Tyr Leu Val Arg Ser Gln Trp Ser Arg Ile Ser Arg Ser Pro
            115                 120                 125

Ser Thr Lys Ala Pro Ser Ile Asp Glu Pro Arg Ser Arg Asn Thr Ser
130                 135                 140

Ala Lys Leu Pro Ser Ser Thr Ser Ser Arg Thr Pro Ser Thr Ser
145                 150                 155                 160

Pro Ser Leu His Asp Ser Ser Pro Pro Leu Ser Gly Gln Pro Ser
                165                 170                 175

Leu Gln Pro Pro Ala Ser Pro Gln Leu Pro Arg Ser Leu Asp Ser Arg
                180                 185                 190

Pro Pro Thr Pro Pro Glu Pro Asp Pro Gly Ser Arg Arg Ser Thr Lys
            195                 200                 205

Met Gln Glu Asn Pro Glu Ala Trp Ala Gln Gly Ile Val Arg Glu Ile
            210                 215                 220

Arg Gln Thr Arg Asp Ser Gln Pro Leu Glu Tyr Ser Arg Thr Ser Pro
225                 230                 235                 240

Thr Glu Trp Lys Ser Ser Gln Arg Arg Gly Ile Tyr Pro Ala Ser
                245                 250                 255

Thr Gln Leu Asp Arg Asn Ser Leu Ser Glu Gln Gln Gln Gln Arg
            260                 265                 270

Glu Asp Glu Asp Tyr Glu Ala Ala Tyr Trp Ala Ser Met Arg Ser
            275                 280                 285

Phe Tyr Glu Lys Asn Pro Ser Cys Ser Arg Pro Trp Pro Pro Lys Pro
            290                 295                 300

Lys Asn Ala Ile Thr Ile Ala Leu Ser Ser Cys Ala Leu Phe Asn Met
305                 310                 315                 320

Val Asp Gly Arg Lys Ile Tyr Glu Gln Glu Gly Leu Glu Lys Tyr Met
                325                 330                 335

Glu Tyr Gln Leu Thr Asn Glu Asn Val Ile Leu Thr Pro Gly Pro Ala
            340                 345                 350

Phe Arg Phe Val Lys Ala Leu Gln Tyr Val Asn Ala Arg Leu Arg Asp
            355                 360                 365

Leu Tyr Pro Asp Glu Gln Asp Leu Phe Asp Ile Val Leu Met Thr Asn
370                 375                 380

Asn His Ala Gln Val Gly Val Arg Leu Ile Asn Ser Val Asn His Tyr
385                 390                 395                 400

Gly Leu Leu Ile Asp Arg Phe Cys Leu Thr Gly Gly Lys Asp Pro Ile
                405                 410                 415

Gly Tyr Leu Lys Ala Tyr Leu Thr Asn Leu Tyr Ile Ala Ala Asp Ser
                420                 425                 430

Glu Lys Val Gln Glu Ala Ile Gln Glu Gly Ile Ala Ser Ala Thr Met
            435                 440                 445

Phe Asp Gly Ala Lys Asp Met Ala Tyr Cys Asp Thr Gln Leu Arg Val
450                 455                 460

Ala Phe Asp Gly Asp Ala Val Leu Phe Ser Asp Glu Ser Glu His Phe
465                 470                 475                 480

Thr Lys Glu His Gly Leu Asp Lys Phe Gln Tyr Asp Thr Leu Cys
                485                 490                 495

Glu Ser Lys Pro Leu Ala Gln Gly Pro Leu Lys Gly Phe Leu Glu Asp
                500                 505                 510

Leu Gly Arg Leu Gln Lys Lys Phe Tyr Ala Lys Asn Glu Arg Leu Leu
            515                 520                 525

Cys Pro Ile Arg Thr Tyr Leu Val Thr Ala Arg Ser Ala Ala Ser Ser
```

```
                530              535              540
Gly Ala Arg Val Leu Lys Thr Leu Arg Trp Gly Leu Glu Ile Asp
545                 550                 555                 560

Glu Ala Leu Phe Leu Ala Gly Ala Pro Lys Ser Pro Ile Leu Val Lys
                565                 570                 575

Ile Arg Pro His Ile Phe Phe Asp Asp His Met Phe His Ile Glu Gly
                580                 585                 590

Ala Gln Arg Leu Gly Ser Ile Ala Ala Tyr Gly Phe Asn Lys Lys Phe
                595                 600                 605

Ser Ser
    610

<210> SEQ ID NO 3
<211> LENGTH: 550
<212> TYPE: PRT
<213> ORGANISM: Homo sapiens

<400> SEQUENCE: 3

Met Ser Gln Thr Ser Leu Lys Gln Lys Lys Asn Glu Pro Gly Met Arg
1               5                   10                  15

Ser Ser Lys Glu Ser Leu Glu Ala Glu Lys Arg Lys Glu Ser Asp Lys
                20                  25                  30

Thr Gly Val Arg Leu Ser Asn Gln Gly Ser Gln Glu Ser Ser Leu Arg
            35                  40                  45

Lys Thr Asp Ser Arg Gly Tyr Leu Val Arg Ser Gln Trp Ser Arg Ile
    50                  55                  60

Ser Arg Ser Pro Ser Thr Lys Ala Pro Ser Ile Asp Glu Pro Arg Ser
65                  70                  75                  80

Arg Asn Thr Ser Ala Lys Leu Pro Ser Ser Thr Ser Ser Arg Thr
                85                  90                  95

Pro Ser Thr Ser Pro Ser Leu His Asp Ser Ser Pro Pro Leu Ser
                100                 105                 110

Gly Gln Pro Ser Leu Gln Pro Pro Ala Ser Pro Gln Leu Pro Arg Ser
            115                 120                 125

Leu Asp Ser Arg Pro Pro Thr Pro Pro Glu Pro Asp Pro Gly Ser Arg
    130                 135                 140

Arg Ser Thr Lys Met Gln Glu Asn Pro Glu Ala Trp Ala Gln Gly Ile
145                 150                 155                 160

Val Arg Glu Ile Arg Gln Thr Arg Asp Ser Gln Pro Leu Glu Tyr Ser
                165                 170                 175

Arg Thr Ser Pro Thr Glu Trp Lys Ser Ser Gln Arg Arg Gly Ile
                180                 185                 190

Tyr Pro Ala Ser Thr Gln Leu Asp Arg Asn Ser Leu Ser Glu Gln Gln
            195                 200                 205

Gln Gln Gln Arg Glu Asp Glu Asp Tyr Glu Ala Ala Tyr Trp Ala
    210                 215                 220

Ser Met Arg Ser Phe Tyr Glu Lys Asn Pro Ser Cys Ser Arg Pro Trp
225                 230                 235                 240

Pro Pro Lys Pro Lys Asn Ala Ile Thr Ile Ala Leu Ser Ser Cys Ala
                245                 250                 255

Leu Phe Asn Met Val Asp Gly Arg Lys Ile Tyr Glu Gln Glu Gly Leu
                260                 265                 270

Glu Lys Tyr Met Glu Tyr Gln Leu Thr Asn Glu Asn Val Ile Leu Thr
            275                 280                 285
```

Pro Gly Pro Ala Phe Arg Phe Val Lys Ala Leu Gln Tyr Val Asn Ala
290                 295                 300

Arg Leu Arg Asp Leu Tyr Pro Asp Glu Gln Asp Leu Phe Asp Ile Val
305                 310                 315                 320

Leu Met Thr Asn Asn His Ala Gln Val Gly Val Arg Leu Ile Asn Ser
                325                 330                 335

Val Asn His Tyr Gly Leu Leu Ile Asp Arg Phe Cys Leu Thr Gly Gly
            340                 345                 350

Lys Asp Pro Ile Gly Tyr Leu Lys Ala Tyr Leu Thr Asn Leu Tyr Ile
        355                 360                 365

Ala Ala Asp Ser Glu Lys Val Gln Glu Ala Ile Gln Glu Gly Ile Ala
370                 375                 380

Ser Ala Thr Met Phe Asp Gly Ala Lys Asp Met Ala Tyr Cys Asp Thr
385                 390                 395                 400

Gln Leu Arg Val Ala Phe Asp Gly Asp Ala Val Leu Phe Ser Asp Glu
                405                 410                 415

Ser Glu His Phe Thr Lys Glu His Gly Leu Asp Lys Phe Phe Gln Tyr
            420                 425                 430

Asp Thr Leu Cys Glu Ser Lys Pro Leu Ala Gln Gly Pro Leu Lys Gly
        435                 440                 445

Phe Leu Glu Asp Leu Gly Arg Leu Gln Lys Lys Phe Tyr Ala Lys Asn
450                 455                 460

Glu Arg Leu Leu Cys Pro Ile Arg Thr Tyr Leu Val Thr Ala Arg Ser
465                 470                 475                 480

Ala Ala Ser Ser Gly Ala Arg Val Leu Lys Thr Leu Arg Arg Trp Gly
                485                 490                 495

Leu Glu Ile Asp Glu Ala Leu Phe Leu Ala Gly Ala Pro Lys Ser Pro
            500                 505                 510

Ile Leu Val Lys Ile Arg Pro His Ile Phe Phe Asp Asp His Met Phe
        515                 520                 525

His Ile Glu Gly Ala Gln Arg Leu Gly Ser Ile Ala Ala Tyr Gly Phe
530                 535                 540

Asn Lys Lys Phe Ser Ser
545                 550

<210> SEQ ID NO 4
<211> LENGTH: 402
<212> TYPE: PRT
<213> ORGANISM: Homo sapiens

<400> SEQUENCE: 4

Met Gln Glu Asn Pro Glu Ala Trp Ala Gln Gly Ile Val Arg Glu Ile
1               5                   10                  15

Arg Gln Thr Arg Asp Ser Gln Pro Leu Glu Tyr Ser Arg Thr Ser Pro
                20                  25                  30

Thr Glu Trp Lys Ser Ser Ser Gln Arg Arg Gly Ile Tyr Pro Ala Ser
            35                  40                  45

Thr Gln Leu Asp Arg Asn Ser Leu Ser Glu Gln Gln Gln Gln Gln Arg
        50                  55                  60

Glu Asp Glu Asp Tyr Glu Ala Ala Tyr Trp Ala Ser Met Arg Ser
65                  70                  75                  80

Phe Tyr Glu Lys Asn Pro Ser Cys Ser Arg Pro Trp Pro Lys Pro
                85                  90                  95

Lys Asn Ala Ile Thr Ile Ala Leu Ser Ser Cys Ala Leu Phe Asn Met
            100                 105                 110

Val Asp Gly Arg Lys Ile Tyr Glu Gln Glu Gly Leu Glu Lys Tyr Met
            115                 120                 125

Glu Tyr Gln Leu Thr Asn Glu Asn Val Ile Leu Thr Pro Gly Pro Ala
        130                 135                 140

Phe Arg Phe Val Lys Ala Leu Gln Tyr Val Asn Ala Arg Leu Arg Asp
145                 150                 155                 160

Leu Tyr Pro Asp Glu Gln Asp Leu Phe Asp Ile Val Leu Met Thr Asn
                165                 170                 175

Asn His Ala Gln Val Gly Val Arg Leu Ile Asn Ser Val Asn His Tyr
            180                 185                 190

Gly Leu Leu Ile Asp Arg Phe Cys Leu Thr Gly Lys Asp Pro Ile
        195                 200                 205

Gly Tyr Leu Lys Ala Tyr Leu Thr Asn Leu Tyr Ile Ala Ala Asp Ser
        210                 215                 220

Glu Lys Val Gln Glu Ala Ile Gln Glu Gly Ile Ala Ser Ala Thr Met
225                 230                 235                 240

Phe Asp Gly Ala Lys Asp Met Ala Tyr Cys Asp Thr Gln Leu Arg Val
                245                 250                 255

Ala Phe Asp Gly Asp Ala Val Leu Phe Ser Asp Glu Ser Glu His Phe
            260                 265                 270

Thr Lys Glu His Gly Leu Asp Lys Phe Phe Gln Tyr Asp Thr Leu Cys
        275                 280                 285

Glu Ser Lys Pro Leu Ala Gln Gly Pro Leu Lys Gly Phe Leu Glu Asp
        290                 295                 300

Leu Gly Arg Leu Gln Lys Lys Phe Tyr Ala Lys Asn Glu Arg Leu Leu
305                 310                 315                 320

Cys Pro Ile Arg Thr Tyr Leu Val Thr Ala Arg Ser Ala Ala Ser Ser
                325                 330                 335

Gly Ala Arg Val Leu Lys Thr Leu Arg Arg Trp Gly Leu Glu Ile Asp
            340                 345                 350

Glu Ala Leu Phe Leu Ala Gly Ala Pro Lys Ser Pro Ile Leu Val Lys
        355                 360                 365

Ile Arg Pro His Ile Phe Phe Asp Asp His Met Phe His Ile Glu Gly
        370                 375                 380

Ala Gln Arg Leu Gly Ser Ile Ala Ala Tyr Gly Phe Asn Lys Lys Phe
385                 390                 395                 400

Ser Ser

<210> SEQ ID NO 5
<211> LENGTH: 602
<212> TYPE: PRT
<213> ORGANISM: Homo sapiens

<400> SEQUENCE: 5

Met Ser Gln Thr Ser Leu Lys Gln Lys Lys Asn Glu Pro Gly Met Arg
1               5                   10                  15

Ser Ser Lys Glu Ser Leu Glu Ala Glu Lys Arg Lys Glu Ser Asp Lys
            20                  25                  30

Thr Gly Val Arg Leu Ser Asn Gln Met Arg Arg Ala Val Asn Pro Asn
        35                  40                  45

His Ser Leu Arg Cys Cys Pro Phe Gln Gly His Ser Ser Cys Arg Arg
    50                  55                  60

Cys Leu Cys Ala Ala Glu Gly Thr Ala Leu Gly Pro Cys His Thr Ile
65                  70                  75                  80

-continued

Arg Ile Tyr Ile His Met Cys Leu Leu Trp Glu Gln Gly Gln Gln Ile
                85                  90                  95
Thr Met Met Arg Gly Ser Gln Glu Ser Ser Leu Arg Lys Thr Asp Ser
            100                 105                 110
Arg Gly Tyr Leu Val Arg Ser Gln Trp Ser Arg Ile Ser Arg Ser Pro
            115                 120                 125
Ser Thr Lys Ala Pro Ser Ile Asp Glu Pro Arg Ser Arg Asn Thr Ser
    130                 135                 140
Ala Lys Leu Pro Ser Ser Ser Thr Ser Ser Arg Thr Pro Ser Thr Ser
145                 150                 155                 160
Pro Ser Leu His Asp Ser Ser Pro Pro Leu Ser Gly Gln Pro Ser
                165                 170                 175
Leu Gln Pro Pro Ala Ser Pro Gln Leu Pro Arg Ser Leu Asp Ser Arg
            180                 185                 190
Pro Pro Thr Pro Pro Glu Pro Asp Pro Gly Ser Arg Arg Ser Thr Lys
            195                 200                 205
Met Gln Glu Asn Pro Glu Ala Trp Ala Gln Gly Ile Val Arg Glu Ile
    210                 215                 220
Arg Gln Thr Arg Asp Ser Gln Pro Leu Glu Tyr Ser Arg Thr Ser Pro
225                 230                 235                 240
Thr Glu Trp Lys Ser Ser Ser Gln Arg Arg Gly Ile Tyr Pro Ala Ser
                245                 250                 255
Thr Gln Leu Asp Arg Asn Ser Leu Ser Glu Gln Gln Gln Gln Gln Arg
            260                 265                 270
Glu Asp Glu Asp Asp Tyr Glu Ala Ala Tyr Trp Ala Ser Met Arg Ser
            275                 280                 285
Phe Tyr Glu Lys Asn Pro Ser Cys Ser Arg Pro Trp Pro Pro Lys Pro
    290                 295                 300
Lys Asn Ala Ile Thr Ile Ala Leu Ser Ser Cys Ala Leu Phe Asn Met
305                 310                 315                 320
Val Asp Gly Arg Lys Ile Tyr Glu Gln Glu Gly Leu Glu Lys Tyr Met
                325                 330                 335
Glu Tyr Gln Leu Thr Asn Glu Asn Val Ile Leu Thr Pro Gly Pro Ala
            340                 345                 350
Phe Arg Phe Val Lys Ala Leu Gln Tyr Val Asn Ala Arg Leu Arg Asp
            355                 360                 365
Leu Tyr Pro Asp Glu Gln Asp Leu Phe Asp Ile Val Leu Met Thr Asn
    370                 375                 380
Asn His Ala Gln Val Gly Val Arg Leu Ile Asn Ser Val Asn His Tyr
385                 390                 395                 400
Gly Leu Leu Ile Asp Arg Phe Cys Leu Thr Gly Gly Lys Asp Pro Ile
                405                 410                 415
Gly Tyr Leu Lys Ala Tyr Leu Thr Asn Leu Tyr Ile Ala Ala Asp Ser
            420                 425                 430
Glu Lys Val Gln Glu Ala Ile Gln Glu Gly Ile Ala Ser Ala Thr Met
            435                 440                 445
Phe Asp Gly Ala Lys Asp Met Ala Tyr Cys Asp Thr Gln Leu Arg Val
    450                 455                 460
Ala Phe Asp Gly Asp Ala Val Leu Phe Ser Asp Glu Ser Glu His Phe
465                 470                 475                 480
Thr Lys Glu His Gly Leu Asp Lys Phe Phe Gln Tyr Asp Thr Leu Cys
                485                 490                 495

```
Glu Ser Lys Pro Leu Ala Gln Gly Pro Leu Lys Gly Phe Leu Glu Asp
            500                 505                 510

Leu Gly Arg Leu Gln Lys Lys Phe Tyr Ala Lys Asn Glu Arg Leu Leu
        515                 520                 525

Cys Pro Ile Arg Thr Tyr Leu Val Thr Ala Arg Ser Ala Ala Ser Ser
    530                 535                 540

Gly Ala Arg Val Leu Lys Thr Leu Arg Arg Trp Gly Leu Glu Ile Asp
545                 550                 555                 560

Glu Ala Leu Phe Leu Ala Gly Ala Pro Lys Ser Pro Ile Leu Val Lys
                565                 570                 575

Ile Arg Pro His Ile Phe Phe Asp Asp His Met Phe His Ile Glu Gly
            580                 585                 590

Ala Gln Arg Lys Ser Leu Gly Trp Met Ser
            595                 600

<210> SEQ ID NO 6
<211> LENGTH: 36
<212> TYPE: PRT
<213> ORGANISM: Homo sapiens

<400> SEQUENCE: 6

Ala Lys Ile Phe Tyr Asp Asn Leu Ala Pro Lys Lys Pro Lys Ser
1               5                   10                  15

Pro Lys Pro Gln Asn Ala Val Thr Ile Ala Val Ser Ser Arg Ala Leu
            20                  25                  30

Phe Arg Met Asp
        35

<210> SEQ ID NO 7
<211> LENGTH: 36
<212> TYPE: PRT
<213> ORGANISM: Homo sapiens

<400> SEQUENCE: 7

Arg Ala Leu Phe Arg Met Asp Glu Glu Gln Ile Tyr Thr Glu Gln
1               5                   10                  15

Gly Val Glu Glu Tyr Val Arg Tyr Gln Leu His Glu Asn Glu Pro
            20                  25                  30

Phe Ser Pro Gly
        35

<210> SEQ ID NO 8
<211> LENGTH: 36
<212> TYPE: PRT
<213> ORGANISM: Homo sapiens

<400> SEQUENCE: 8

Ser Gln Leu Arg Val Ala Phe Asp Gly Asp Ala Val Leu Phe Ser Asp
1               5                   10                  15

Glu Ser Glu Arg Ile Val Lys Ala His Gly Leu Asp Arg Phe Phe Glu
            20                  25                  30

His Glu Lys Ala
        35

<210> SEQ ID NO 9
<211> LENGTH: 36
<212> TYPE: PRT
<213> ORGANISM: Homo sapiens

<400> SEQUENCE: 9
```

-continued

```
Lys Ile Arg Pro His Ile Phe Asp Asp Gln Met Phe His Val Ala
1               5                   10                  15

Gly Ala Gln Glu Met Gly Thr Val Ala Ala His Val Pro Tyr Gly Val
                20                  25                  30

Ala Gln Thr Pro
            35

<210> SEQ ID NO 10
<211> LENGTH: 36
<212> TYPE: PRT
<213> ORGANISM: Homo sapiens

<400> SEQUENCE: 10

His Val Ala Gly Ala Gln Glu Met Gly Thr Val Ala Ala His Val Pro
1               5                   10                  15

Tyr Gly Val Ala Gln Thr Pro Arg Arg Thr Ala Pro Ala Lys Gln Ala
                20                  25                  30

Pro Ser Ala Gln
            35

<210> SEQ ID NO 11
<211> LENGTH: 36
<212> TYPE: PRT
<213> ORGANISM: Homo sapiens

<400> SEQUENCE: 11

Ser Gln Trp Ser Arg Ile Ser Arg Ser Pro Ser Thr Lys Ala Pro Ser
1               5                   10                  15

Ile Asp Glu Pro Arg Ser Arg Asn Thr Ser Ala Lys Leu Pro Ser Ser
                20                  25                  30

Ser Thr Ser Ser
            35

<210> SEQ ID NO 12
<211> LENGTH: 36
<212> TYPE: PRT
<213> ORGANISM: Homo sapiens

<400> SEQUENCE: 12

Asp Gly Asp Ala Val Leu Phe Ser Asp Glu Ser Glu His Phe Thr Lys
1               5                   10                  15

Glu His Gly Leu Asp Lys Phe Phe Gln Tyr Asp Thr Leu Cys Glu Ser
                20                  25                  30

Lys Pro Leu Ala
            35

<210> SEQ ID NO 13
<211> LENGTH: 24
<212> TYPE: PRT
<213> ORGANISM: Homo sapiens

<400> SEQUENCE: 13

Asp Gly Asp Ala Val Leu Phe Ser Asp Glu Ser Glu Arg Ile Val Lys
1               5                   10                  15

Ala His Gly Leu Asp Arg Phe Phe
                20

<210> SEQ ID NO 14
<211> LENGTH: 24
<212> TYPE: PRT
```

```
<213> ORGANISM: Homo sapiens

<400> SEQUENCE: 14

Asp Gly Asp Ala Val Leu Phe Ser Asp Glu Ser Glu His Phe Thr Lys
1               5                   10                  15
Glu His Gly Leu Asp Lys Phe Phe
            20

<210> SEQ ID NO 15
<211> LENGTH: 11
<212> TYPE: PRT
<213> ORGANISM: Homo sapiens

<400> SEQUENCE: 15

Gly Asp Ala Val Leu Phe Ser Asp Glu Ser Glu
1               5                   10

<210> SEQ ID NO 16
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Arg or Lys

<400> SEQUENCE: 16

His Gly Leu Asp Xaa Phe Phe
1               5

<210> SEQ ID NO 17
<211> LENGTH: 11
<212> TYPE: PRT
<213> ORGANISM: Homo sapiens

<400> SEQUENCE: 17

Gly Asp Ala Val Leu Phe Ser Asp Glu Ser Glu
1               5                   10

<210> SEQ ID NO 18
<211> LENGTH: 11
<212> TYPE: PRT
<213> ORGANISM: Homo sapiens

<400> SEQUENCE: 18

Gly Glu Ala Val Leu Phe Ser Asp Glu Ser Glu
1               5                   10

<210> SEQ ID NO 19
<211> LENGTH: 11
<212> TYPE: PRT
<213> ORGANISM: Homo sapiens

<400> SEQUENCE: 19

Gly Asp Ala Val Leu Phe Ser Asp Asp Ser Asp
1               5                   10

<210> SEQ ID NO 20
<211> LENGTH: 11
<212> TYPE: PRT
<213> ORGANISM: Homo sapiens

<400> SEQUENCE: 20

Gly Asp Ala Ala Leu Phe Ser Asp Glu Ser Glu
1               5                   10
```

```
<210> SEQ ID NO 21
<211> LENGTH: 11
<212> TYPE: PRT
<213> ORGANISM: Homo sapiens

<400> SEQUENCE: 21

Gly Asp Ala Ala Leu Phe Ser Asp Glu Ser Asp
1               5                   10

<210> SEQ ID NO 22
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1 to 8 "Gly Gly
      Gly Gly Ser" units

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5
```